(12) United States Patent
Frendéus et al.

(10) Patent No.: US 9,803,013 B2
(45) Date of Patent: *Oct. 31, 2017

(54) BIOLOGICAL MATERIALS AND USES THEREOF

(71) Applicant: BioInvent International AB, Lund (SE)

(72) Inventors: Björn Frendéus, Landskrona (SE); Roland Carlsson, Lund (SE); Ingrid Teige, Lund (SE); Linda Mårtensson, Bjärred (SE)

(73) Assignee: BioInvent International AB, Lund (SE)

( * ) Notice: Subject to any disclaimer, the term of this patent is extended or adjusted under 35 U.S.C. 154(b) by 178 days.

This patent is subject to a terminal disclaimer.

(21) Appl. No.: 14/250,898

(22) Filed: Apr. 11, 2014

(65) Prior Publication Data

US 2014/0314793 A1    Oct. 23, 2014

Related U.S. Application Data

(63) Continuation-in-part of application No. 13/053,846, filed on Mar. 22, 2011, now Pat. No. 8,758,749, which is a continuation of application No. 12/097,193, filed as application No. PCT/EP2006/012065 on Dec. 8, 2006, now Pat. No. 7,943,744.

(30) Foreign Application Priority Data

Dec. 12, 2005 (GB) .................................. 0525214.3

(51) Int. Cl.
| | |
|---|---|
| C07K 16/00 | (2006.01) |
| C07K 16/28 | (2006.01) |
| C07K 16/42 | (2006.01) |
| A61K 39/00 | (2006.01) |

(52) U.S. Cl.
CPC ...... *C07K 16/2803* (2013.01); *C07K 16/2821* (2013.01); *C07K 16/2833* (2013.01); *C07K 16/4283* (2013.01); *A61K 2039/505* (2013.01); *C07K 2317/21* (2013.01); *C07K 2317/622* (2013.01); *C07K 2317/73* (2013.01); *C07K 2317/732* (2013.01); *C07K 2317/75* (2013.01); *C07K 2317/94* (2013.01)

(58) Field of Classification Search
None
See application file for complete search history.

(56) References Cited

U.S. PATENT DOCUMENTS

| | | | |
|---|---|---|---|
| 4,816,567 | A | 3/1989 | Cabilly et al. |
| 5,530,101 | A | 6/1996 | Queen et al. |
| 5,643,872 | A | 7/1997 | Ali et al. |
| 5,695,760 | A | 12/1997 | Faanes et al. |
| 6,008,058 | A | 12/1999 | Spatola et al. |
| 6,416,958 | B2 | 7/2002 | Vidovic et al. |
| 7,943,744 | B2 | 5/2011 | Frendeus et al. |
| 8,758,749 | B2 | 6/2014 | Frendeus et al. |
| 2002/0041847 | A1 | 4/2002 | Goldenberg |
| 2004/0110226 | A1 | 6/2004 | Lazar et al. |
| 2006/0264380 | A1 | 11/2006 | Hellstrom et al. |
| 2009/0087427 | A1 | 4/2009 | Frendeus et al. |
| 2009/0209473 | A1 | 8/2009 | Hellstrom et al. |
| 2011/0045060 | A1 | 2/2011 | Ohhashi et al. |
| 2012/0087916 | A1 | 4/2012 | Frendeus et al. |
| 2013/0189260 | A1 | 7/2013 | Hansson et al. |
| 2014/0242072 | A1 | 8/2014 | Hansson |
| 2014/0314793 | A1 | 10/2014 | Frendeus et al. |
| 2015/0352207 | A1 | 12/2015 | Frendeus et al. |
| 2016/0280788 | A1 | 9/2016 | Hansson et al. |

FOREIGN PATENT DOCUMENTS

| | | |
|---|---|---|
| EP | 00314863 A2 | 5/1989 |
| EP | 00387701 A1 | 9/1990 |
| EP | 1190074 A1 | 3/2002 |
| EP | 2593481 A1 | 5/2013 |
| WO | WO-91/09967 A1 | 7/1991 |
| WO | WO-98/32845 A1 | 7/1998 |
| WO | WO-03/035696 A2 | 5/2003 |
| WO | WO-2004/023140 A1 | 3/2004 |
| WO | WO-2005/008250 A1 | 1/2005 |
| WO | WO-2005/058251 A2 | 6/2005 |
| WO | WO-2005/086568 A2 | 9/2005 |
| WO | WO-2007/068485 A2 | 6/2007 |
| WO | WO-2009/116322 A1 | 9/2009 |
| WO | WO-2010/112110 A1 | 10/2010 |
| WO | WO-2012/007516 A1 | 1/2012 |
| WO | WO-2013/045580 A1 | 4/2013 |
| WO | WO-2014/108456 A1 | 7/2014 |

OTHER PUBLICATIONS

Aalinkeel et al., "Gene Expression of Angiogenic Factors Correlates with Metastatic Potential of Prostate Cancer Cells," *Cancer Res.*, 2004, 64:5311-5321.

Abd-Elkareem, et al. "Increased urinary levels of the leukocyte adhesion molecules ICAM-1 and VCAM-1 in human lupus nephritis with advanced renal histological changes: preliminary findings," *Clin. Exp. Nephrol.*, (2010) 14:548-557.

Alduaij and Illidge, "The future of anti-CD20 monoclonal antibodies: are we making progress?" *Blood*, 117:2993-3001 (2011).

Bai et al., "Antigenic drift as a mechanism for tumor evasion of destruction by cytolytic T lymphocytes," *J. Clin. Invest.*, 2003, 111(10):1487-1496.

Beck et al., "Strategies and challenges for the next generation of therapeutic antibodies," *Nat. Rev. Immunol.*, 10:345-352 (2010).

(Continued)

*Primary Examiner* — Laura B Goddard
*Assistant Examiner* — Meera Natarajan
(74) *Attorney, Agent, or Firm* — McCarter & English, LLP; Steven G. Davis; Yu Lu

(57) ABSTRACT

The invention provides binding molecules, including antibody molecules which selectively bind to a cell surface antigen of a target cell, and wherein the binding molecules, on binding the cell surface antigen, induce cell death of the target cell. There is also provided methods of and pharmaceutical compositions for cell death induction and uses thereof.

15 Claims, 36 Drawing Sheets

(56) References Cited

OTHER PUBLICATIONS

Beers et al., Type II (tositumomab) anti-CD20 monoclonal antibody out performs type I (rituximab-like) reagents in B-cell depletion regardless of complement activation, *Blood*, 112(10):4170-4177 (2008).
Bibeau et al., "Impact of FcγRIIa-FcγRIIIa Polymorphisms and *KRAS* Mutations on the Clinical Outcome of Patients with Metastatic Colorectal Cancer Treated with Cetuximab plus Irinotecan," *J. Clin. Oncol.*, 27(7):1122-1129 (2009).
Borrebaeck and Carlsson, "Human therapeutic antibodies," *Curr. Opin. Pharmacol.*, 2001, 1:404-408.
Brekke and Sandlie, "Therapeutic Antibodies for Human Diseases at the Dawn of the Twenty-First Century," *Nat. Rev. Drug Discov.*, 2003, 2:52-62.
Brix et al., "Extracellularly Occurring Histone H1 Mediates the Binding of Thyroglobulin to the Cell Surface of Mouse Macrophages," *J. Clin. Invest.*, 102(2):283-293 (1998).
Budagyan et al., "Anti-ICAM-1 mAb inhibits apoptosis of thymocytes induced by human thymic stromal cells (HTSC) line," *Tissue Antigens*, 1996, 48(4-2):359, Abstract No. AS-3-02 and 6th International Workshop and Conference on Human Leukocyte Differentiation Antigens, Kobe, Japan, Nov. 10-14, 1996.
Burgess et al., "Possible disassociation of the heparin binding and mitogenic activities of heparin-binding (acidic fibroblast) growth factor-1 from its receptor binding activities by site directed mutagenesis of a single lysine residue," *J. Cell Biology*, 1990, 111:2129-2138.
Bylund and Yamamura, "Methods for Receptor Binding," *Methods in Neurotransmitter Receptor Analysis*, 1990, Chapter 1, New York: Raven Press Ltd.
Cao et al., "Suppression of angiogenesis and tumour growth by the inhibitor K1-5 generated by plasmin-mediated proteolysis," *PNAS*, 96:5728-5733 (1999).
Casset et al., "A peptide mimetic of an anti-CD4 monoclonal antibody by rational design," *Biochem. Biophys. Res. Comm.*, 2003, 307:198-205.
Cerutti et al., "CD40 Ligand and Appropriate Cytokines Induce Switching to IgG, IgA, and IgE and Coordinated Germinal Center and Plasmacytoid Phenotypic Differentiation in a Human Monoclonal IgM+IgD+ B Cell Line," *J. Immunol.*, 1998,160:2145-2157.
Chaouchi et al., "B Cell Antigen Receptor-Mediated Apoptosis," *J. Immunol.*, 1995, 154(7):3096-3104.
Chen et al., "Selection and analysis of an optimized anti-VEGF antibody: crystal structure of an affinity matured Fab in complex with antigen," *J. Molec. Biol.*, 1999, 293:865-881.
Cheson et al., "Monoclonal Antibody Therapy for B-Cell Non-Hodgkin's Lymphoma," *N. Engl. J. Med.*, 359:613-626 (2008).
Clackson et al., "Making antibody fragments using phage display libraries," *Nature*, 1991, 352:624-628.
Clynes et al., "Inhibitory Fc receptors modulate in vivo cytotoxicity against tumor targets," *Nat. Med.*, 6(4):443-446 (2000).
Coleman et al., "The Fc portion of UV3, an anti-CD54 monoclonal antibody, is critical for its antitumor activity in SCID mice with human multiple myeloma or lymphoma cell lines," *J. Immunol.*, 2006, 29(5):489-498.
Coleman, "Understanding the mechanism of action UV3, an anti-CD54 monoclonal antibody, in the therapy of multiple myeloma," dissertation, 2005, 193 pages.
Cosimi et al., "In Vivo Effects of Monoclonal Antibody to ICAM-1 (CD54) in Nonhuman Primates with Renal Allografts," *J. Immunol.*, 1990, 144(12):4604-4612.
Cragg et al., "Complement-mediated lysis by anti-CD20 mAb correlates with segregation into lipid rafts," *Blood*, 101(3):1045-1052 (2003).
Cragg and Glennie, "Antibody specificity controls in vivo effector mechanisms of anti-CD20 reagents," *Blood*, 103(7):2738-2743 (2004).

Daibata et al., "The Establishment of Epstein-Barr Virus Nuclear Antigen-Positive (SP-50B) and Epstein-Barr Virus Nuclear Antigen-Negative (SP-53) Cell Lines with t(11;14)(q13;q32) Chromosome Abnormality from an Intermediate Lymphocytic Lymphoma," *Cancer*, 1989, 64:1248-1253.
DePascalis et al., "Grafting of abbreviated complementarity determining regions containing specificity determining residues essential for ligand contact to engineer a less immunogenic humanized monoclonal antibody," *J. Immunol.*, 2002, 169:3076-3084.
Doyle et al., "Specific blockade by CD54 and MHC II of CD40-mediated signaling for B cell proliferation and survival," *Exper. Cell Res.*, 2001, 265(2):312-318.
Edvardsson et al., "A proteome analysis of livers from obese (ob/ob) mice treated with the peroxisome proliferator WY14,643," *Electrophoresis*, 1999, 20:935-942.
Fransson et al., "Rapid induction of apoptosis in B-cell lymphoma by functionally isolated human antibodies," *Int. J. Cancer*, 2006, 119(2):349-358.
Fukuda, "Restoration of Surface IgM-mediated apoptiosis in an anti-IgM-resistant variant of WEHI-231 lymphoma cells by HS1, a protein-tyrosine kinase substrate," *Proc. Natl. Acad. Sci. USA*, 1995, 92:7302-7306.
Gan et al., "Targeting a unique EGFR epitope with monoclonal antibody 806 activates NF-κB and initiates tumour vascular normalization," *J. Cell Mol. Med.*, 13(9B):3993-4001 (2009).
Ghosh et al., "Anti-adhesion molecule therapy for inflammatory bowel disease," *Therap. Adv. Gastroenterol.*, (2010) 3(4) 239-258.
Griffiths et al., "Human anti-self antibodies with high specificity from phage display libraries," *EMBO J.*, 1993, 12(2):725-734.
Grothey et al., "Serum levels of soluble intercellular adhesion molecule-1 (ICAM-1, CD54) in patients with non-small-cell lung cancer: correlation with histological expression of ICAM-1 and tumour stage," *Br. J. Cancer*, 1998, 77(5):801-807.
Hallborn and Carlsson, "Automated Screening Procedure for High-Throughput Generation of Antibody Fragments," *BioTechniques*, 2002, 33:S30-S37.
Harlow et al. (eds.), "Monoclonal Antibodies," *Antibodies A Laboratory Manual*, 1988, Chapter 6, Cold Spring Harbor Laboratory; Cold Spring Harbor, N.Y.
Haug et al., "A Phase I Trial of Immunosuppression with Anti-ICAM-1 (CD54) mAb in Renal Allograft Recipients," *Transplantation*, 1993, 55(4):766-773.
Hideshima et al., "Understanding multiple myeloma pathogenesis in the bone marrow to identify new therapeutic targets," *Nat. Rev. Cancer*, 7:585-598 (2007).
Holm et al., "Functional mapping and single chain construction of the anti-cytokeratin 8 monoclonal antibody TS1," *Molec. Immunol.*, 2007, 44:1075-1084.
Huang et al., "Anti-CD54 (ICAM-1) Has Antitumor Activity in SCID Mice with Human Myeloma Cells," *Cancer Res.*, 55:610-616 (1995).
Huang et al., "Cytotoxicity of a Novel Anti-ICAM-1 Immunotoxin on Human Myeloma Cell Lines," *Hybridoma*, 1993, 12(6):661-675.
Hogbom et al., "Structural basis for recognition by an in vitro evolved affibody," *Proc. Natl. Acad. Sci. USA*, 2003, 100(6):3191-3196.
Ivanov et al., "Monoclonal antibodies directed to CD20 and HLA-DR can elicit homotypic adhesion followed by lysosome-mediated cell death in human lymphoma and leukemia cells," *J. Clin. Invest.*, 119(8):2143-2159 (2009).
Johnson et al., "The Melanoma Progression-Associated Antigen P3.58 is Identical to the Intercellular Adhesion Molecule, ICAM-1," *Immunobiology*, 178:275-284 (1988).
Kapoor et al., "Anti-CD20 monoclonal antibody therapy in multiple myeloma," *Br. J. Haematol.*, 141:135-148 (2008).
Kavanaugh et al., "Repeat Treatment of Rheumatoid Arthritis Patients with a Murine Anti-Intercellular Adhesion Molecule 1 Monoclonal Antibody," *Arthritis Rheum.*, 40(5):849-853 (1997).
Kavanaugh et al., "Treatment of Refractory Rheumatoid Arthritis with a Monoclonal Antibody to Intercellular Adhesion Molecule 1," *Arthritis Rheum.*, 1994, 37(7):992-999.

(56) References Cited

OTHER PUBLICATIONS

Kennedy et al., "Incidence and nature of CD20-negative relapses following rituximab therapy in aggressive B-cell non-Hodgkin's lymphoma: a retrospective review," *Br. J. Haematol.*, 2002, 119:412-416.
Kim et al., "Transforming Growth Factor-.beta.1 Induces Apoptosis through Fas Ligand-independent Activation of the Fas Death Pathway in Human Gastric SNU-620 Carcinoma Cells," *Mol. Biol. Cell*, 2004, 15:420-434.
Kroemer, et al., "Classification of cell death: recommendations of the Nomenclature Committee on Cell Death 2009," *Cell Death and Differentiation* (2009) 16:3-11.
Kwak et al., "Induction of Immune Responses in Patients with B-Cell Lymphoma Against the Surface-Immunoglobulin Idiotype Expressed by their Tumors," *N. Engl. J. Med.*, 1992, 327(17):1209-1215.
Kyle et al., "Multiple Myeloma," *N. Engl. J. Med.*, 351:1860-1873 (2004).
Lazar, et al., "Transforming growth factor alpha: mutation of aspartick acid 47 and leucine 48 results in different biological activities," *Molec. Cell. Biol.*, 1988, 8:1247-1252.
Lejeune et al., "Evidence for Linkage Disequilibrium Between FcγRIIIa-V158F and FcγRIIIa-H131R Polymorphisms in White Patients, and for an FcγRIIIa-Restricted Influence on the Response to Therapeutic Antibodies," *J. Clin. Oncol.*, 26:5489-5491 and 5491-5482 (2008).
Lim et al., "Anti-CD20 monoclonal antibodies: historical and future perspectives," *Haematologica*, 95:135-143 (2010).
Lonberg, "Human antibodies from transgenic animals," *Nature Biotechnol.*, 2005, 23:1117-1125.
MacCallum et al., Antibody-antigen interactions: contact analysis and binding site topography, *J. Molec. Biol.*, 1996, 262:732-745.
Manches et al., "In vitro mechanisms of action of rituximab on primary non-Hodgkin Lymphomas," *Blood*, 101(3):949-954 (2003).
Marks et al., "By-passing Immunization. Human Antibodies from V-gene Libraries Displayed on Phage," *J. Mol. Biol.*, 1991, 222(3):581-597.
Marlin and Springer, "Purified Intercellular Adhesion Molecule-1 (ICAM-1) is a Ligand for Lymphocyte Function-Associated Antigen 1 (LFA-1)," *Cell*, 1987, 51:813-819.
Marquardt, "An Algorithm for Least-Square Estimation of Nonlinear Parameters," *J. Soc. Indust. Appl. Math.*, 1963, 11(9):431-441.
Maruo et al., "ICAM-1 Expression and the Soluble ICAM-1 Level for Evaluating the Metastatic Potential of Gastric Cancer," *Int. J. Cancer*, 2002, 100:486-490.
Menezes et al., "Establishment and Characterization of an Epstein-Barr Virus (EBV)-Negative Lymphoblastoid B Cell Line (BJA-B) from an Exceptional, EBV-Genome-Negative African Burkitt's Lymphoma," *Biomedicine*, 1975, 22:276-284.
Miele et al., "Enhanced Metastatic Ability of TNFα-Treated Malignant Melanoma Cells is Reduced by Intercellular Adhesion Molecular-1 (ICAM-1, CD54) Antisense Oligonucleotides," *Exp. Cell. Res.*, 1994, 214:231-241.
Mileski et al., "Clinical Effects of Inhibiting Leukocyte Adhesion with Monoclonal Antibody to Intercellular Adhesion Molecule-1 (Enlimomab) in the Treatment of Partial-Thickness Burn Injury," *J. Trauma*, 54:950-958 (2003).
Miller et al., "Treatment of B-Cell Lymphoma with Monoclonal Anti-Idiotype Antibody," *N. Engl. J. Med.*, 1982, 306(9):517-522.
Mitsiades et al., "Fluorescence Imaging of Multiple Myeloma Cells in a Clinically Relevant SCID/NOD in Vivo Model: Biologic and Clinical Implications," *Cancer Res.*, 63:6689-6696 (2003).
Musolino et al., "Immunoglobulin G Fragment C Receptor Polymorphisms and Clinical Efficacy of Trastuzumab-Based Therapy in Patients with HER-2/neu-Positive Metastatic Breast Cancer," *J. Clin. Oncol.*, 26(11):1789-1796 (2008).
Nagy and Mooney, "A novel, alternative pathway of apoptosis triggered through class II major histocompatibility complex molecules," *J. Mol. Med.*, 2003, 81:757-765.
Nagy et al., "Fully human, HLA-DR-specific monoclonal antibodies efficiently induce programmed death of malignant lymphoid cells," *Nat. Med.*, 2002, 8(8):801-807.
Nieda et al., "Dendritic cells rapidly undergo apoptosis in vitro following culture with activated CD4.sup.+ Vα24 natural killer T cells expressing CD4OL," *Immunology*, 2001, 102(2):137-145.
Nimmerjahn et al., "FcγRIV: A Novel FcR with Distinct IgG Subclass Specificity," *Immunity*, 23:41-51 (2005).
Nord et al., "Binding proteins selected from combinatorial libraries of an α-helical bacterial receptor domain," *Nat. Biotechnol.*, 1997, 15(8):772-777.
Norderhaug et al., "Versatile vectors for transient and stable expression of recombinant antibody molecules in mammalian cells," *J. Immunol. Meth.*, 1997, 204:77-87.
Norman et al., "Differential roles of ICAM-1 and VCAM-1 in leukocyte-endothelial cell interactions in skin and brain of MRL/fas$^{lpr}$ mice," *J. Leukocyte Biology*, 2008, 84:68-76.
Park et al., "The Therapeutic Effect of Anti-HER2/neu Antibody Depends on both Innate and Adaptive Immunity," *Cancer Cell*, 18(2):160-170 (2010).
Rau et al., "Anti-ICAM-1 Antibody Modulates Late Onset of Acinar Cell Apoptosis and Early Necrosis in Taurocholate-Induced Experimental Acute Pancreatitis," *Pancreas*, 2001, 23(1):80-88.
Rawstron et al., "Report of the European Myeloma Network on multiparametric flow cytometry in multiple myeloma and related disorders," *Haematologica*, 93(3):431-438 (2008).
Richardson et al., "Monoclonal antibodies in the treatment of multiple myeloma," *Br. J. Haematol.*, 154:745-754 (2011).
Riechmann et al., "Reshaping human antibodies for therapy," *Nature*, 1988, 332:323-327.
Robert et al., "Cutaneous side-effects of kinase inhibitors and blocking antibodies," *Lancet Oncol.*, 2005, 6:491-500.
Roche et al., "Fibrinogen mediates bladder cancer cell migration in an ICAM-1-dependent pathway," *Thromb. Haemost.*, 2003, 89:1089-1097.
Rosenthal, "A Graphic Method for the Determination and Presentation of Binding Parameters in a Complex System," *Anal. Biochem.*, 1967, 20:525-532.
Rosette et al., "Role of ICAM1 in invasion of human breast cancer cells," *Carcinogenesis*, 2005, 26(5):943-950.
Rothlein et al., "Cross-Linking of ICAM-1 Induced Co-Signaling of an Oxidative Burst from Mononuclear Leukocytes," *J. Immunol.*, 1994, 152:2488-2495.
Rudikoff et al., "Single amino acid substitution altering antigen-binding specificity," *PNAS*, 1982, 79:1979-1983.
Sabry et al., "Intercellular adhesion molecules in systemic lupus erythematosus patients with lupus nephritis," *Clin. Rheumatol.*, 2007, 26:1819-1823.
Saltman et al., "Characterization of a New Non-Hodgkin's Lymphoma Cell Line (NCEB-1) with a Chromosomal (11:14) Translocation [t(11:14)(q13;q32)]," *Blood*, 1988, 72(6):2026-2030.
Sampaio et al., "Expression of eight genes of nuclear factor-kappa B pathway in multiple myeloma using bone marrow aspirates obtained at diagnosis," *Histol. Histopathol.*, 24:991-997 (2009).
Schmidmaier et al., "The HMG-CoA reductase inhibitor simvastatin overcomes cell adhesion-mediated drug resistance in multiple myeloma by geranylgeranylation of Rho protein and activation of Rho kinase," *Blood*, 104(6):1825-1832 (2004).
Schmidmaier et al., "Evidence for cell adhesion-mediated drug resistance of multiple myeloma cells in vivo," *Int. J. Biol. Markers*, 21(4):218-222 (2006).
Schneider et al., "Safety, Pharmacokinetics and Biological Activity of Enlimomab (Anti-ICAM-1 Antibody): An Open-Label, Dose Escalation Study in Patents Hospitalized for Acute Stroke," *Eur. Neurol.* 40:78-83 (1998).
Smallshaw et al., "The generation and anti-myeloma activity of a chimeric anti-CD54 antibody, cUV3," *J. Immunother.*, 2004, 27(6):419-424.
Smith and Thomas, "Cellular expression of lymphocyte function associated antigens and the intercellular adhesion molecule-1 in normal tissue," *J. Clin. Pathol.*, 1990, 43:893-900.
Smith, "Rituximab (monoclonal anti-CD20 antibody): mechanisms of action and resistance," *Oncogene*, 22:7359-7368 (2003).

(56) References Cited

OTHER PUBLICATIONS

Soderlind et al., "Recombining germline-derived CDR sequences for creating diverse single-framework antibody libraries," *Nat. Biotechnol.*, 2000, 18(8):852-856.
Stebbings et al., "'Cytokine Storm' in the Phase I Trial of Monoclonal Antibody TGN1412: Better Understanding the Causes to Improve PreClinical Testing of Immunotherapeutics," *J. Immunol.*, 179:3325-3331 (2007).
Suarez et al., "Human monoclonal antibodies produced in transgenic BABκλ mice recognizing idiotypic immunoglobulins of human lymphoma cells," *Mol. Immunol.*, 2004, 41:519-526.
Sun et al., "Invasion and metastasis of liver cancer: expression of intercellular adhesion molecule 1," *J. Cancer Res. Clin. Oncol.*, 1999, 125:28-34.
Supplementary Apoptosis Data, "120320 Apoptosis with ICAM-1 antibodies using soluble FcgRIIIA as cross-linking," retrieved on Jan. 25, 2013, 2 pages.
Tang et al. "Important Roles for L-Selectin and OICAM-1 in the Development of Allergic Airway Inflammation in Asthma," *Pulmonary Pharmacology & Therapeutics*, 2001, 14:203-210.
Terry et al., "Localization of the rubella E1 epitopes," *Arch. Virol.*, 1988, 98:189-197.
Uyttenhove et al., "Escape of mouse mastocytoma P815 after nearly complete rejection is due to antigen-loss variants rather than immunosuppression," *J. Exp. Med.*, 1983, 157:1040-1052.
Vajdos et al., "Comprehensive functional maps of the antigenbinding site of an Anti-ErbB2 antibody contained by shotgun scanning mutagenesis," *J. Molec. Biol.*, 2002, 320:415-428.
van der Kolk et al., "Complement activation plays a key role in the side-effects of rituximab treatment," *Br. J. Haematol.*, 115:807-811 (2001).
Veitonmaki et al., "A Human ICAM-1 Antibody Isolated by a Function-First Approach Has Potent Macrophage-Dependent Antimyeloma Activity in Vivo," *Cancer Cell*, 2013, 23:502-515.
Vidovic and Toral, "Selective apoptosis of neoplastic cells by the HLA-DR-specific monoclonal antibody," *Cancer Letters*, 1998, 128:127-135.
Vyth-Dreese et al., "Functional Expression of Adhesion Receptors and Costimulatory Molecules by Fresh and Immortalized B-Cell Non-Hodgkin's Lymphoma Cells," *Blood*, 1995, 85(10):2802-2812.
Wang et al., "Effect of an anti-cd54 (ICAM-1) monoclonal antibody (UV3) on the growth of human uveal melanoma cells transplanted heterotopically and orthotopically in SCID mice," *Int. J. Cancer*, 2006, 118(4):932-941.
Weiner and Carter, "Tunable antibodies," *Nat. Biotechnol.*, 2005, 23(5):556-557.
Weiner and Kaminski, "Idiotype Variants Emerging After Anti-Idiotype Monoclonal Antibody Therapy of a Murine B Cell Lymphoma," *J. Immunol.*, 1989, 142:343-351.
Weiner et al., "Antibodies and cancer therapy: versatile platforms for cancer immunotherapy," *Nat. Rev. Immunol.*,10(5):317-327 (2010).
Weng and Levy, "Two Immunoglobulin G Fragment C Receptor Polymorphisms Independently Predict Response to Rituximab in Patients with Follicular Lymphoma," *J. Clin. Oncol.*, 21(21):3940-3947 (2003).
Weng et al., "Generating addressable protein-microarrays with PROfusion covalent mRNA-protein fusion technology," *Proteomics*, 2002, 2:48-57.
Wilson et al., "An Fcγ Receptor-Dependent Mechanism Drives Antibody-Mediated Target-Receptor Signaling in Cancer Cells," *Cancer Cell*, 19:101-113 (2011).
Wu et al., "Humanization of a murine monoclonal antibody by simultaneous optimization of framework and CDR 162 residues," *J. Molec. Biol.*, 1999, 294:151-162.
Xu et al., "Blockade of ICAM-1: A novel way of vasculitis treatment," *Biochem. Biophys. Res. Comm.*, 2009, 381:459-461.
Yaccoby et al., "Primary Myeloma Cells Growing in SCID-hu Mice: A Model for Studying the Biology and Treatment of Myeloma and its Manifestations," *Blood*, 92(8):2908-2913 (1998).

Yoshida et al., "Activated monocytes induce human retinal pigment epithelial cell apoptosis through caspase-3 activation," *Laboratory Investigation*, 2003, 83(8):1117-1129.
Zen et al., "Monocyte-derived macrophages prime peripheral T cells to undergo apoptosis by cell-cell contact via ICAM-1/LFA-1-dependent mechanism," *Immunobiology*, 1996, 195(3):323-333.
Zhang et al., "FCGR2A and FCG43A Polymorphisms Associated with Clinical Outcome of Epidermal Growth Factor Receptor-Expressing Metastatic Colorectal Cancer Patients Treated with Single-Agent Cetuximab," *J. Clin. Oncol.*, 25(24):3712-3718 (2007).
Zheng et al., "Macrophages are an abundant component of myeloma microenvironment and protect myeloma cells from chemotherapy drug-induced apoptosis," *Blood*, 114(17):3625-3628 (2009).
Zheng et al., "PSGL-1/selectin and ICAP-1/CD18 interactions are involved in macrophage-induced drug resistance in myeloma," *Leukaemia*, 27(3):702-710 (2013).
Albarracin and Fonseca, "Plasma cell leukemia," *Blood Revs.*, 25:107-112 (2011).
Alsina et al., "An In Vivo Model of Human Multiple Myeloma Bone Disease," *Stem Cells*, 13 Suppl 2:48-50 (1995).
*American Soc. Hematology Annual Meeting Abstracts*, 112(11) 9 pages, 2008.
Bellamy et al., "Development of an orthotopic SCID mouse-human tumor xenograft model displaying the multidrug-resistant phenotype," *Cancer Chemother. Pharmacol.*, 37:305-316 (1996).
Berg and Ostergaard, "Characterization of Intercellular Adhesion Molecule-1 (ICAM-1)-Augmented Degranulation by Cytotoxic T Cells," *J. Immunol.*, pp. 1694-1702 (1995).
Better et al., "*Escherichia coli* Secretion of an Active Chimeric Antibody Fragment," *Science*, 240: 1041-1043 (1988).
Bird et al., "Single-Chain Antigen-Binding Proteins," *Science*, 242: 423-426 (1988).
Boerner et al., "Protection of Antigen-Specific Human Monoclonal Antibodies from In Vitro-Primed Human Splenocytes," *J. Immunol.*, 147: 86-95 (1991).
Bruhns et al., "Specificity and affinity of human Fcγ receptors and their polymorphic variants for human IgG subclasses," *Blood*, 113: 3716-3725 (2009).
*Cancer Facts and Figures* 2008, American Cancer Society, 72 pages (2008).
Carter, "Potent antibody therapeutics by design," *Nat. Rev. Immunol.*, 6: 343-357 (2006).
Chauhan et al., "Multiple Myeloma Cell Adhesion-Induced Interleukin-6 Expression in Bone Marrow Stromal Cells Involves Activation of NF-κB" *Blood*, 87: 1104-1112 (1996).
Chauhan et al., "SHP2 Mediates the Protective Effect of Interleukin-6 Against Dexamethasone-Induced Apoptosis in Multiple Myeloma Cells," *J. Biol. Chem.*, 275: 27845-27850 (2000).
Chen et al., "Design of a genetic immunotoxin to eliminate toxin immunogenicity," *Gene Ther.*, 2:116-123 (1995).
Chirathaworn et al., "Stimulation Through Intercellular Adhesion Molecule-1 Provides a Second Signal for T Cell Activation," *J. Immunol.*, 168:5530-5537 (2002).
Choi et al., "AML-1AandAML-1B regulation of MIP-1α expression in multiple myeloma," *Blood*, 101: 3778-3783 (2003).
Coiffier, "Rituximab therapy in malignant lymphoma," *Oncogene*, 26: 3603-3613 (2007).
Cole et al., "Human monoclonal antibodies," *Mol. Cell. Biol.*, 62: 109-120 (1984).
Cole et al., "The EBV-Hybridoma Technique and its Application to Human Lung Cancer," *Monoclonal Antibodies and Cancer Therapy*, pp. 77-96 (1985).
Colman, "Effects of amino acid sequence changes on antibody-antigen interactions," *Res. Immunol.*, 145:33-36 (1994).
Comenzo, "How I treat amyloidosis," *Blood*, 114(15):3147-3157 (2009).
Cote et al., "Generation of human monoclonal antibodies reactive with cellular antigens," *Proc. Natl. Acad. Sci. USA*, 80:2026-2030 (1983).

(56) References Cited

OTHER PUBLICATIONS

Damle et al., "Costimulation with Integrin ligands Intercellular Adhesion Molecule-1 or Vascular Cell Adhesion Molecule-1 Augments Activation-Induced Death of Antigen-Specific CD4+ T lymphocytes," *J. Immunol.*, 151(5):2368-2379 (1993).
Dang et al., "Role of ICAM-1 in Antigen Presentation Demonstrated by ICAM-1 Defective Mutants," *J. Immunol.*, 144(11):4082-4091 (1990).
Davis et al., "Single-Agent Monoclonal Antibody Efficacy in Bulky Non-Hodgkin's Lymphoma: Results of a Phase II Trial of Rituximab," *J. Clin. Oncol.*, 17:1851-1857 (1999).
Davis et al., "Rituximab Anti-CD20 Monoclonal Antibody Therapy in Non-Hodgkin's Lymphoma: Safety and Efficacy of Re-Treatment," *J. Clin. Oncol.*, 18: 3135-3143 (2000).
de Bont et al., "Mobilized Human CD34 Hematopoietic Stem Cells Enhance Tumor Growth in a Nonobese Diabetic/Severe Combined Immunodeficient Mouse Model of Human Non-Hodgkin's Lymphoma," *Cancer Res.*, 61: 7654-7659 (2001).
Derossi et al., "Trojan peptides: the penetratin system for intracellular delivery," *Trends Cell Biol.*, 8: 84-87 (1998).
Di Micco and Di Micco, "Up-Date on Solitary Plasmacytoma and its Main Differences with Multiple Myeloma," *Exp. Oncol.*, 27(1):7-12 (2005).
Dingli and Russell, "Mouse models and the RANK/OPG axis in myeloma bone disease," *Leukemia*, 21:2090-2093 (2007).
Dores et al., "Plasmacytoma of bone, extramedullary plasmacytoma, and multiple myeloma: incidence and survival in the United States, 1992-2004," *Brit. J. Haematol.*, 144:86-94 (2008).
Dowlati et al., "Cell Adhesion Molecules, Vascular Endothelial Growth Factor, and Basic Fibroblast Growth Factor in Patients with Non-Small Cell Lung Cancer Treated with Chemotherapy with or without Bevacizumab—an Eastern Cooperative Oncology Group Study," *Clin. Cancer Res.*, 14(5): 1407-1412 (2008).
Drucker et al., "Thalidomide Down-Regulates Transcript Levels of GC-Rich Promoter Genes in Multiple Myeloma," *Mol. Pharmacol.*, 64: 415-420 (2003).
Feinman et al., "Role of NF-κB in the Rescue of Multiple Myeloma Cells from Glucocorticoid-Induced Apoptosis by Bcl-2," *Blood*, 93: 3044-3052 (1999).
Freshney, *Culture of Animal Cells: A Manual of Basic Technique*, Wiley-Liss, New York, NY, 2nd ed., Ch. 18, pp. 227-244 and Ch. 21, pp. 297-307 (1987).
Gertz, "Immunoglobulin Light Chain Amyloidosis: 2011 Update on Diagnosis, Risk-Stratification, and Management," *Am. J. Haematol.*, 86:181-186 (2011).
Gho et al., "Angiogenic Activity of Human Soluble Intercellular Adhesion Molecule-1," *Cancer Res.*, 59:5128-5132 (1999).
Gho et al., "Stimulation of Tumor Growth by Human Soluble Intercellular Adhesion Molecule-1," *Cancer Res.*, 61:4253-4257 (2001).
Giovanella et al., "Heterotransplantation of Human Malignant Tumors in 'Nude' Thymusless Mice. II. Malignant Tumors Induced by Injection of Cell Cultures Derived From Human Solid Tumors," *J. Natl. Can. Inst.*, 52(3): 921-930 (1974).
Hansson et al., "The Epitope Targeted by Apoptosis-Inducing ICAM-1 Antibody B11 is Highly Expressed in Multiple Myeloma," *Blood*, ASH Annual Meeting 114:Abstract 4897 (2009).
Harousseau, "Induction Therapy in Multiple Myeloma," *Hematology Am. Soc. Hematol. Educ. Program*, 2008:306-312 (2008).
He et al., "Genistein Down-Regulates the Constitutive Activation of Nuclear Factor-KB of Bone Marrow Stromal Cells in Multiple Myeloma, Leading to Suppression of Gene Expression and Proliferation," *Drug Dev. Res.*, 69:219-225 (2008).
Herold et al., "Rituximab Added to First-Line Mitoxantrone, Chlorambucil, and Prednisolone Chemotherapy Followed by Interferon Maintenance Prolongs Survival in Patients with Advanced Follicular Lymphoma: An East German Study Group Hematology and Oncology Study," *J. Clin. Oncol.*, 25(15):1986-1992 (2007).

Heuck, "Total Therapy Approach," UAMS Myeloma InstituteTotal Therapy Approach—UAMS Myeloma Institute, 3 pages, url: http://myeloma.uams.edu/treating-myeloma/total-therapy-approach/ (2014).
Hiddemann et al., "Frontline therapy with rituximab added to the combination of cyclophosphamide, doxorubicin, vincristine, and prednisone (CHOP) significantly improves the outcome for patients with advanced-stage follicular lymphoma compared with therapy with CHOP alone: results of a prospective randomized study of the German Low-Grade Lymphoma Study Group," *Blood*, 106(12):3725-3732 (2005).
Hideshima et al., "Thalidomide and its analogs overcome drug resistance of human multiple myeloma cells to conventional therapy," *Blood*, 96(9):2943-2950 (2000).
Hoogenboom and Winter, "By-passing Immunisation Human Antibodies from Synthetic Repertoires of Germline VH Gene Segments Rearranged in Vitro," *J. Mol. Biol.*, 227:381-388 (1992).
Horst et al., "Expression of the Leucocyte Integrin LFA-1 (CD11a/CD18) and its Ligand ICAM-1 (CD54) in Lymphoid Malignancies is Related to Lineage Derivation and Stage of Differentiation but Not to Tumor Grade," *Leukemia*, 5(10):848-853 (1991).
Huang et al., "Disseminated Growth of a Human Multiple Myeloma Cell Line in Mice with Severe Combined Immunodeficiency Disease," *Cancer Res.*, 53:1392-1396 (1993).
Huang and Vitetta, "Immunotherapy of Multiple Myeloma," *Stem Cells*, 13:123-134 (1995).
Hurrell, *Monoclonal Hybridoma Antibodies: Techniques and Applications*, CRC Press., Chapter 1, pp. 1-57, (1982).
Huston et al., "Protein engineering of antibody binding sites: Recovery of specific activity in an anti-digoxin single-chain Fv analogue produced in *Escherichia coli*," *Proc. Natl. Acad. Sci. USA*, 85:5879-5883 (1988).
Imai and Yachi, "Detection of Intercellular Adhesion Molecule ICAM-1 with Novel Monoclonal Antibody and its Significance of Malignant Diseases," First Dept. of Internal Medicine Sappor Medical College, vol. 34, No. 4, (313) 22 pages (1991).
Johnson et al., "Functional Aspects of Three Molecules Associated with Metastasis Development in Human Malignant Melanoma," *Invasion Metastasis*, 9(6):338-350 (1989).
Jones et al., "Replacing the complementarity-determining regions in a human antibody with those from a mouse," *Nature*, 321:522-525 (1986).
Kavanaugh et al., "A Phase I / II Open Label Study of the Safety and Efficacy of an Anti-ICAM-I (Intercellular Adhesion Molecule-1; CD54) Monoclonal Antibody in Early Rheumatoid Arthritis," *J. Rheumatol.*, 23(8):1338-1344 (1996).
Kawai et al., "Antitumor activity of humanized monoclonal antibody against HM1.24 antigen in human myeloma xenograft models," *Oncol. Rep.*, 15: 361-367 (2006).
Kawano et al., "Homotypic cell aggregations of human myeloma cells with ICAM-1 and LFA-1 molecules," *Brit. J. Haematol.*, 79:583-588 (1991).
Kim et al., "Cross-linking of CD54 on Burkitt Lymphoma Cell Line Raji and Ramos Induces FasL Expression by Reactive Oxygen Species and Apoptosis of Adjacent Cells in Fas/FasL Interaction," *J. Immunther.*, 30(7):727-739 (2007).
Kobune et al., "Wnt3/RhoA/ROCK signaling pathway is involved in adhesion-mediated drug resistance of multiple myeloma in an autocrine mechanism," *Mol. Cancer Ther.*, 6(6):1774-1784 (2007).
Kohler and Milstein, "Continuous cultures of fused cells secreting antibody of predefined specificity," *Nature*, 256:495-497 (1975).
Kozbor et al., "Specific Immunoglobulin Production and Enhanced Tumorigenicity Following Ascites Growth of Human Hybridomas," *J. Immunol Methods*, 81:31-42 (1985).
Kraj et al., "Flow Cytometric Immunophenotypic Characteristic of 36 Cases of Plasma Cell Leukemia," *Haematologica*, 95[suppl. 2]:388, abstract 0936 (2010).
Kraj et al., "Flow cytometric immunophenotypic characteristics of 36 cases of plasma cell leukemia," *Leukemia Res.*, 35:169-176 (2011).
Kumar et al., "Improved survival in multiple myeloma and the impact of novel therapies," *Blood*, 111(5):2516-2520 (2008).

(56) References Cited

OTHER PUBLICATIONS

Kussie et al., "A Single Engineered Amino Acid Substitution Changes Antibody Fine Specificity," *J. Immunol.*, pp. 146-152 (1993).
Kyle and Rajkumar, "Multiple myeloma," *Blood*, 111(6):2962-2672 (2008).
Kyle, "Clinical Aspects of Multiple Myeloma and Related Disorders Including Amyloidosis," *Multiple Myeloma and Amyloidosis*, Société d'Édition de l'Association d'Enseignement Médical des Hôpitaux de Paris 1999, 47(2):148-157 (1999).
Lacy et al., "Phase I, Pharmacokinetic and Pharmacodynamic Study of the Anti-Insulinlike Growth Factor Type 1 Receptor Monoclonal Antibody CP-751,871 in Patients with Multiple Myeloma," *J. Clin. Oncol.*, 26(19): 3196-3203 (2008).
Lane et al., "Rapid Signalling to B Cells by Antigen-Specific T Cells Requires CD18/CD54 Interaction," *J. Immunol.*, 147(12):4103-4108 (1991).
Li and Zhu, "A modified Boyden chamber assay for tumor cell transendothelial migration in vitro," *Clin. Exp. Metastasis*, 17:423-429 (1999).
Lokhorst et al., "Primary Tumor Cells of Myeloma Patients Induce Interleukin-6 Secretion in Long-Term Bone Marrow Cultures," *Blood*, 84(7): 2269-2277 (1994).
Lopes de Menezes et al., "Recombinant Interleukin-2 Significantly Augments Activity of Rituximab in Human Tumor Xenograft Models of B-cell Non-Hodgkin Lymphoma," *J. Immunother.*, 30(1):64-74 (2007).
Madan et al., "Clinical Features and Treatment Response of Light Chain (AL) Amyloidosis Diagnosed in Patients With Previous Diagnosis of Multiple Myeloma," *Mayo Clinic Proc.*, 85(3):232-238 (2010).
Marcus et al., "Phase III Study of R-CVP Compared with Cyclophosphamide, Vincristine, and Prednisone Alone in Patients with Previously Untreated Advanced Follicular Lymphoma," *J Clin Oncol.*, 26(28):4579-4586 (2008).
Martz, "LFA-1 and other Accessory Molecules Functioning in Adhesions of T and B Lymphocytes," *Human Immunol.*, 18:3-37 (1987).
McLaughlin et al., "Rituximab Chimeric Anti-CD20 Monoclonal Antibody Therapy for Relapsed Indolent Lymphoma: Half of Patients Respond to a Four-Dose Treatment Program," *J. Clin. Oncol.*, 16(8):2825-2833 (1998).
Merlini and Bellotti, "Molecular Mechanisms of Amyloidosis," *N. Eng. J. Med.*, 349(6):583-596 (2003).
Merlini et al., "Amyloidosis: Pathogenesis and New Therapeutic Options," *J. Clin. Oncol.*, 29(14):1924-1933 (2011).
Mézière et al., "In Vivo T Helper Cell Response to Retro-Inverso Peptidomimetics," *J. Immunol.*, 159:3230-3237 (1997).
Migkou et al., "Increased levels of Vascular Cell Adhesion Molecule-1 (VCAM-1) and Inter-Cellular Adhesion Molecule-1 (ICAM-1) Correlate with Advanced Disease Features and Poor Survival in Newly Diagnosed Patients with Multiple Myeloma. Reduction Post-Bortezomib- and Lenalidomide-Based Regimens," *51st ASH annual meeting and exposition*, New Orleans, LA, Abstract #1824, Poster Board 1-846, 114(22):724 (2009).
Mitsiades et al., "TRAIL/Apo2L ligand selectively induces apoptosis and overcomes drug resistance in multiple myeloma: therapeutic applications," *Blood*, 98(3): 795-804 (2001).
Mitsiades et al., "Apoptotic signaling induced by immunomodulatory thalidomide analogs in human multiple myeloma cells: therapeutic implications," *Blood*, 99(12):4525-4530 (2002).
Morrison et al., "Chimeric human antibody molecules: Mouse antigen-binding domains with human constant region domains," *Proc. Natl. Acad. Sci. USA*, 81: 6851-6855 (1984).
Nadav et al., "The Generation and Regulation of Functional Diversity of Malignant Plasma Cells," *Cancer Res.*, 66(17): 8608-8616 (2006).
Nishimoto et al., "Oncostatin M, Leukemia Inhibitory Factor, and Interleukin 6 Induce the Proliferation of Human Plasmacytoma Cells Via the Common Signal Transducer, GP130," *J. Exp. Med.*, 179:1343-1347 (1994).
Oriol, "Multiple Myeloma with Extramedullary Disease," *Adv. Ther.*, 28(Suppl. 7):1-6 (2011).
Orlandi et al., "Cloning immunoglobulin variable domains for expression by the polymerase chain reaction," *Proc. Natl. Acad. Sci. USA*, 86:3833-3837 (1989).
Ozaki et al., "Immunotherapy of Multiple Myeloma with a Monoclonal Antibody Directed Against a Plasma Cell-Specific Antigen, HM1.24," *Blood*, 90:3179-3186 (1997).
Pilkington et al., "In Vitro and in Vivo Models for the Study of Brain Tumour Invasion," *Anticancer Res.*, 17:4107-4109 (1997).
Poudrier and Owens, "CD54/Intercellular Adhesion Molecule 1 and Major Histocompatibility Complex II Signaling Induces B Cells to Express Interleukin 2 Receptors and Complements Help Provided through CD40 Ligation," *J. Exp. Med.*, 179:1417-1427 (1994).
Presta, "Antibody engineering," *Curr. Op. Struct. Biol.*, 2: 593-596 (1992).
Rajkumar et al., "Combination therapy with lenalidomide plus dexamethasone (Rev/Dex) for newly diagnosed myeloma," *Blood*, 106(13):4050-4053 (2005).
Rajkumar et al., "Monoclonal Gammopathy of Undetermined Significance, Waldenstrom Macroglobulinemia, AL Amyloidosis, and Related Plasma Cell Disorders: Diagnosis and Treatment," *Mayo Clin. Proc.*, 81(5):693-703 (2006).
Rajkumar, "Multiple myeloma: 2011 update on diagnosis, risk-stratification, and management," *Am. J. Haematol.*, 86:57-65 (2011).
Rajkumar et al., "Plasma cell leukemia," url: http://www.uptodate.com/contents/plasma-cell-leukemia, 3 pages, retrieved Sep. 9, 2011.
Ralph (and Drewinko rebuttal), Letters to the Editor re The human B cell lineage cell line ARH-77, *Cancer*, 56:2544-2545 (1985).
Ramsingh et al., "Primary Plasma Cell Leukemia. A Surveillance, Epidemiology, and End Results Database Analysis Between 1973 and 2004," *Cancer*, pp. 5734-5739 (2009).
Reilly et al., "The Native Structure of Intercellular Adhesion Molecule-1 (ICAM-1) is a Dimer Correlation with Binding to LFA-1," *J. Immunol.*, 155:529-532 (1995).
Ribatti et al., "The chick embryo chorioallantoic membrane as a model for in vivo research on angiogenesis," *Int. J. Dev. Biol.*, 40:1189-1197 (1996).
Rich, "Inhibitors of cysteine proteinases," *Protease Inhibitors*, Elsevier., Chapt. 4, pp. 153-178 (1986).
Richardson et al., "Thalidomide for Patients With Relapsed Multiple Myeloma After High-Dose Chemotherapy and Stem Cell Transplantation: Results of an Open-Label Multicenter Phase 2 Study of Efficacy, Toxicity, and Biological Activity," *Mayo Clinic Proc.*, 79(7):875-882 (2004).
Richardson et al., "Bortezomib or High-Dose Dexamethasone for Relapsed Multiple Myeloma," *N. Engl. J. Med.*, 352(24): 2487-2498 (2005).
Richardson et al., "A randomized phase 2 study of lenalidomide therapy for patients with relapsed or relapsed and refractory multiple myeloma," *Blood*, 108(10): 3458-3464 (2006).
Roebuck and Finnegan, "Regulation of intercellular adhesion molecule-1 (CD54) gene expression," *J. Leukoc. Biol.*, 66: 876-888 (1999).
Roodman, "Mechanisms of Bone Lesions in Multiple Myeloma and Lymphoma," *Skeletal Complications of Malignancy*, Suppl. to Cancer, 80(8): 1557-1563 (1997).
Salmela et al., "A Randomized Multicenter Trial of the Anti-ICAM-1 Monoclonal Antibody (Enlimomab) for the Prevention of Acute Rejection and Delayed Onset of Graft Function in Cadaveric Renal Transplantation," *Transplantation*, 67(5): 729-736 (1999).
Sambrook and Russell, *Molecular Cloning: A Laboratory Manual*, 3rd edition, Chapter 13, pp. 13.1-13.105, Cold Spring Harbor Laboratory Press (2001).
Sigma-Aldrich ARH 77 product information, European Collection of Cell Cultures, url: http://www.sigmaaldrich.com/catalog/product/sigma/88121202?lang=en&region=SE . . . , 2 pages (2015).

(56) References Cited

OTHER PUBLICATIONS

Singhal et al., "Antitumor Activity of Thalidomide in Refractory Multiple Myeloma," *N. Engl. J. Med.*, 341(21):1565-1571 (1999).
Siu et al., "Isolation of the Murine Intercellular Adhesion Molecule 1 (ICAM-1) Gene," *J. Immunol.*, 143(11):3813-3820 (1989).
Skerra and Plückthun, "Assembly of a Functional Immunoglobulin Fv Fragment in *Escherichia coli,*" *Science*, 240: 1038-1041 (1988).
Smadja et al., "Primary Plasma Cell Leukemia and Multiple Myeloma: One or Two Diseases According to the Methodology," *Blood*, 94:3607-3609 (1999).
Springer, "Traffic Signals for Lymphocyte Recirculation and Leukocyte Emigration: The Multistep Paradigm," *Cell*, 76:301-314 (1994).
Tai et al., "Mechanisms by which SGN-40, a Humanized Anti-CD40 Antibody, Induces Cytotoxicity in Human Multiple Myeloma Cells: Clinical Implications," *Cancer Res.*, 64: 2846-2852 (2004).
Takahashi et al., "A highly bone marrow metastatic marine breast cancer model established through in vivo selection exhibits enhanced anchorage-independent growth and cell migration mediated by ICAM-1," *Clin. Exp. Metastasis*, 25:517-529 (2008).
Thomas et al., "Interdependence between Cytokines and Cell Adhesion Molecules to Induce Interleukin-6 Production by Stromal Cells in Myeloma," *Leuk. Lymphoma*, 32(1-2): 107-119 (1998).
Thompson et al., "CLUSTAL W: improving the sensitivity of progressive multiple sequence alignment through sequence weighting, position-specific gap penalties and weight matrix choice," *Nuc. Acid Res.*, 22(22): 4673-4680 (1994).
Thorsett et al., "Dipeptide Mimics Conformationally Restricted Inhibitors of Angiotensin-Converting Enzyme," *Biochem. Biophys. Res. Comm.*, 111(1): 166-171 (1983).
Tian et al., "Cloning and Sequence Analysis of Tumor-Associated Gene hMMTAG2 from Human Multiple Myeloma Cell Line ARH-77," (Chinese language with English abstract), *Acta Biochimica et Biophysica Sinica*, 35(2): 143-148 (2003).
Tong et al., "Heterotransplantation of Human Multiple Myeloma Cell Lines Severe Combined Immunodeficiency (SCID) Mice," *Anticancer Res.*, 13: 593-597 (1993).
Tong et al., "Anti-CD40 Antibody Binding Modulates Human Multiple Myeloma Clonogenicity In Vitro," *Blood*, 84(9): 3026-3033 (1994).
Tong et al., "CD40 Ligand-Induced Apoptosis is Fas-Independent in Human Multiple Myeloma Cells," *Leuk. Lymphoma*, 36(5-6): 543-558 (2000).
Treon et al., "Tumor Cell Expression of CD59 is Associated with Resistance to CD20 Serotherapy in Patients with B-Cell Malignancies," *J. Immunother.*, 24(3): 263-271 (2001).
Treon et al., "CD20-Directed Serotherapy in Patients with Multiple Myeloma: Biologic Considerations and Therapeutic Applications," *J. Immunother.*, 25(1): 72-81 (2002).
Tsutani et al., "Discordant LFA-1/ICAM-1 Expression in a Case of Secondary Plasma Cell Leukemia Associated with Subcutaneous Plasmacytoma," *Am. J. Hematol.*, 42:299-304 (1993).
Ural et al., "The Bisphosphonate Zoledronic Acid Induces Cytotoxicity in Human Myeloma Cell Lines with Enhancing Effects of Dexamethasone and Thalidomide," *Int. J. Hematol.*, 78: 443-449 (2003).
Urashima et al., "CD40 Ligand Triggers Interleukin-6 Mediated B Cell Differentiation," *Leuk. Res.*, 20(6): 507-515 (1996).
Urashima et al., "The Development of a Model for the Homing of Multiple Myeloma Cells to Human Bone Marrow," *Blood*, 90(2): 754-765 (1997).
van Laar et al., "Translating a gene expression signature for multiple myeloma prognosis into a robust high-throughput assay for clinical use," *BMC Med. Genomics*, 7(25):1-13 (2014).
Veber et al., "Conformationally restricted bicyclic analogs of somatostatin," *Proc. Natl. Acad. Sci. USA*, 75(6): 2636-2640 (1978).
Veitonmäki et al., "Apoptosis-Inducing ICAM-1 Antibody Bi-505 is a Potent Inhibitor of Multiple Myeloma," Abstract B599, *XII International Myeloma Workshop, Clin. Lymphoma & Myeloma suppl.*, S157, Feb. 2009.

Veitonmäki et al., "Apoptosis-Inducing ICAM-1 Antibody BI-505 is a Potent Inhibitor of Multiple Myeloma," poster, Bioinvent Intl., Dept. of Haematology, Lund, SE (2009).
Verhoeyen et al., "Reshaping Human Antibodies: Grafting an Antilysozyme Activity," *Science*, 239:1534-1536 (1988).
Ward et al., "Binding activities of a repertoire of single immunoglobulin variable domains secreted from *Escherichia coli,*" *Nature*, 341: 544-546 (1989).
Winter and Milstein, "Man-made antibodies," *Nature*, 349: 293-299 (1991).
Wu et al., "Lenalidomide Enhances Natural Killer Cell and Monocyte-Mediated Antibody-Dependent Cellular Cytotoxicity of Rituximab-Treated CD20+ Tumor Cells," *Clin. Cancer Res.*, 14(14): 4650-4657 (2008).
Yaccoby et al., "Cancer and the Microenvironment: Myeloma-Osteoclast Interactions as a Model," *Cancer Res.*, 64: 2016-2023 (2004).
Ybarrondo et al., "Contribution of Lymphocyte Function-associated-1/Intercellular Adhesion Molecule-1 Binding to the Adhesion/Signaling Cascade of Cytotoxic T Lymphocyte Activation," *J. Exp. Med.*, 179:359-363 (1994).
Zola, *Monoclonal Antibodies: A Manual of Techniques*, Chapt. 4, pp. 63-87, CRC Press (1988).
Ho and Gibaldi, "Biotechnology and Biopharmaceuticals: Transforming Proteins and Genes into Drugs"—Chapter 10 summary: "Antibodies and Derivatives," Bitoechnology and Biopharmaceuticals: Transforming Proteins and Genese into Drugs, 2 pages (2003).
Schmid et al., "Sensitive Method for Measuring Apoptosis and Cell Surface Phenotype in Human Thymocytes by Flow Cytometry," *Cytometry*, 15:12-20 (1994).
ClinicalTrials.gov' [online], "Basic Search," 2012 [retrieved Aug. 21, 2013]. Retrieved from the internet http://clinicaltrials.gov/ct2/search, 2 pages.
Almeida et al., "Expression of eight genes of nuclear factor-kappa B pathway in multiple myeloma using bone marrow aspirates obtained at diagnosis," *Histol. Histopathol.*, 24:991-997 (2009).
Chen et al., "Enhancement and destruction of antibody function by somatic mutation: unequal occurrence is controlled by V gene combinatorial associations," *EMBO J.*, 14:2784-2794 (1995).
Excerpt from Immuno Biology: The immune system in health and disease, Third edition, Janeway-Travers, 1997.
Gershoni et al., "Epitope Mapping, The First Step in Developing Epitope-Based Vaccines", Biodrugs vol. 21(3) pp. 145-156 (2007).
Gessner et al "The IgG Fc receptor family", Ann. Hematol. 76: 231-248 (1998).
Gorschluter et al., Clinical Cancer Research 7: 2195-2204 (2001).
Klein et al., "Murine Anti-Interleukin-6 Monoclonal Antibody Therapy for a Patient With Plasma Cell Leukemia", Blood vol. 78(5) 1198-1204 (1991).
Kraj (2000) Immunology Letters 73(2-3), p. 193, Abstract 485.
Li et al., "IMiD immunomodulatory compounds block C/EBPβ translation through eIF4E down-regulation resulting in Inhibition of MM", Blood vol. 117(19) p. 5157-5165, (2011).
Lisignoli et al., "Anti-Fas-Induced Apoptosis in ChondrocytesReduced by Hyaluronan", Arthritis Rheumatism vol. 44(8) pp. 1800-1807 (2011).
Mitsiades et al., "Flow Immunomodulatory are IMiDs?" Blood vol. 117(5) 1440-1441 (2011).
Pisella et al, Invest. Ophthalmol. Vis. Sci., 45(5): 1360-1368 (2004).
Quach et al., Mechanism of action of immunomodulatory drugs (IMiDS) in multiple myeloma. Leukemia. Jan. 2010 ; 24(1): 22-32. doi:10.1038/leu.2009.236. p. 1-2.
Shan et al. "Apoptosis of Malignant Human B Cells by Ligation of CD20 With Monoclonal Antibodies", Blood, 91(5):1644-1652 (1998).
Strom et al., in Therapeutic Immunology, Austen et al. (Ed.) Blackwell Science, Cambridge MA,1996; see pp. 451-456.
Tatsumi (1996) Japanese Journal of Cancer Research 87(8), p. 837-842.
Conrad, et al., "Human antibodies targeting cell surface antigens overexpressed by the hormone refractory metastatic prostate cancer cells: ICAM-1 is a tumor antigen that mediates prostate cancer cell invasion", J. Mol. Med., 87:507-514, 2009.

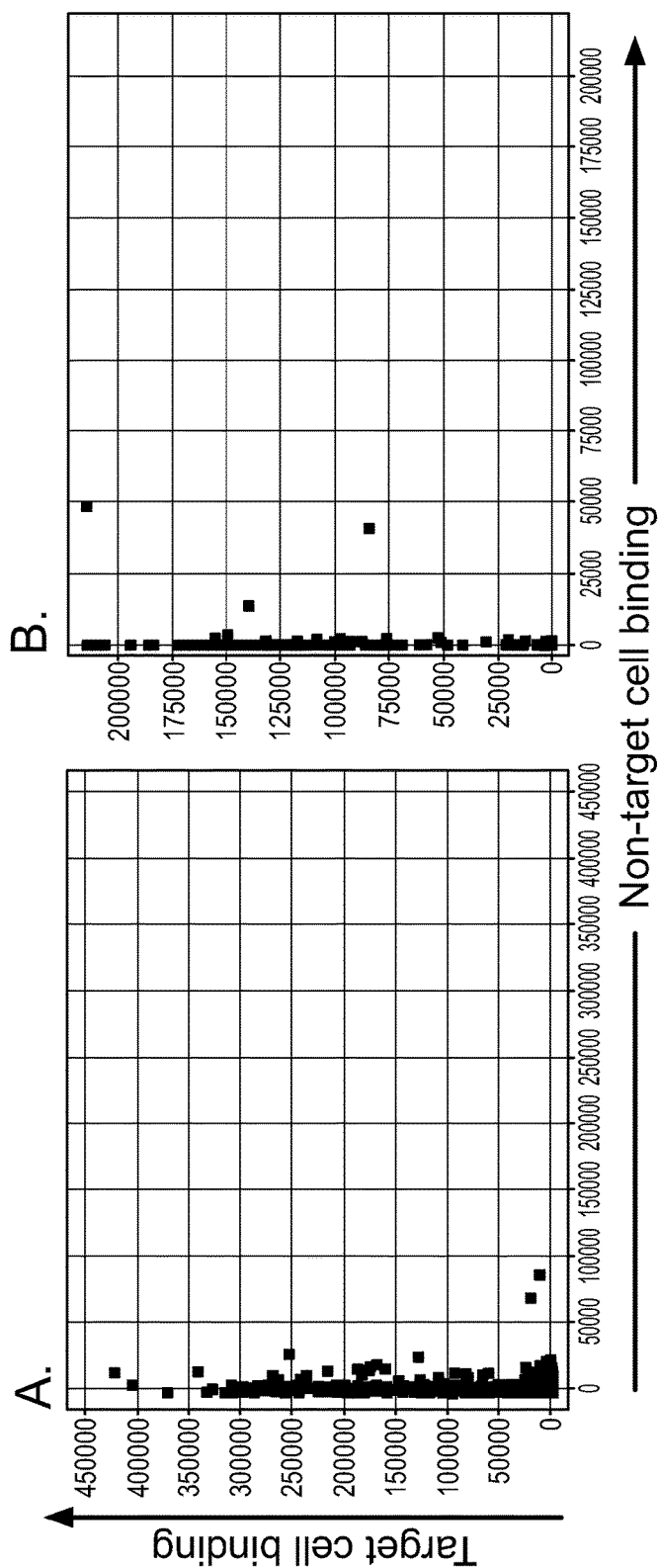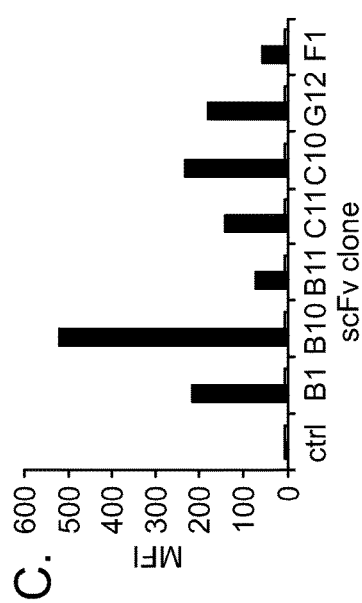
Figure 1

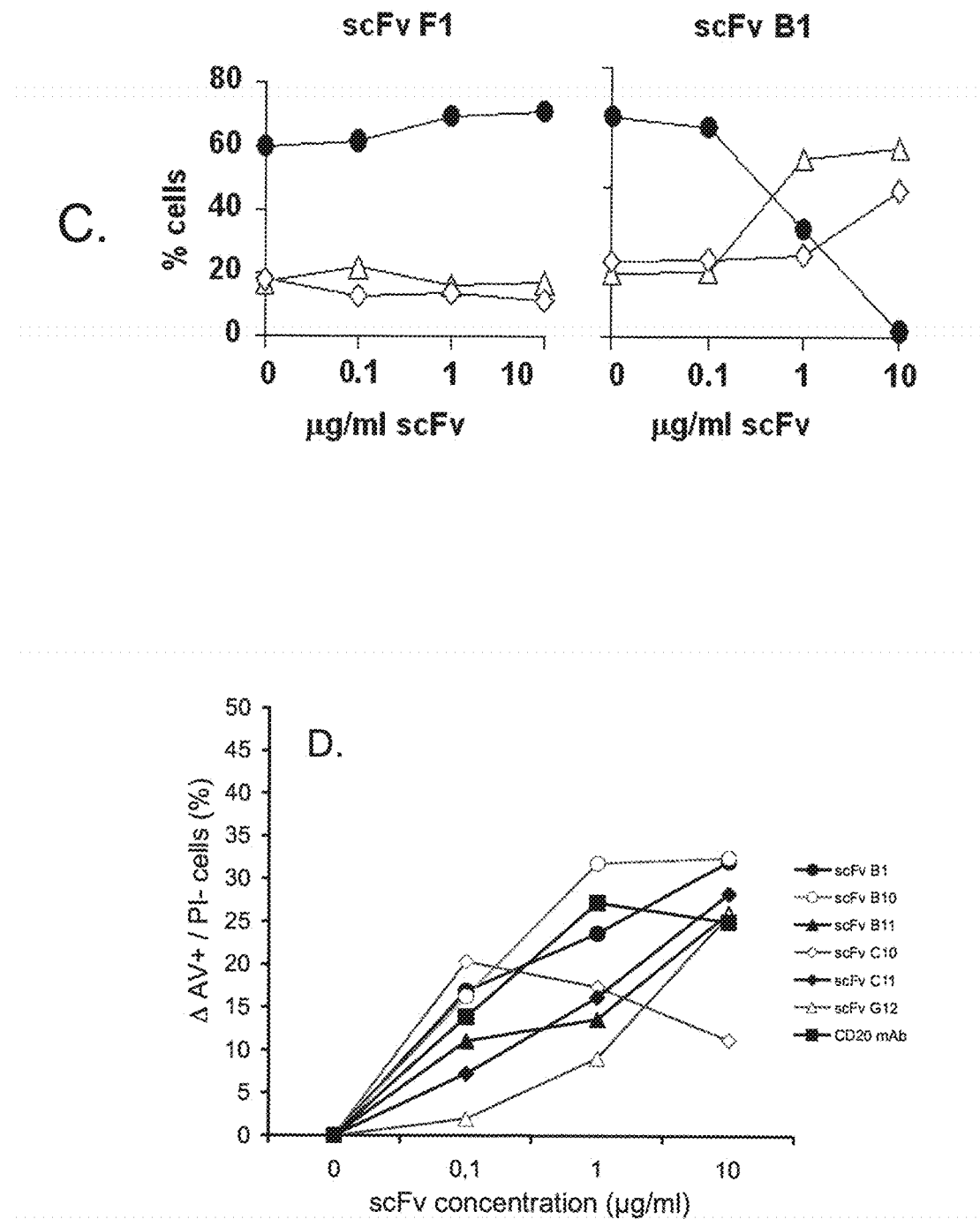
Figure 2 (con't)

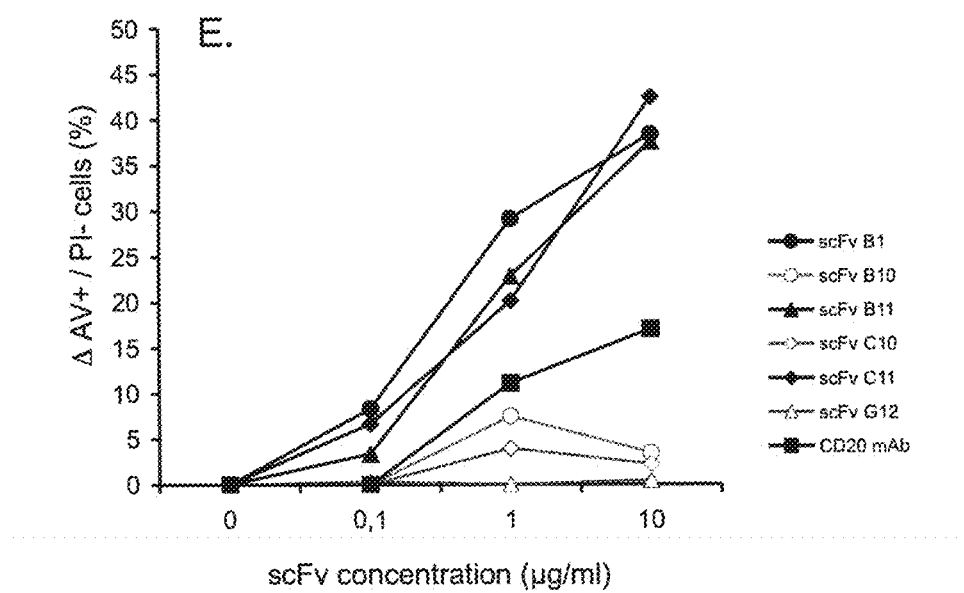
*Figure 2 (con't)*

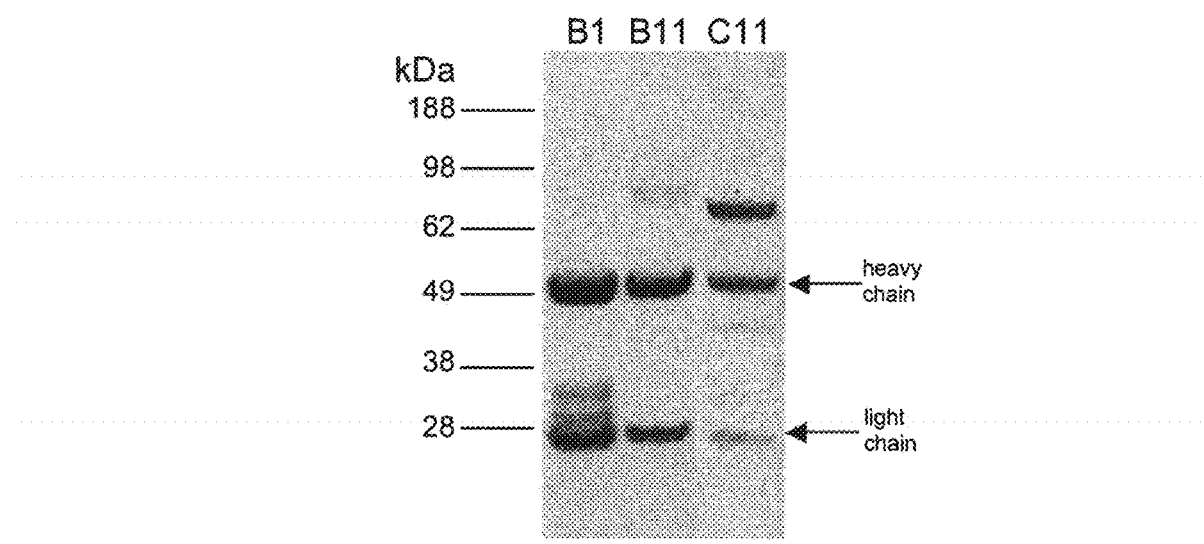
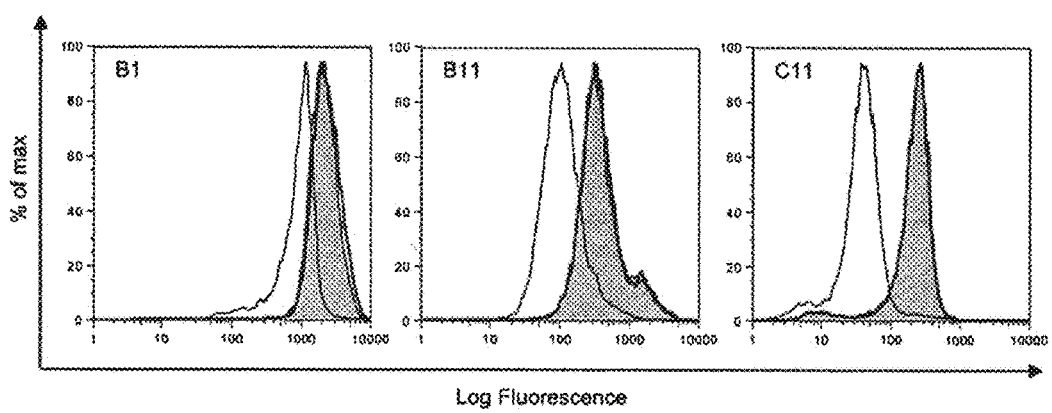
*Figure 3*

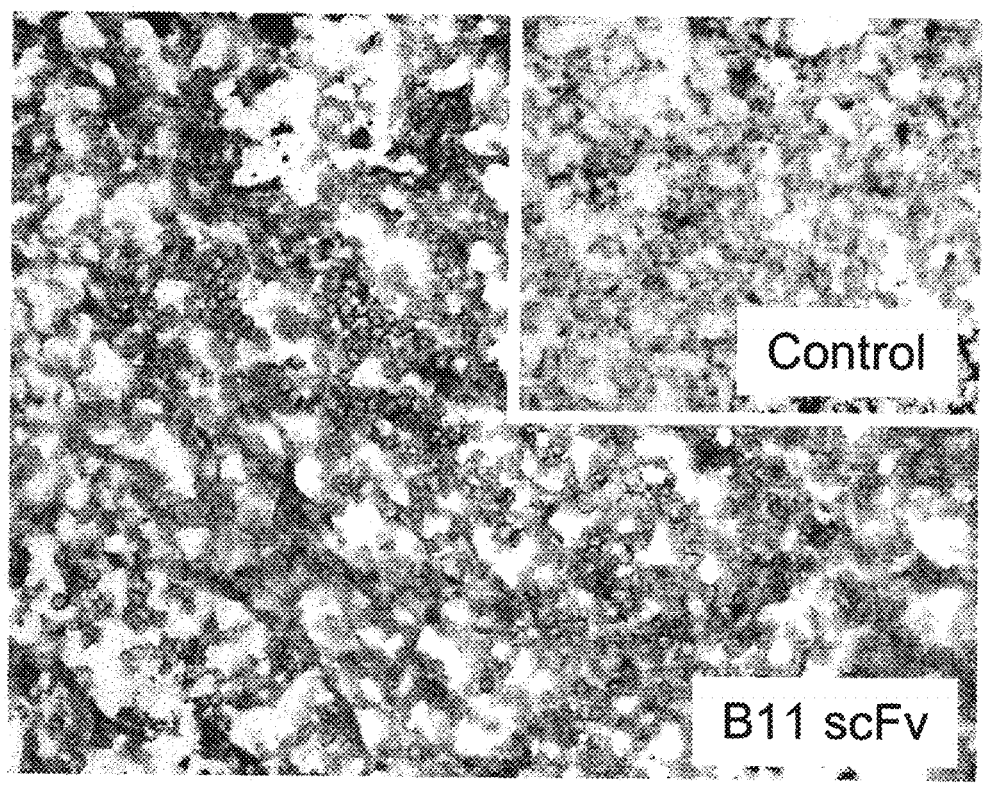
*Figure 4 (con't)*

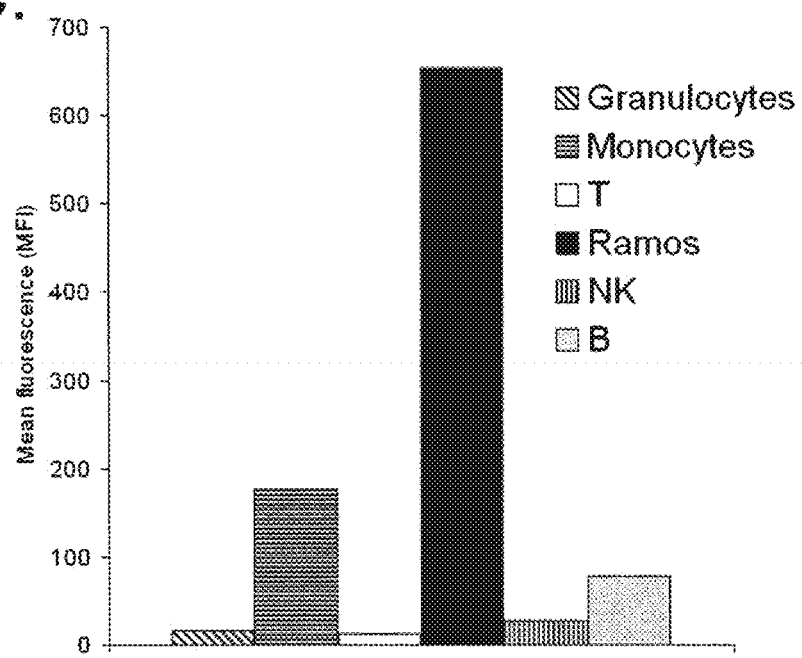
Figure 4 (con't)

A.
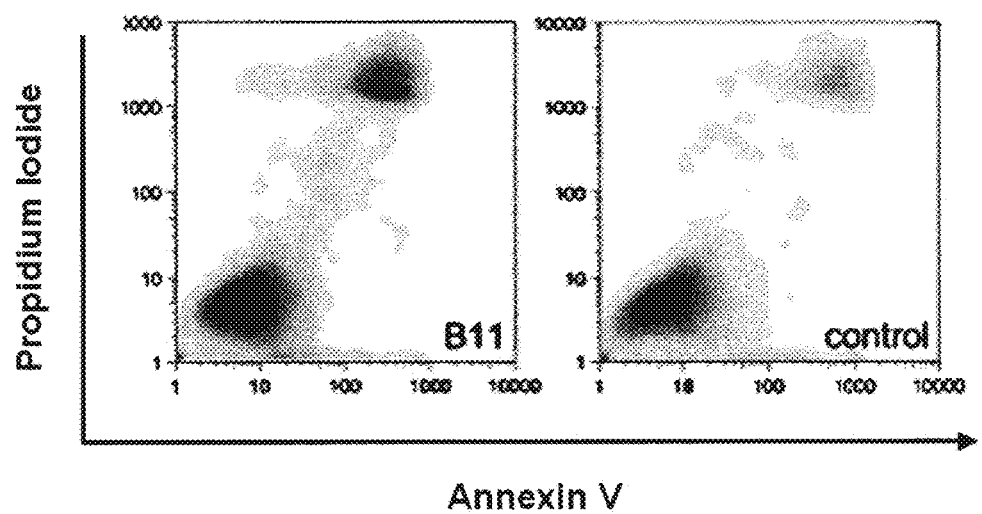
B.
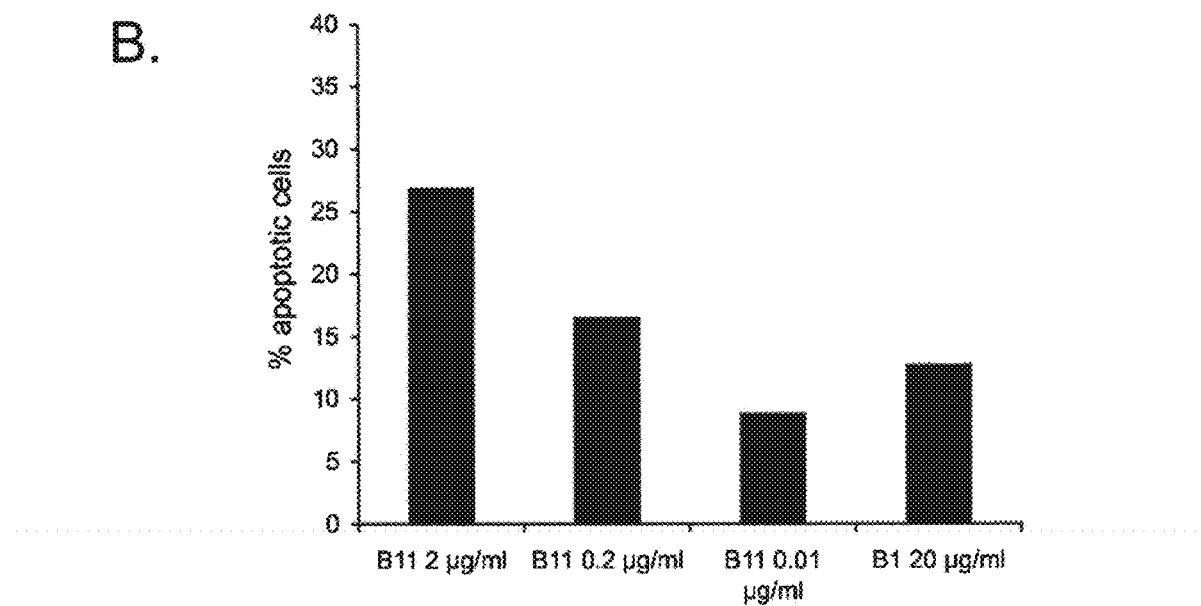
*Figure 7*

C.
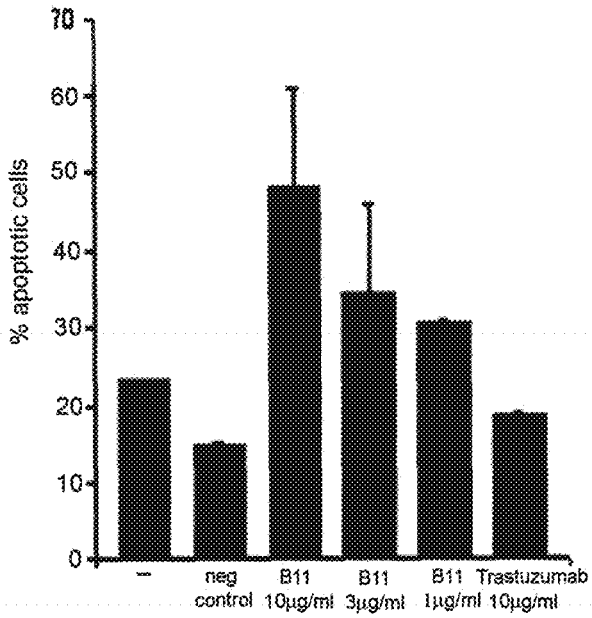
D.
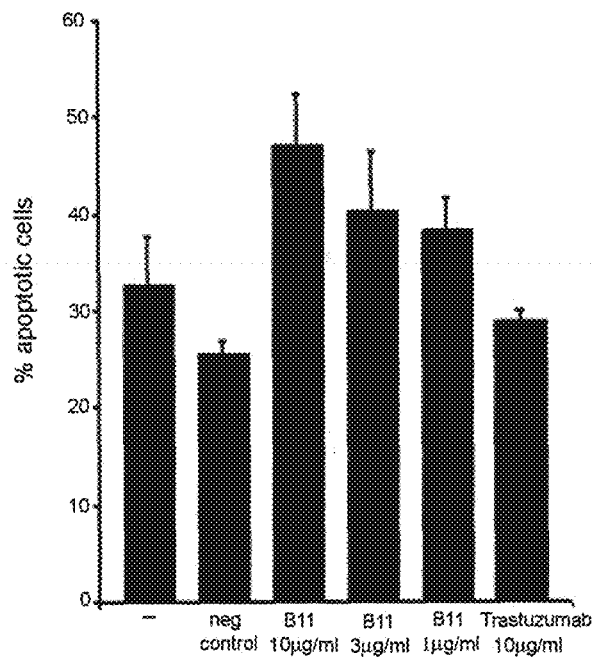
*Figure 7 (con't)*

B1-VH

Nucleotide sequence:

GAGGTGCAGCTGTTGGAGTCTGGGGGAGGCTTGGTACAGCCTGGGGGGTCCCT
GAGACTCTCCTGTGCAGCCTCTGGATTCACCTTTAGCAGCTATGCCATGAGCT
GGGTCCGCCAGGCTCCAGGGAAGGGGCTGGAGTGGGTCTCAGCTATTAGTGGT
AGTGGTGGTAGCACATACTACGCAGACTCCGTGAAGGGCCGGTTCACCATCTC
CAGAGACAATTCCAAGAACACGCTGTATCTGCAAATGAACAGCCTGAGAGCCG
AGGACACTGCCGTGTATTACTGTGCGAGAGATGGGCTACTACCCCTTGACTAC
TGGGGCCAGGGTACACTGGTCACCGTGAGCTCA

Amino acid sequence:

EVQLLESGGGLVQPGGSLRLSCAASGFTFSSYAMSWVRQAPGKGLEWVSAISG
SGGSTYYADSVKGRFTISRDNSKNTLYLQMNSLRAEDTAVYYCARDGLLPLDY
WGQGTLVTVSS

Nucleotide sequence:

CAGTCTGTGCTGACTCAGCCACCCTCAGCGTCTGGGACCCCCGGGCAGAGGGT
CACCATCTCTTGTTCTGGAGGCAGCTCCAACATCGGAGGGAATGCTGTAAATT
GGTATCAGCAGCTCCCAGGAACGGCCCCCAAACTCCTCATCTATGAAAATAAT
AAGCGACCCTCAGGGGTCCCTGACCGATTCTCTGGCTCCAAGTCTGGCACCTC
AGCCTCCCTGGCCATCAGTGGGCTCCGGTCCGAGGATGAGGCTGATTATTACT
GCAGCTCATATGCGGTCAGCAACAATTTCGAGGTGCTATTCGGCGGAGGAACC
AAGCTGACGGTCCTAGGT

Amino acid sequence:

QSVLTQPPSASGTPGQRVTISCSGGSSNIGGNAVNWYQQLPGTAPKLLIYENN
KRPSGVPDRFSGSKSGTSASLAISGLRSEDEADYYCSSYAVSNNFEVLFGGGT
KLTVLG

*Figure 9 (con't)*

B11-VH

Nucleotide sequence:

GAGGTGCAGCTGTTGGAGTCTGGGGGAGGCTTGGTACAGCCTGGGGGGTCCCT
GAGACTCTCCTGTGCAGCCTCTGGATTCACCTTCAGTAACGCCTGGATGAGCT
GGGTCCGCCAGGCTCCAGGGAAGGGGCTGGAGTGGGTGGCATTTATATGGTAT
GATGGAAGTAATAAATACTATGCAGACTCCGTGAAGGGCCGATTCACCATCTC
CAGAGACAATTCCAAGAACACGCTGTATCTGCAAATGAACAGCCTGAGAGCCG
AGGACACTGCCGTGTATTACTGTGCGAGATACAGTGGCTGGTACTTTGACTAC
TGGGGCCAAGGTACACTGGTCACCGTGAGCTCA

Amino acid sequence:

EVQLLESGGGLVQPGGSLRLSCAASGFTFSNAWMSWVRQAPGKGLEWVAFIWY
DGSNKYYADSVKGRFTISRDNSKNTLYLQMNSLRAEDTAVYYCARYSGWYFDY
WGQGTLVTVSS

Nucleotide sequence:

CAGTCTGTGCTGACTCAGCCACCCTCAGCGTCTGGGACCCCCGGGCAGAGGGT
CACCATCTCCTGCACTGGGAGCAGCTCCAACATCGGGGCAGGTTATGATGTAC
ACTGGTATCAGCAGCTCCCAGGAACGGCCCCCAAACTCCTCATCTATGATAAC
AACAATCGGCCCTCAGGGGTCCCTGACCGATTCTCTGGCTCCAAGTCTGGCAC
CTCAGCCTCCCTGGCCATCAGTGGGCTCCGGTCCGAGGATGAGGCTGATTATT
ACTGCCAGTCCTATGACAGCAGCCTCAGTGCTTGGCTGTTCGGCGGAGGAACC
AAGCTGACGGTCCTAGGT

Amino acid sequence:

QSVLTQPPSASGTPGQRVTISCTGSSSNIGAGYDVHWYQQLPGTAPKLLIYDN
NNRPSGVPDRFSGSKSGTSASLAISGLRSEDEADYYCQSYDSSLSAWLFGGGT
KLTVLG

*Figure 10 (con't)*

C11-VH

Nucleotide sequence:

GAGGTGCAGCTGTTGGAGTCTGGGGGAGGCTTGGTACAGCCTGGGGGGTCCCT
GAGACTCTCCTGTGCAGCCTCTGGATTCACCTTCGGCAGTTATGAAATGAACT
GGGTCCGCCAGGCTCCAGGGAAGGGGCTGGAGTGGGTCTCAGTTATTTATAGC
GGTGGTAGCACATACTACGCAGACTCCGTGGAAGGCCGATTCACCATCTCCAG
AGACAATTCCAAGAACACGCTGTATCTGCAAATGAACAGCCTGAGAGCCGAGG
ACACTGCCGTGTATTACTGTGCGAGAGATACAAACCCGTACTACTACGGT
ATGGACGTCTGGGGCCAAGGTACACTGGTCACCGTGAGCTCA

Amino acid sequence:

EVQLLESGGGLVQPGGSLRLSCAASGFTFGSYEMNWVRQAPGKGLEWVSVIYS
GGSTYYADSVEGRFTISRDNSKNTLYLQMNSLRAEDTAVYYCARDTNPYYYG
MDVWGQGTLVTVSS

Nucleotide sequence:

CAGTCTGTGCTGACTCAGCCACCCTCAGCGTCTGGGACCCCCGGGCAGAGGGT
CACCATCTCCTGTTCTGGAAGCAGCTCCAACATCGGAAATAATGCTGTAAACT
GGTATCAGCAGCTCCCAGGAACGGCCCCCAAACTCCTCATCTATAGGAATAAT
CAGCGGCCCTCAGGGGTCCCTGACCGATTCTCTGGCTCCAAGTCTGGCACCTC
AGCCTCCCTGGCCATCAGTGGGCTCCGGTCCGAGGATGAGGCTGATTATTACT
GCCAGTCCTATGACAGCAGCCTGAATGGTCAAGTATTCGGCGGAGGAACCAAG
CTGACAGTCCTAGGT

Amino acid sequence:

QSVLTQPPSASGTPGQRVTISCSGSSSNIGNNAVNWYQQLPGTAPKLLIYRNN
QRPSGVPDRFSGSKSGTSASLAISGLRSEDEADYYCQSYDSSLNGQVFGGGTK
LTVLG

*Figure 11 (con't)*

A
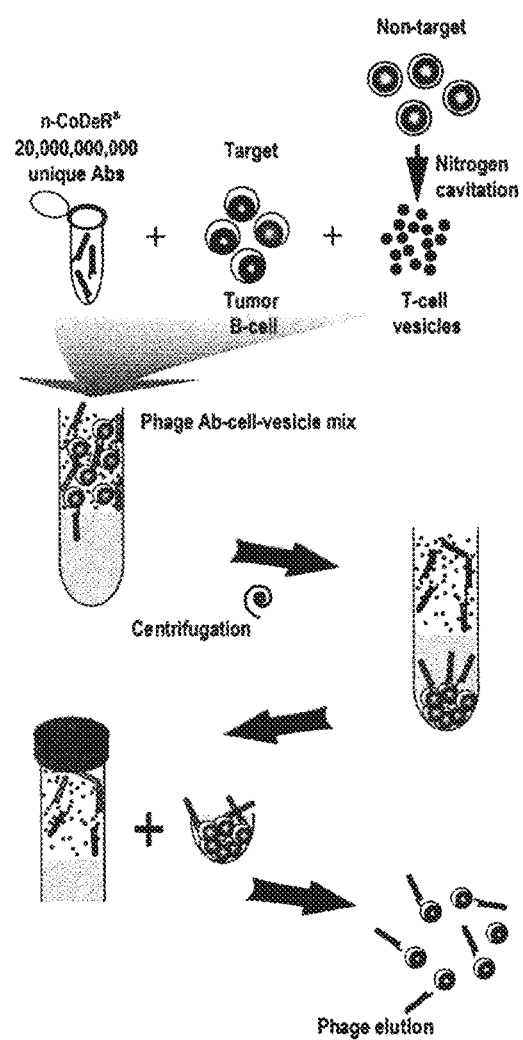
B
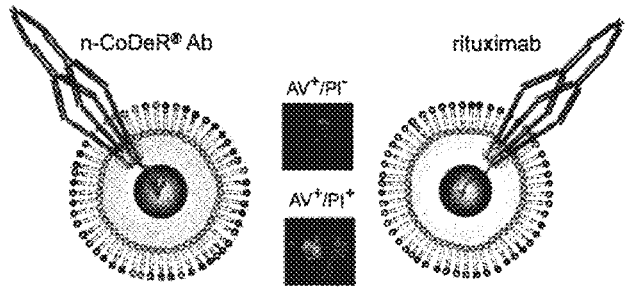
*Figure 12*

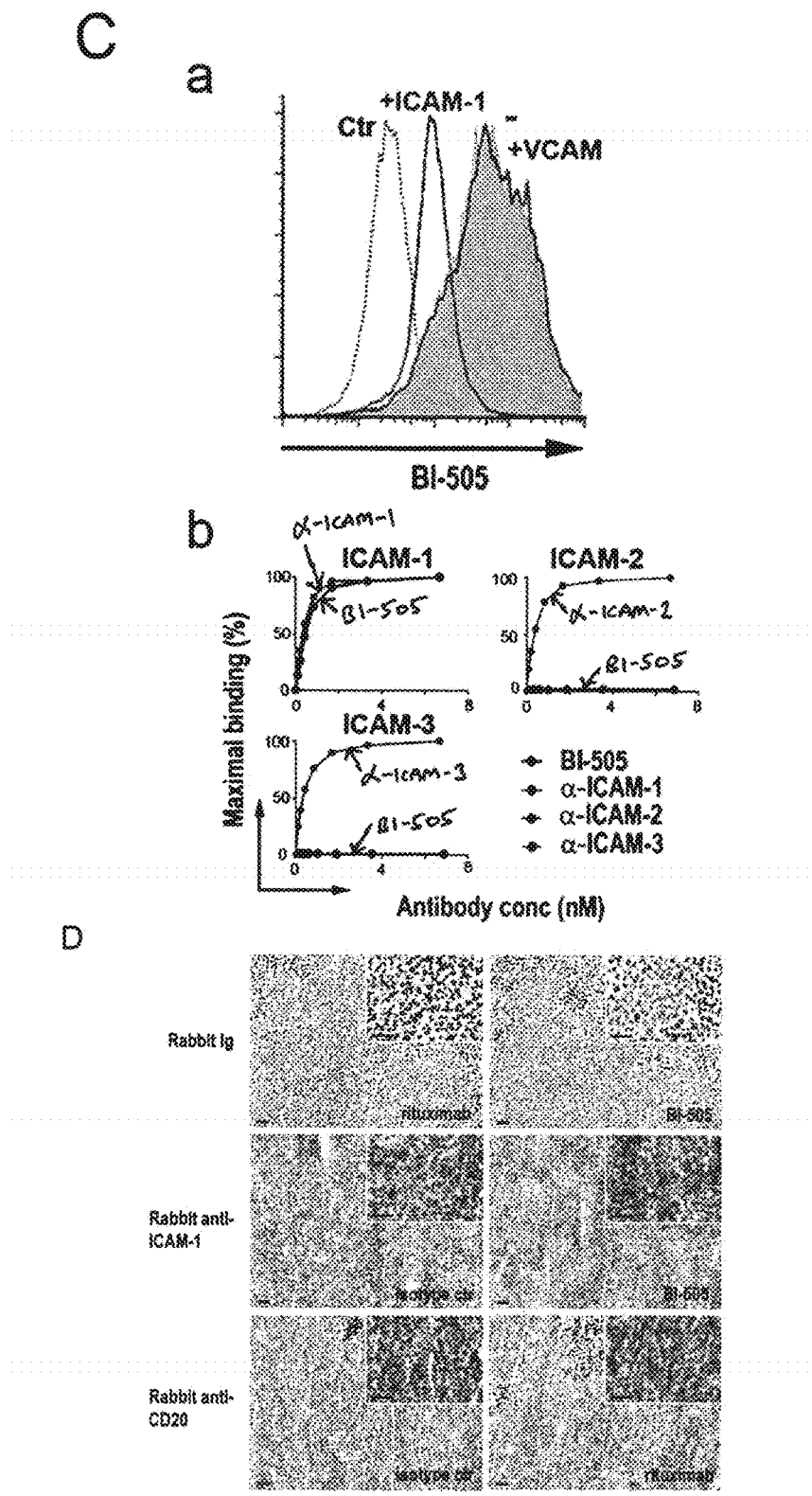
Figure 12 (con't)

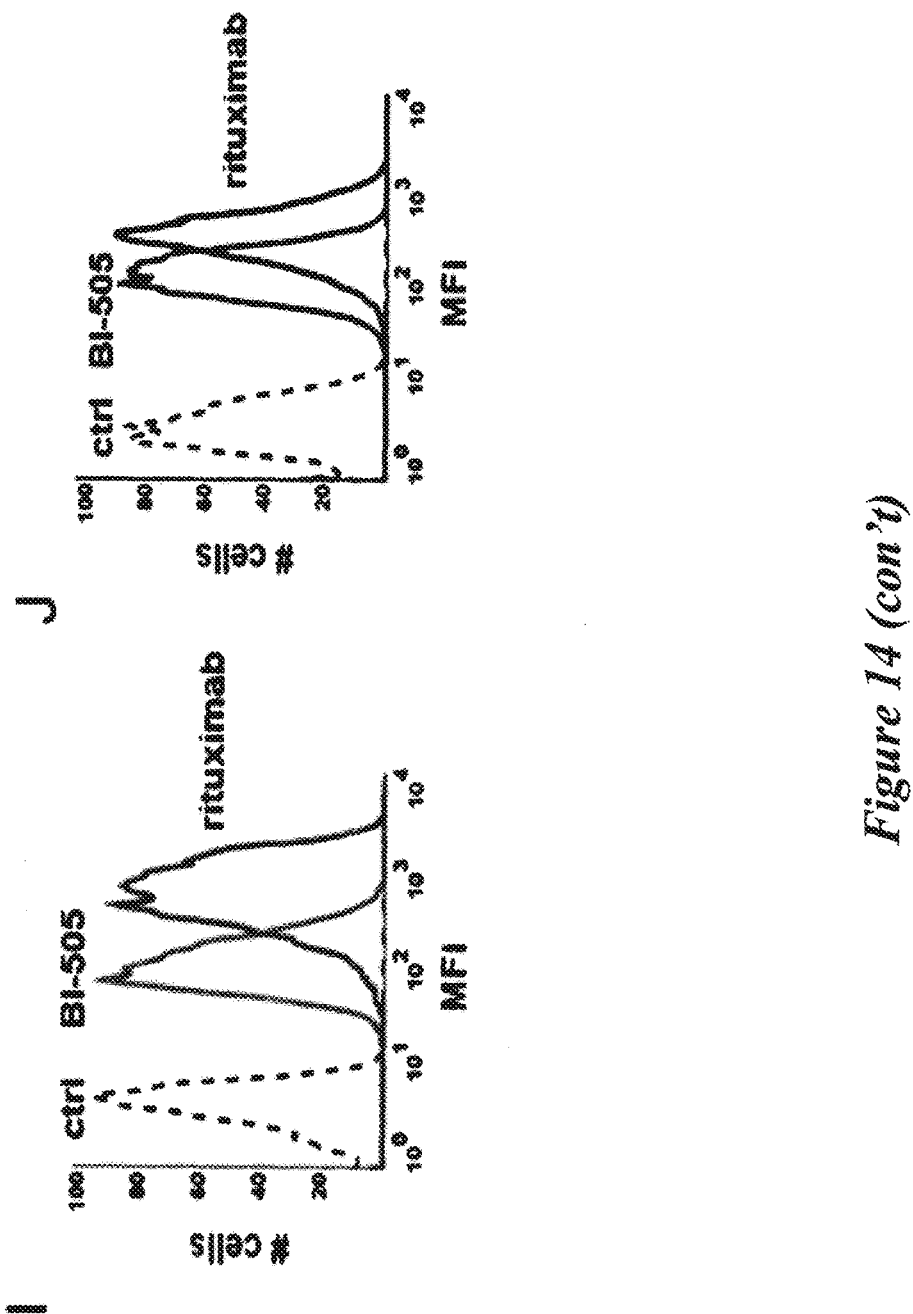
Figure 14 (con't)

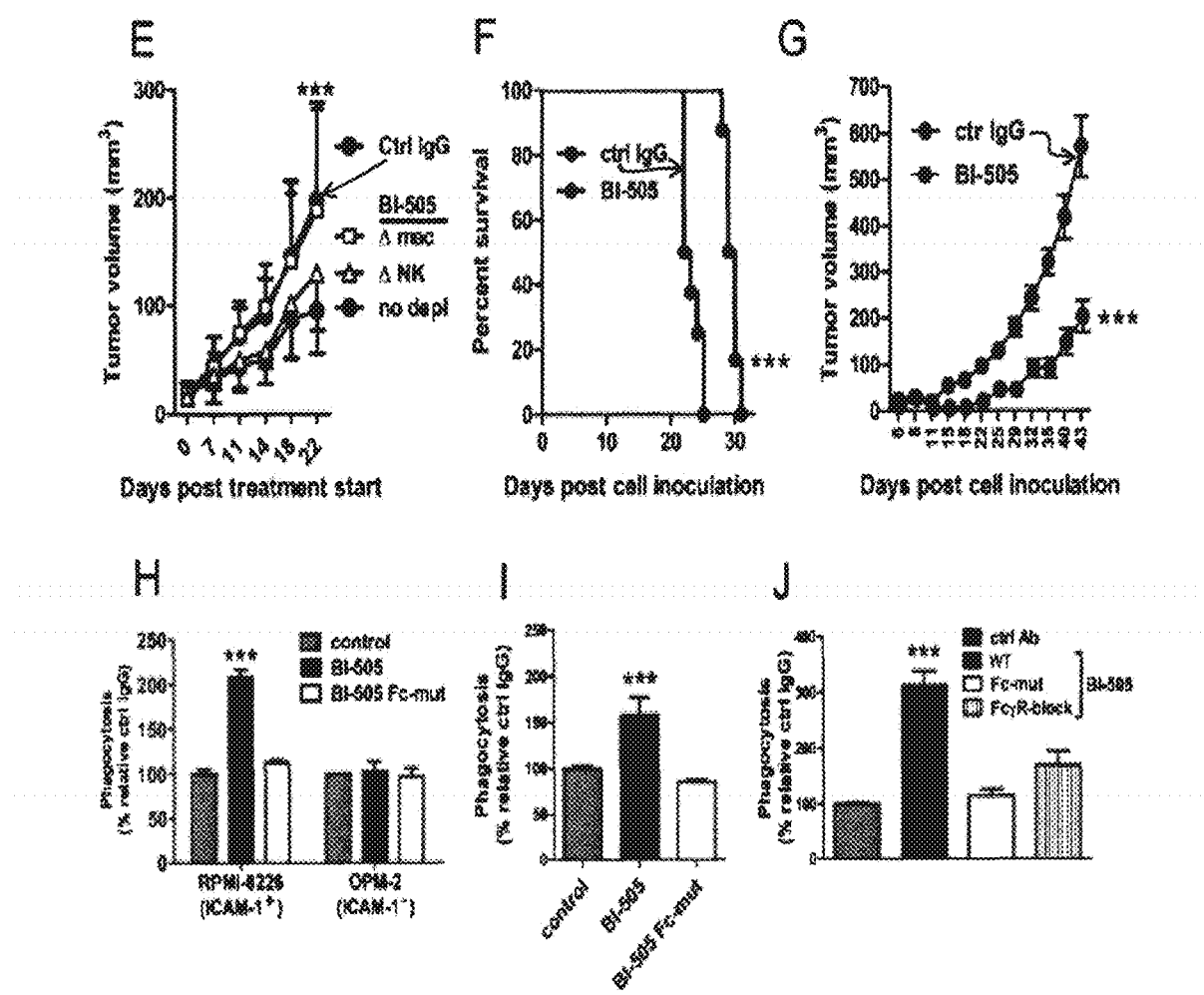
*Figure 20 (con't)*

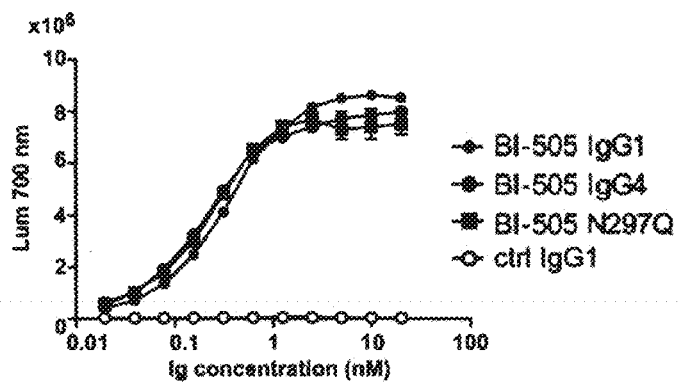
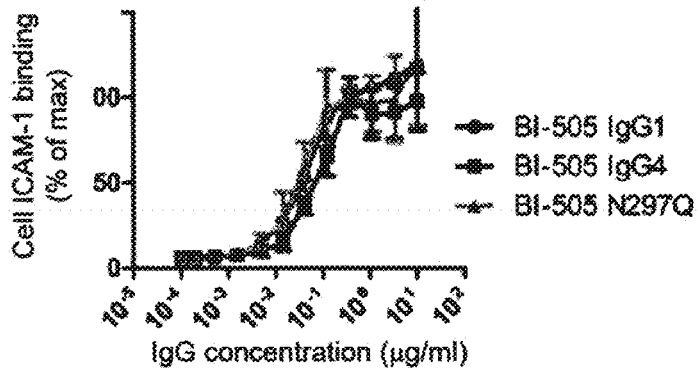
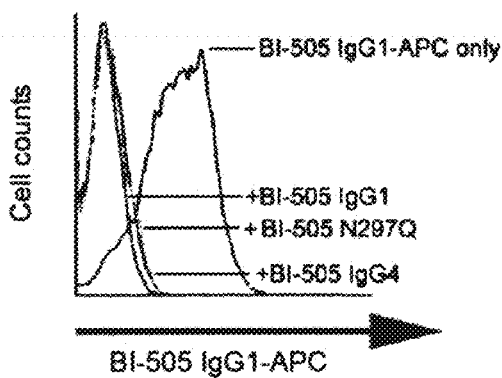
*Figure 21*

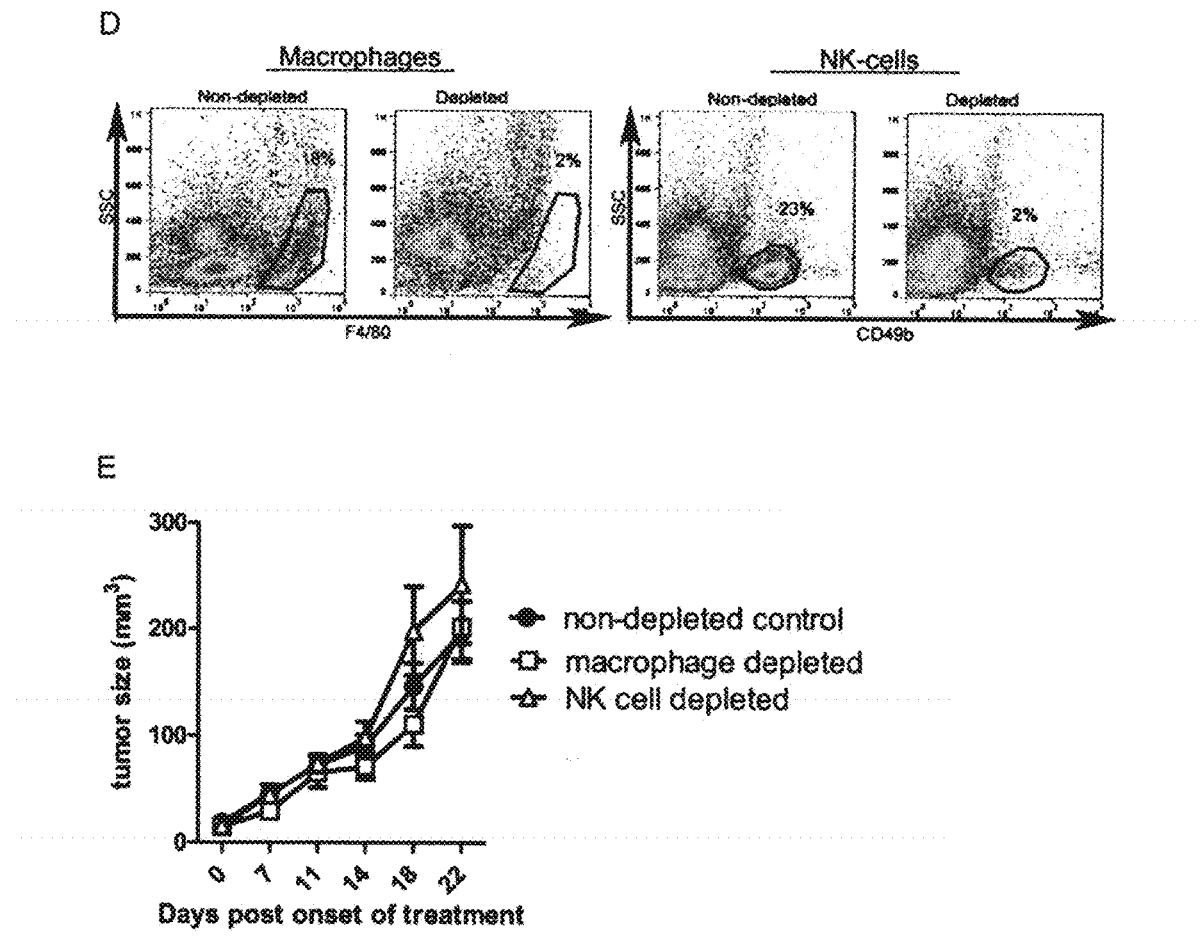
Figure 21 (con't)

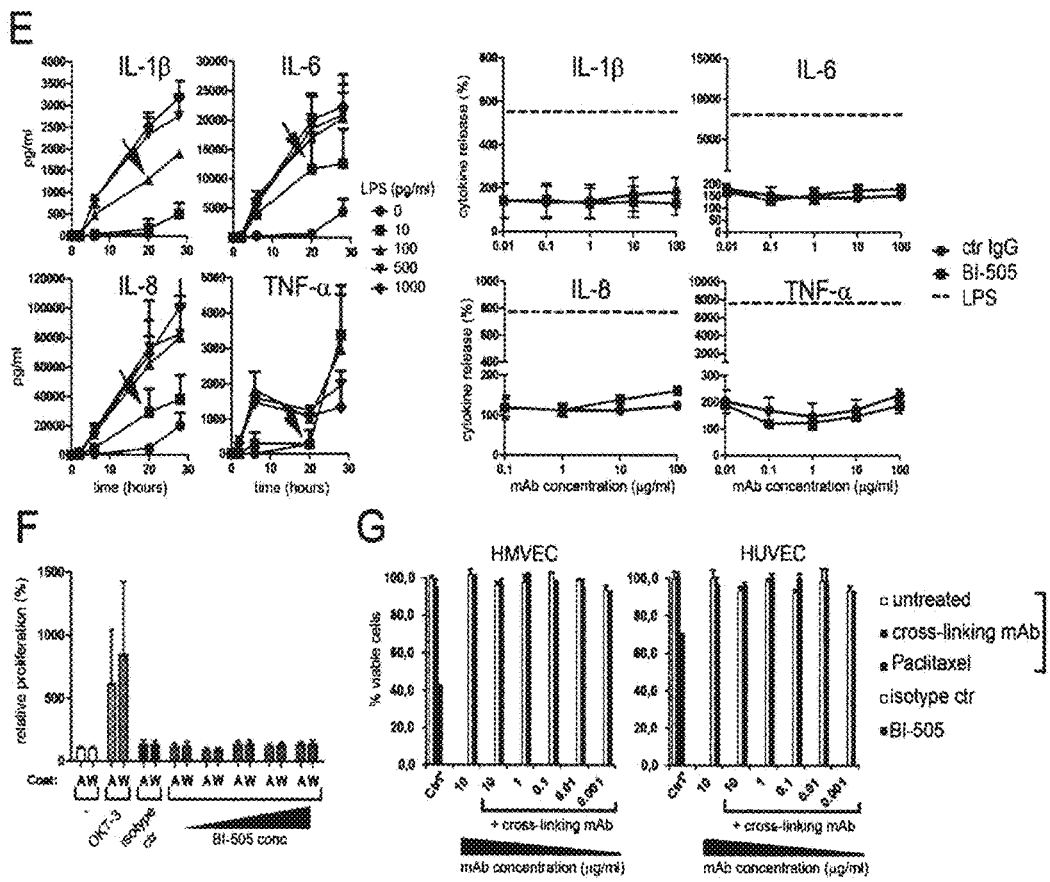
*Figure 23 (con't)*

BIOLOGICAL MATERIALS AND USES THEREOF

REFERENCE TO RELATED APPLICATIONS

This application is a continuation-in-part (CIP) application of U.S. patent application Ser. No. 13/053,846, filed on Mar. 22, 2011 and published as US 2011-0262461 A1; which is a continuation application of U.S. patent application Ser. No. 12/097,193, now U.S. Pat. No. 7,943,744, filed on Oct. 2, 2008 under 35 U.S.C. §371 as a U.S. national stage application of International Application No. PCT/EP2006/012065, filed on Dec. 8, 2006 and published in English as WO2007/068485; which claims priority to U.K. Patent Application No. GB 0525214.3, filed on Dec. 12, 2005, the entire contents of each of the above-referenced applications are incorporated herein by reference.

BACKGROUND OF THE INVENTION

The invention relates to molecules involved in cell death induction, methods and pharmaceutical compositions for cell death induction and uses thereof.

Antibodies have recently become the protein therapeutics of choice for targeting cancer but also for treating other indications (Brekke et al., *Nat. Rev. Drug Discov.* (2003) 2:52-62). The advent of antibody engineering has provided the tools to generate human antibodies from synthetic phage libraries, displaying decreased immunogenicity and enhanced specificity and affinity due to their human nature and greater diversity (Weiner et al., *Nat. Biotechnol.* (2005) 23:556-557). Naïve libraries are particularly attractive, as they may be used for isolation of antibodies for any specificity, including self-antigens (Griffiths et al., *Embo. J.* (1993) 12:725-734), independent of immunizations and reconstruction of new libraries. Cell surface receptors constitute by far the most successful group of antigens targeted by contemporary therapeutic drugs, including small molecule inhibitors and antibodies. Of particular interest are cell surface receptors that are uniquely expressed or that display an increased expression level on a target cell and are additionally capable of relaying death or survival signals to the cell. Such differentially expressed receptors with intrinsic signalling properties enable antibody-based targeting of microbial infected, transformed, or otherwise malfunctioning cells.

For treatment of tumours, antibodies that have the ability to induce cell death in a target tumour cell whilst sparing normal tissue are of particular interest. Several such antibodies are in use, have been registered with the US Food and Drug Administration (FDA) and provide alternatives to conventional cancer treatments e.g. for lymphoma (rituximab targeting CD20) or for breast cancer (trastuzumab or cetuximab targeting Her-2 and EGFR respectively).

There are also other antibodies with cell death inducing effects currently in clinical development. However, even if these antibodies demonstrate beneficial effects in patients or in animal tests an unmet clinical need still exists.

Anti-idiotypic immunoglobulin targeting of B cell tumours was the first monoclonal antibody therapy conducted in man (Miller et al. *N. Engl. J. Med.* (1982) 306:517-522). Destruction of tumour cells by such means of passive antibody administration (Riechmann et al., *Nature* (1988) 332:323-327), or active vaccination with the patient's own tumour immunoglobulin protein (Kwak et al. *N. Engl. J. Med.* (1992) 327:1209-1215), has since been demonstrated to confer tumour regression or tumour dormancy in patients with different kinds of B cell malignancies. A more recent report describes the generation of fully human anti-idiotype antibodies using transgenic mice deficient in mouse antibody production and expressing selected human antibody chain loci (Suarez et al. *Mol. Immunol.* (2004) 41:519-526).

In the present invention a competition biopanning method has been used, where target cell antigen in the form of whole cells, and excess subtractor cell antigen in the form of membrane vesicles, are exposed at the same time to the naïve n-CoDeR® antibody phage library (WO 2004/023140; Soderlind et al., *Nat. Biotechnol.* (2000) 18:852-856), to retrieve and subsequently test antibody fragments with excellent selectivity for B lymphoma target cells. Furthermore, functionality in the selected binding molecules was demonstrated by the ability of the antibodies tested to induce cell death in target but not in non-target cells.

Antibody specificities identified include ICAM-1 (the B11 antibody of the invention (also referred to as BI-505)) which is an adhesion molecule. Isolated antibodies had affinities in the sub-nanomolar to nanomolar range, directly making them possible choices for targeted antibody therapy.

ICAM 1 is highly expressed in several human malignancies and is believed to be involved in their pathogenesis (Aalinkeel et al., 2004; Hideshima et al., 2007; Huang et al., 1995; Johnson et al., 1988; Schmidmaier et al., 2006). Notably, ICAM-1 was recently reported to be over-expressed and associated with advanced disease and poor survival in multiple myeloma (MM) (Sampaio et al., 2009; Schmidmaier et al., 2006). Further, evidence suggests that ICAM-1 is upregulated and casually related to MM patient development of resistance to chemotherapy (Sampaio et al., 2009; Schmidmaier et al., 2006; Zheng et al., 2009). ICAM-1, by binding to integrin β2 receptors and muc 1, is involved in cell-adhesive events that trigger multiple cell-signaling pathways promoting MM cell proliferation, migration, resistance to apoptosis, and development of cell adhesion molecule-induced drug-resistance (Hideshima et al., 2007; Schmidmaier et al., 2004; Zheng et al., 2009). There is no curative treatment for MM and the currently available therapy is associated with significant toxicity and development of drug resistance (Kyle and Rajkumar, 2004). MM plasma cells typically do not express the B cell antigen CD20, or show low and heterogeneous CD20 expression, making CD20 targeted therapies ineffective in this disease (Kapoor et al., 2008; Richardson et al., 2011).

The inventors have now characterized MM plasma cells for expression of the ICAM-1 epitope targeted by their function-first isolated antibody BI-505, and demonstrate BI-505's therapeutic activity and mechanism-of-action in well-established experimental models of MM.

SUMMARY OF THE INVENTION

In a first aspect of the invention there is provided an in vivo method of inducing Fc-FcγR-dependent cell death in a target cell comprising the steps:
a. providing one or more target cells displaying the cell surface antigen, ICAM-1;
b. providing one or more binding molecules which selectively binds to cell surface ICAM-1 and, on binding ICAM-1, induces Fc-FcγR-dependent cell death of the target cell;
c. exposing the target cells of (a) to the binding molecules of (b) to induce Fc-FcγR-dependent cell death of the target cells.

By Fc-FcγR-dependent cell death we include any cell death which relies on interaction between the Fc region of the binding molecule and the FcγR receptor of an FcγR-expressing cell or cells. Examples of FcγR-expressing cells include macrophages and Natural Killer (NK) cells. Preferably the FcγR-expressing cell is a macrophage.

Preferably the binding molecule is an antibody molecule.

In a second aspect of the invention there is provided a binding molecule which selectively binds to cell surface ICAM-1 and, on binding ICAM-1, induces Fc-FcγR-dependent cell death of a target cell in vivo.

In a third aspect of the invention the binding molecule of the second aspect is for use in the method of the first aspect.

In certain embodiments the cell death described in the first, second or third aspects may be independent of the process apoptosis. In some embodiments the binding molecule described in the first, second or third aspects may additionally induce apoptosis of the target cell in vitro and/or in vivo.

In preferred embodiments the Fc-FcγR-dependent cell death is mediated by macrophages (macrophage-dependent cell death). Macrophages are well known immune cells which are capable of causing destruction of cells (e.g. cancer cells). For example, this may be achieved by the process of phagocytosis. This process is also referred to as Fc-FcγR-dependent macrophage phagocytosis (antibody dependent cell phagocytosis (ADCP)) and is distinct from antibody dependent cell cytotoxicity (ADCC) resulting from NK cells. Both processes are also distinct from cell death arising due to apoptosis (programmed cell death (PCD)). These distinct processes have long been known in the art, see for example Medical Microbiology & Immunology 4$^{th}$ Edition Chapter 58, Levinson and Jawetz (Appleton & Lance 1996).

ICAM-I is also designated CD54, but for the purpose of this application ICAM-1 will be used.

Binding molecules may be derived from antibodies and based on the antibody scaffold [Clackson, T et al., *Nature*, (1991) August 15, 352(6336):624-628; Marks, J D et al., *J. Mol. Biol.* (1991) December 5, 222(3):581-597] that has been used extensively in many libraries, but binding molecules may also be derived form other molecular scaffolds such as the fibronectin scaffold [Weng, S et al., *Proteomics* (2002) January, 2(1):48-57] and the protein A scaffold [Nord, K, et al., *Nat. Biotechnol.* (1997) August, 15(8):772-777; Hogbom, M et al., *Proc. Natl. Acad. Sci. USA*. (2003) March 18, 100(6):3191-3196]. Each of these scaffolds may have their advantages depending on application, and the antibody scaffold, as one example, may be used advantageously for creating variability indistinguishable from natural variability.

The basic structure of the antibody, the most commonly used scaffold, is very well understood. In principle, a framework structure comprising beta strands ordered into two sheets present a set of variable loops, the so called Complementary Determining Regions (CDRs) that have the capacity to bind to antigen molecules. Although antibodies may vary in the scaffold structure the most extensive variability is seen in the CDRs. The great variability in-between antibodies, is the basis for their ability to interact, in a specific manner, with in principle all types of molecular structures. Due to this capacity, antibodies have been used extensively for generation of specific binders with applicability within research, diagnosis/prognosis of disease and as therapeutic agents specific for defined target structures [Borrebaeck, C A and Carlsson, R, *Curr. Opin. Pharmacol.* (2001) August, 1(4):404-408].

Other, non-antibody binding molecules useful in this invention are those having scaffold structures with a high degree of stability yet allowing variability to be introduced at certain positions. An example of another binding molecule is a fibronectin domain and a 58 amino acids large protein A domain which tolerate variability. There are also other molecular folds that allow some degree of variation. Such examples include major histocompatibility complex (MHC) class I and II molecules and recently a novel class of molecules the so called defensins have been identified to be similar in basic structure while still harbouring extensive sequence variability in-between the gene family members indicating that they are suitable as scaffolds for harbouring molecular diversity. In addition, natural ligand(s) e.g. LFA-1 in the case of ICAM-1 as a target molecule, or recombinant variants of them, may constitute specific binding molecules able to induce cell death in target cells.

Furthermore, the binding molecule may be any molecule selectively binding cell surface ICAM-1 of a target cell and, on binding, inducing Fc-FcγR-dependent cell death of the target cell.

The binding molecule is preferably an antibody molecule.

In one embodiment the cell surface antigen is ICAM-1.

The present screening retrieved an antibody (B11/BI-505) specific for ICAM-1.

The identification of ICAM-1 as a cell death-inducing molecule was a direct result of the screening being designed to isolate specificities for all surface receptors differentially expressed between target and non-target cells, irrespective of and without prior knowledge of their respective identity. ICAM-1-induced cell death has been verified as an active apoptotic process that involved mitochondrial membrane depolarisation. Mitochondrial membrane depolarisation has been previously described for both caspase dependent and caspase independent apoptosis (Nagy et al., *J. Mol. Med.* (2003) 81:757-765).

The present findings further show that the epitope bound by the B11 antibody is expressed in B lymphoma tissue of different origin, and is up regulated in certain B lymphoma cells compared to resting peripheral blood leukocytes. Importantly, in addition to B lymphoma cells also carcinoma cells expressing ICAM-1 underwent apoptosis when subjected to the ICAM-1 specific B11 antibody in vitro (see Example 6).

Previous studies have demonstrated restricted expression of ICAM-1 on normal human tissues (Smith et al., *J. Clin. Pathol.* (1990) 43:893-900). ICAM-1 is involved in cell to cell adhesion and plays an important role in immune responses and inflammation through binding to its receptor LFA-1. Antibodies directed to ICAM-1 have been used to interfere with pathological immune responses and inflammation. In vivo administration of a murine anti-ICAM-1 mAb in cymologous monkeys (Cosimi et al., *J. Immunol.* (1990) 144:4604-4612), or use in clinical trials in human patients with rheumatoid arthritis or patients receiving kidney transplants has also revealed no overt toxicity (Kavanaugh et al., *Arthritis Rheum.* (1994) 37:992-999; Haug et al., *Transplantation* (1993) 55:766-772).

The finding that ICAM-1 targeting can lead to cell death demonstrates the possibility to use ICAM-1 specific binding molecules, such as antibodies for treatment of cancers of different origins provided that they express the antigen.

Based on their expression of ICAM-1 cancer types that may potentially be treated with a cell death inducing anti-ICAM-1 antibody such as B11 include: B lymphoma, myeloma (Huang et al. (1993) *Hybridoma*, 12:661-675; Huang et al. (1995) *Cancer Res.*, 55:610-616; Smallshaw et al., (2004) *J. Immunother.,* 27:419-424), gastric cancer (Maruo et al., (2002) *Int. J. Cancer,* 100:486-490), breast cancer (Rosette et al., (2005) *Carcinogenesis* 26:943-950), liver cancer (Sun et al., (1999) *J. Cancer Res. Clin. Oncot,* 125:28-34), lung cancer (Grothey et al., (1998) *Br. J. Cancer,* 77:801-807), melanoma (Wang et al., (2005) *Int. J. Cancer,* 27:419-424), bladder cancer (Roche et al., (2003) *Thromb. Haemost.,* 89:1089-1097) and prostate cancer (Aalinkeel et al., (2004) *Cancer Res.,* 64:5311-5321). Expression of ICAM-1 has also been identified in tumour metastasis as demonstrated by (Maruo et al., 2002), (Rosette et al., 2005), (Sun et al., 1999), (Grothey et al., 1998), (Aalinkeel et al., 2004) pointing to the possibility to intervene in metastasis processes using an ICAM-1 specific antibody.

The kinetics of B11 IgG induced apoptosis were fast, with maximal efficacy being observed already after 3 hours in some cell lines. Rapid effector function is important for therapeutic efficacy as this minimizes the risk for tumour evasion resulting from e.g. lack of expression of tumour antigen (Uyttenhove et al., *J. Exp. Med.* (1983) 157:1040-1052; Kennedy et al., *Br. J. Haematol.* (2002) 119:412-416) or epitope mutation (Weiner et al., *J. Immunol.* (1989) 142:343-351; Bai et al., *J. Clin. Invest.* (2003) 111:1487-1496), and potentially limits treatment duration and side-effects (Robert et al., *Lancet Oncol.* (2005) 6:491-500).

Preferably the target cell is an immune cell or epithelial cell and advantageously that immune cell is a B lymphocyte.

Conveniently the target cell is associated with a disease. Preferably the disease is selected from the group consisting of: cancer; autoimmune diseases including but not restricted to rheumatoid arthritis and SLE, acute and chronic inflammatory disorders, sepsis and infectious disease including but not restricted to HIV.

Advantageously, the disease is a cancer selected from lymphoma (leukaemia, myeloma), gastric cancer, breast cancer, liver cancer, lung cancer, melanoma, bladder cancer, choroid cancer, pancreatic cancer, colon cancer and prostate cancer.

As defined in the definitions section of this application, the phrase antibody molecule is used for convenience and embraces, amongst other things, antibodies, an antibody fragments, and antibody derivatives.

Conveniently, the antibody molecule is an IgG. The IgG may be any of $IgG_1$, $IgG_2$, $IgG_3$ or $IgG_4$, but preferably any of $IgG_1$ and $IgG_4$. The antibody molecule is preferably humanised or human.

Conveniently, the binding molecule or antibody molecule of the invention has the sequence of any one of variable region sequences of FIG. 10 or functionally equivalent homologues thereof.

In an embodiment of the invention, the binding molecule or antibody molecule has the variable region sequences of FIG. 10 or functionally equivalent homologues thereof.

In a fourth aspect of the invention there is provided a nucleic acid having a nucleotide sequence encoding a binding molecule or an antibody molecule as described in any previous aspect.

Conveniently the nucleic acid has the nucleotide sequence of any FIG. 10.

In a fifth aspect of the invention there is provided use of the binding molecule or antibody molecule as defined in the first or second aspect of the invention in the diagnosis and/or treatment and/or prevention of a disease requiring the destruction of a target cell. There is also provided the use of the binding molecule or antibody molecule as defined in the first or second aspect of the invention in the manufacture of a medicament for the treatment and/or prevention of a disease requiring the destruction of a target cell.

In a preferred embodiment the binding molecule is an antibody molecule.

Conveniently, the disease to be treated is selected from the group consisting of: cancer; autoimmune diseases including but not restricted to rheumatoid arthritis and SLE, acute and chronic inflammatory disorders, sepsis and infectious disease including but not restricted to HIV.

Advantageously the disease to be treated is cancer selected from lymphoma (leukaemia, myeloma), gastric cancer, breast cancer, liver cancer, lung cancer, melanoma, bladder cancer, choroid cancer, pancreatic cancer, colon cancer and prostate cancer.

In one embodiment of the invention the binding molecule or antibody molecule binds specifically to ICAM-1 and/or has the sequence of FIG. 10 and is used in relation to the diseases listed above.

In a sixth aspect of the invention there is provided a pharmaceutical composition comprising the binding molecule or antibody molecule of the invention and a pharmaceutically acceptable carrier, excipient or diluent.

In a preferred embodiment the binding molecule is an antibody molecule.

In a seventh aspect of the invention there is provided an in vivo method of inducing Fc-FcγR-dependent cell death of a target cell comprising the steps of:
(i) providing one or more target cells;
(ii) providing one or more binding molecules or antibody molecules as defined in the first embodiment of the invention;
(iii) exposing the target cells of (i) to the binding molecules or antibody molecules of (ii) so as to induce Fc-FcγR-dependent cell death of the target cells.

In a preferred embodiment the binding molecule is an antibody molecule.

Preferably the target cells provided in step (i) are immune cells or epithelial cells. Advantageously, the immune cells are B lymphocytes.

Conveniently, the target cells are associated with a disease and wherein the disease is selected from the group consisting of: cancer; autoimmune diseases including but not restricted to rheumatoid arthritis and SLE, acute and chronic inflammatory disorders, sepsis and infectious disease including but not restricted to HIV.

Advantageously, the disease is a cancer selected from lymphoma (leukaemia, myeloma), gastric cancer, breast cancer, liver cancer, lung cancer, melanoma, bladder cancer, choroid cancer, pancreatic cancer, colon cancer and prostate cancer.

BRIEF DESCRIPTION OF THE DRAWINGS

FIG. 1—scFv isolated by differential whole cell/cell membrane vesicle biopanning show high target cell specificity.

scFv clones isolated by differential biopanning were expressed in *E. coli* TOP10 cells and incubated with Ramos or Jurkat cells and (FIG. 1A) scFv clones expressed for primary screening or (FIG. 1B) seventy two randomly picked and re-expressed scFv clones. Bound scFv was detected with anti-His MAb, and Cy5-anti-mouse polyclonal Ab. Cell binding was detected in an FMAT Macroconfocal High Throughput Screening instrument. Cell binding is depicted as mean fluorescence intensity to target Ramos cells (Y axis) vs. non-target Jurkat cells (X-axis). (FIG. 1C)

Binding of seven unique scFv clones to Ramos cells (filled bars) and Jurkat cells (open bars). A control scFv (ctrl) did not bind to any of the cells.

Figure 2:
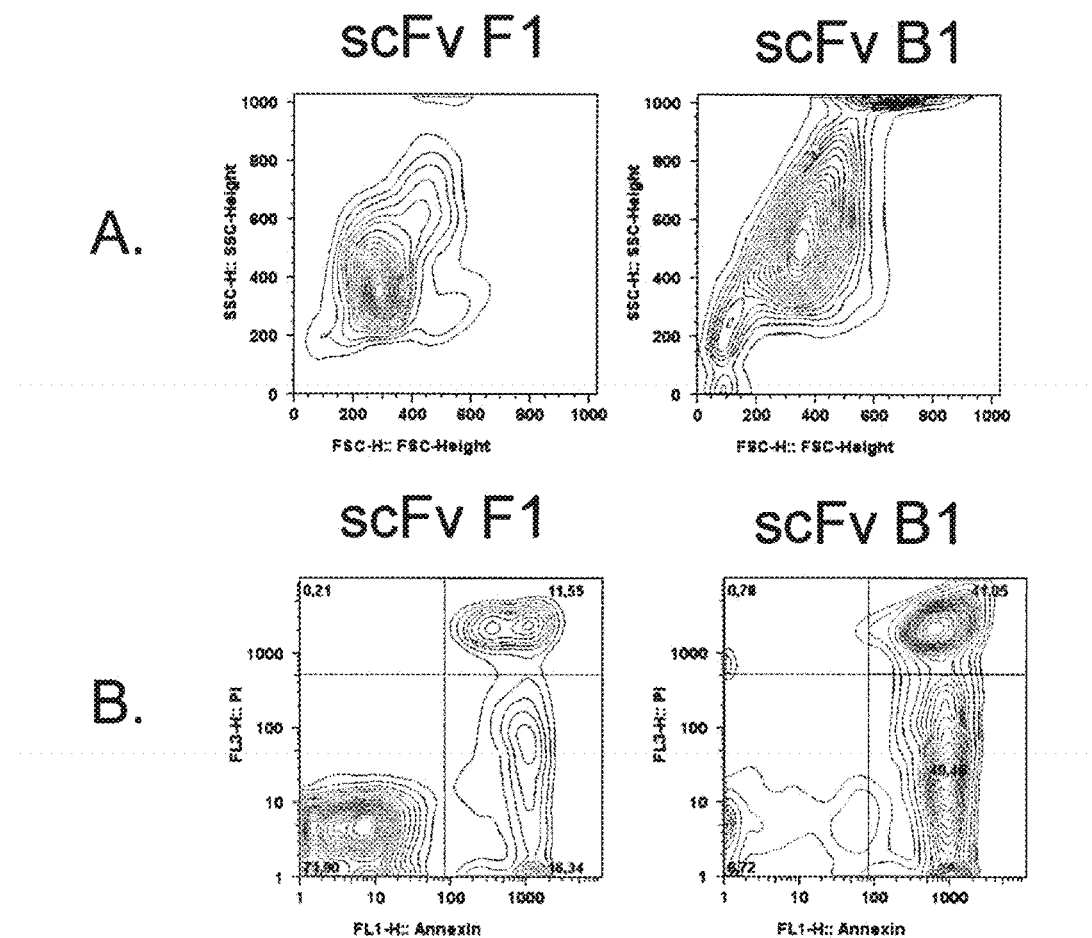

FIG. 2—Apoptosis induction of anti-Ramos scFv.

Ramos B lymphoma cells were sequentially incubated with anti-Ramos scFv, anti-His mAb, and anti-mouse polyclonal Ab on ice (with intermittent washing to remove excess unbound antibody), and were incubated in a humidified atmosphere of 5% $CO_2$ at 37° C. for 24 hours. Cells were then harvested and subjected to combined staining with Annexin V-AF488 (AV) and propidium iodide (PI). Cells were scored as viable (AV– PI–, filled circles FIG. 2C), early apoptotic (AV+PI–, open triangles FIG. 2C), or late apoptotic/necrotic (AV+PI+, open diamonds FIG. 2C), based on differential positivity for AV and PI staining (defined by square gates in FIG. 2B). Results are presented by plotting (FIG. 2A) Forward Scatter (FSC-Height) against Side Scatter and (FIG. 2B) AV (FL-1) against PI (FL-3). The titratable effect of scFv B1 and F1 is also presented (FIG. 2C). The seven unique scFv clones were incubated with (FIG. 2D) Ramos or (FIG. 2E) Raji B lymphoma cells at 37° C. for 24 hours at various concentrations and the effect on apoptosis induction studied. Three scFv; B1, B11, and C11, show titratable activity towards both cell lines, whereas apoptosis inducing capability of scFv B10, C10, and G12 is restricted to Ramos B lymphoma cells.

FIG. 3—Specificities of isolated antibodies include HLA-DR/DP, IgM, and ICAM-1.

FIG. 3A) 50-600×$10^6$ Raji B lymphoma cells were lysed with the non-ionic detergent Triton X-100 at 0.5% v/v and immunoprecipitated with 100 μg of the fully human IgG1 format of B1 (lane 1) and B11 (lane 2) antibody, followed by crosslinking with Protein A Sepharose. Ramos B lymphoma cell lysates, from 50×$10^6$ cells, were used for the precipitation of 20 μg C11 (lane 3). Antibody-specific bands were excised and subjected to tryptic digestion and analysed by MALDI-TOF.

FIG. 3B) B1 IgG, B11 IgG, and C11 IgG binding to B lymphoma cells is specifically blocked by pre-incubation with anti-HLA-DR/DP, anti-ICAM-1 or anti-IgM antibodies, respectively.

To confirm the retrieved MALDI-TOF antigen identities of antibody clones B1, B11, and C11, blocking studies with commercially available antibodies was carried out and analyzed by flow cytometry. Cells were pre-blocked with 10-fold molar excess (compared to the human antibody) of species-matched blocking antibodies for 1 h, followed by the addition of any of the isolated human antibody clones. After 30 min, cells were washed and binding of human antibody to cells was detected by PE-conjugated goat anti-human IgG (Caltag Laboratories, Burlingame, Calif., USA). The blocking antibodies used in the study were; for B1, mouse monoclonals anti-HLA DR (Sigma, clone HK14) or anti-CD40 (Beckton Dickinson, clone 5C3); for B11, rabbit polyclonals anti-ICAM-1 (Abcam, ab7815-250) or anti-CD22 (Abcam, ab25135-100); for C11, goat polyclonals anti-IgM (Zymed, South San Francisco, Calif., USA, 62-7500) or anti-IgG (Zymed, 62-8400).

Figure 4:
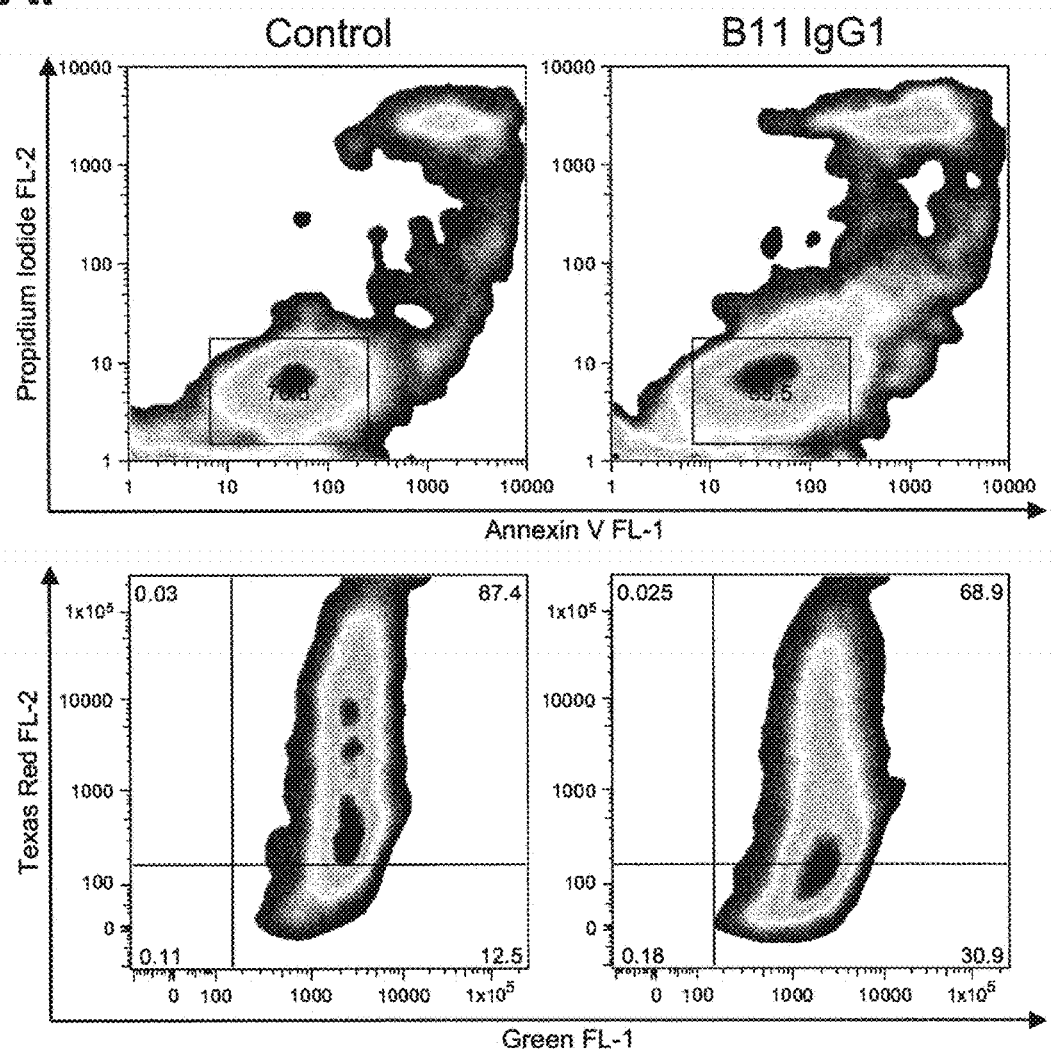

FIG. 4—ICAM-1 is a B lymphoma associated cell surface receptor capable of mediating programmed cell death.

FIG. 4A. 2 μg/ml of B11 or anti-FITC-8 (control) $IgG_1$ was added to 4×$10^5$ CL-01 B lymphoma cells, incubated for 2 h on ice, followed by addition of 10 μg/ml cross-linking secondary Fab'2 Goat anti-human Fc antibody. Cells were incubated at 37° C. for 6 h and the effect of the antibody incubation was determined by two independent apoptosis assays. Cells were stained either by AV/PI (upper panel), similarly as described above, or by incubation with 5 μg/ml of the mitochondrial membrane depolarisation reagent JC-1 for 30 min at RT (lower panel). Induction of apoptosis is detectable by a decrease in the red (y-axis)/green (x-axis) fluorescence intensity ratio. (FIG. 4B) Histology section showing representative binding of B11 antibody to B lymphoma tissue. Cryo-preserved tissue obtained from a patient with Anaplastic Large Cell B Lymphoma was stained with B11 or FITC-8 (control) scFv antibody. Antibody binding was detected with DAB (brown colour). Inset picture shows staining with control scFv. (FIG. 4C) CD45-PerCp-Cy5.5 mAb pre-labelled Ramos cells were mixed with donor-derived PBMCs and the different cell populations were stained with fluorochrome-conjugated CD-specific antibodies and Alexa Flour 647 Zenon pre-labelled B11 IgG1 or control FITC-8 IgG1. IgG B11 binding to the different cell populations was recorded in the FL4 channel.

Figure 5:
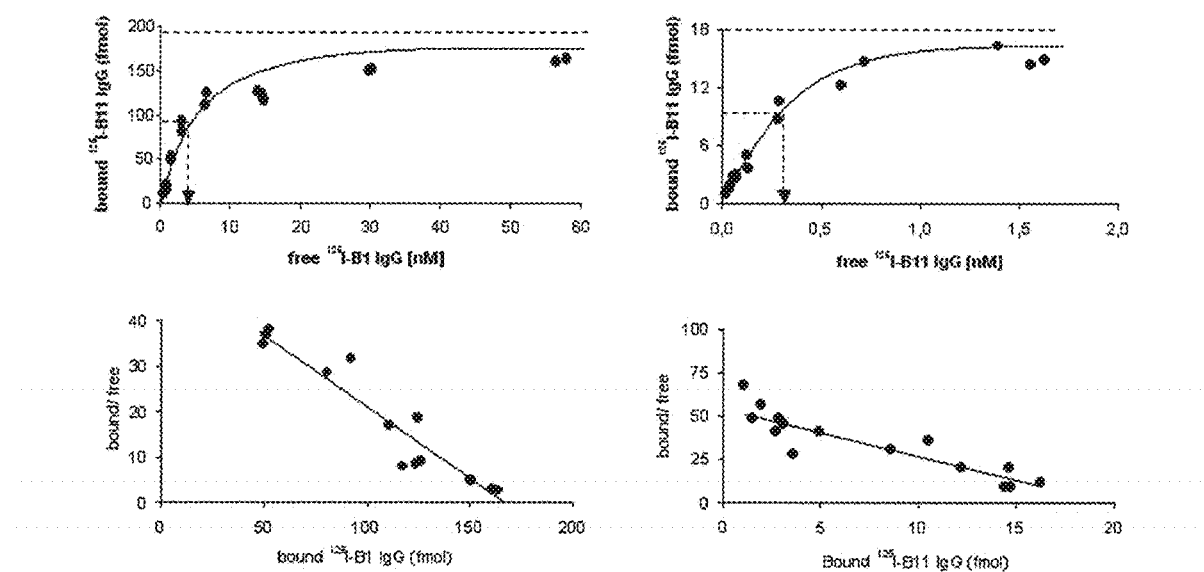

FIG. 5—Affinities of IgG B1 and IgG B11 to B lymphoma cells.

Raji cells (left panels, IgG B1) or Ramos cells (right panels, IgG B11) were incubated with increasing amounts of radioiodinated IgG B1 or radioiodinated IgG B11 protein in the presence or absence of 0.2 mg/ml of the corresponding unlabeled IgG protein. Specific binding was determined by subtracting binding in the presence of unlabeled competing protein from total binding. The amount of bound IgG B1 or IgG B11 protein increased with increasing amounts of free IgG protein with saturable binding being reached at ~30 nM IgG B1 and ~1 nM IgG B11, respectively (upper panels). Rosenthal-Scatchard plot analysis (lower panels) demonstrated a dissociation constant of ~3 nM with 400,000 functional binding sites per Raji cell for IgG B1, and a dissociation constant of ~0.3 nM with 47,400 functional binding sites for IgG B11 (Raji cells).

Figure 6:
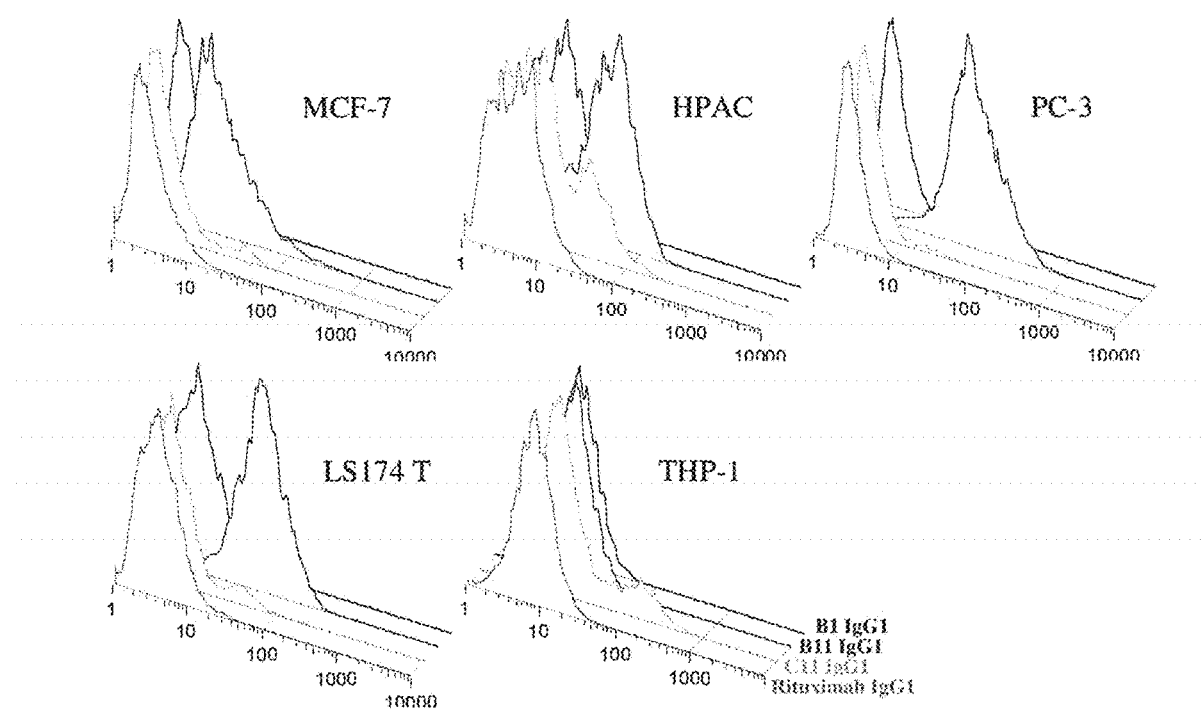

FIG. 6—Binding of B1, B11, C11 IgG, to tumour cell lines of different origin. The antigen distribution of antigens targeted by the B1, B11, and C11 antibodies on different carcinoma cell lines was investigated by flow-cytometry. Histograms show binding of Rituximab anti-CD20 Mab (first row front most peaks), B1 $IgG_1$ (second row peaks), B11 $IgG_1$ (third row peaks), or C11 $IgG_1$ (fourth row back most peaks) to MCF-7 breast carcinoma, HPAC pancreatic carcinoma, PC-3 prostate carcinoma, LS174 T colorectal carcinoma, and THP-1 monocytic leukaemia cells, as indicated.

FIG. 7—B11 IgG1 apoptosis induction in carcinoma cells

The prostate carcinoma cell line PC-3 was grown in Complete Growth Medium (RPMI 1640, supplemented with 10% FCS, 10 mM HEPES, and 2 mM L-Glutamine) to 80% confluency in a 6 well plate. The prostate carcinoma cell line DU145 was grown in MEM with Earl's salts, supplemented with 10% FCS, 1 mM sodium pyruvate, and 1 mM non-essential amino acids and the derivate of a melanoma cell line MDA MB 435 was grown in DMEM supplemented with 10% FCS.

For apoptosis assays cells were washed in PBS and serially diluted B11 $IgG_1$ (or B1 $IgG_1$, Trastuzumab or negative antibody control for controls) was added to individual wells and binding was allowed during a 1-2 h incubation at 4° C. The cells were washed and Complete Growth Medium was added, containing cross-linking antibody, Fab'2 Goat anti-Human Fab'2, at 10 μg/ml. Cells were incubated in a humidified atmosphere, with 5% $CO_2$ at 37° C., for 16-24 hours. Cells were collected by trypsination and stained with Alexa Fluor 488-Annexin V (AF488-AV) and propidium iodide (PI), according to manufacturer's instructions. The percentage apoptotic cells was determined by the formula: % apoptotic cells=100−% AF488−AV/PI−/−.

FIG. 7A Contour plots show the relative distribution of PC-3 cells as a function of Annexin V and Propidium Iodide positivity following incubation as above with 2 μg/ml IgG B11 or IgG B1.

FIG. 7B Bar graph shows the mean percentage of apoptotic PC-3 cells following incubation with serially diluted B11 IgG$_1$ or 20 μg/ml B1 IgG$_1$.

FIG. 7C Bar graph shows the mean percentage of apoptotic MDA MB 435 cells following incubation with no antibody control, 10 μg/ml negative antibody control, serially diluted B11 IgG$_1$, or 10 μg/ml Trastuzumb IgG$_1$.

FIG. 7D Bar graph shows the mean percentage of apoptotic DU145 cells following incubation with no antibody control, 10 μg/ml negative antibody control, serially diluted B11 IgG$_1$, or 10 μg/ml Trastuzumb IgG$_1$.

Figure 8:
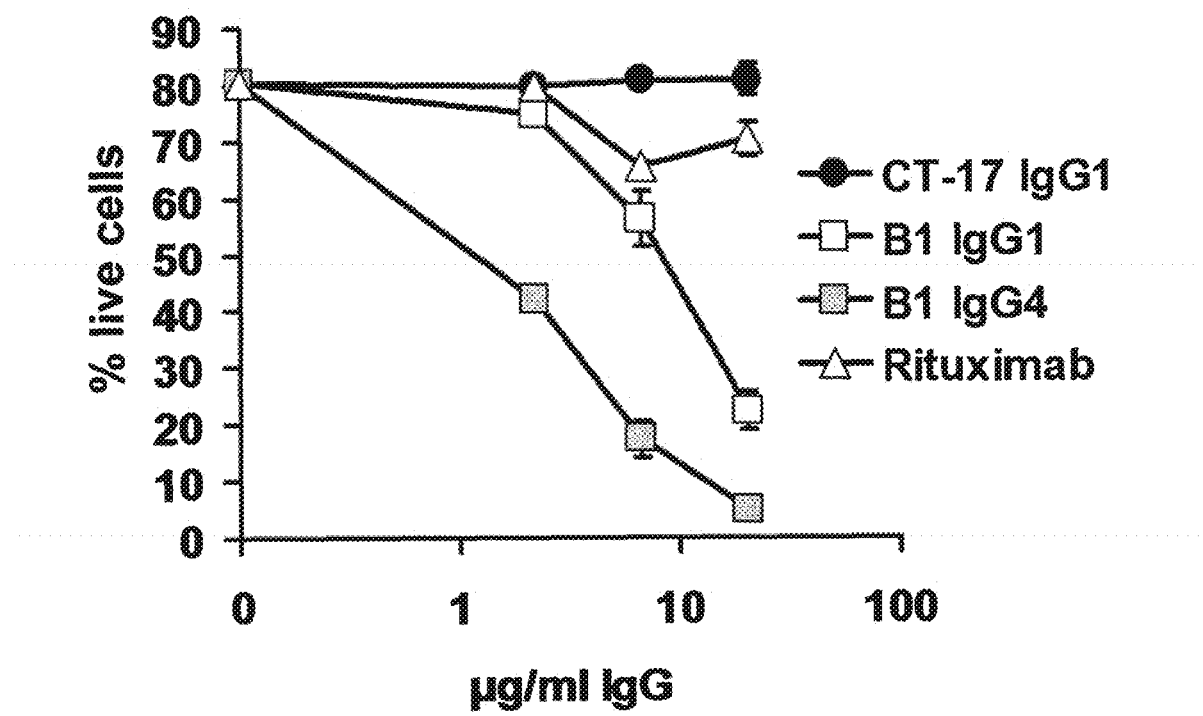

FIG. 8—B1 IgG1 and B1 IgG$_4$ induce direct cell cytotoxicity on Raji B lymphoma cells in the absence of cross-linking reagents.

Raji cells were incubated with B1 IgG$_1$, B1 IgG$_4$, Rituximab IgG$_1$, or control CT-17 IgG$_1$ at 20, 6.7 or 2.2 μg/ml for 24 hours. Cells were harvested and viability was determined as the percentage of Annexin V and Propidium Iodide double negative cells.

FIG. 9—VH and VL sequences (nucleotide sequences of SEQ ID NOs. 1 and 3, respectively, and amino acid sequences of SEQ ID NOs. 2 and 4, respectively) for B1 antibody.

FIG. 10—VH and VL sequences (nucleotide sequences of SEQ ID NOs. 5 and 7, respectively, and amino acid sequences of SEQ ID NOs. 6 and 8, respectively) for B11 antibody.

FIG. 11—VH and VL sequences (nucleotide sequences of SEQ ID NOs. 9 and 11, respectively, and amino acid sequences of SEQ ID NOs. 10 and 12, respectively) for C11 antibody.

FIG. 12—A function-first approach to the discovery of tumor-targeting human therapeutic antibodies.

FIG. 12A Differential biopanning for antibodies specific for tumor associated receptors. Schematic illustration of the biopanning process. The human phage-antibody (Pϕ ab) library n-CoDeR® was subjected to differential biopanning of tumor B cells vs T cells: 20×10$^{12}$ Pϕ abs were incubated with target tumor cells and excess plasma membrane vesicles produced from effector T cells, a cell type critical for tumor immunity that must not be targeted by candidate antibodies. Pϕ abs specific for tumor B cell-associated surface receptors (rod-like structures) thus bound to tumor B cells, while Pϕ abs specific for commonly expressed tumor B:T cell receptors (further rod-like structures) bound to T cell membrane vesicles because of their great (50 to 1000-fold) excess. Tumor cell-bound Pϕ abs specific for tumor B cell-associated receptors were separated from unbound and T cell vesicle-bound Pϕ abs by density centrifugation, based on the higher density of nucleated tumor B cells compared to that of membrane vesicles. Pϕ abs specific for tumor B cell-associated receptors were then eluted from pelleted tumor B cells.

FIG. 12B Programmed cell death screening. Antibody clones isolated by differential biopanning were screened for tumor PCD-inducing efficacy. Antibodies were cross-linked with anti-human Ig reagent to mimic FcR:Fc-enhanced PCD in vivo. PCD was measured as the % change in annexin V+/PI− cells following over-night incubation of tumor cells with antibodies.

FIG. 12C BI-505 binds specifically to ICAM-1. (a) Pre-incubation with recombinant ICAM-1, but not VCAM, blocks BI-505 binding to targeted tumor B cells. (b) BI-505 binds dose-dependently to recombinant ICAM-1 but not to ICAM-2 or ICAM-3.

FIG. 12D ICAM-1 or CD20 expression is not down regulated by BI-505 or rituximab treatment. ARH-77 xenograft tumors from mice treated with BI-505, rituximab or control IgG were stained for ICAM-1 or CD20 expression. Strong immune staining of ICAM-1 and CD20 was seen on tumor cells and detected in all of the tested sections. There were no apparent differences in ICAM-1 or CD20 expression between BI-505, rituximab and control IgG treated animals. Bar=40 μm.

Figure 13:
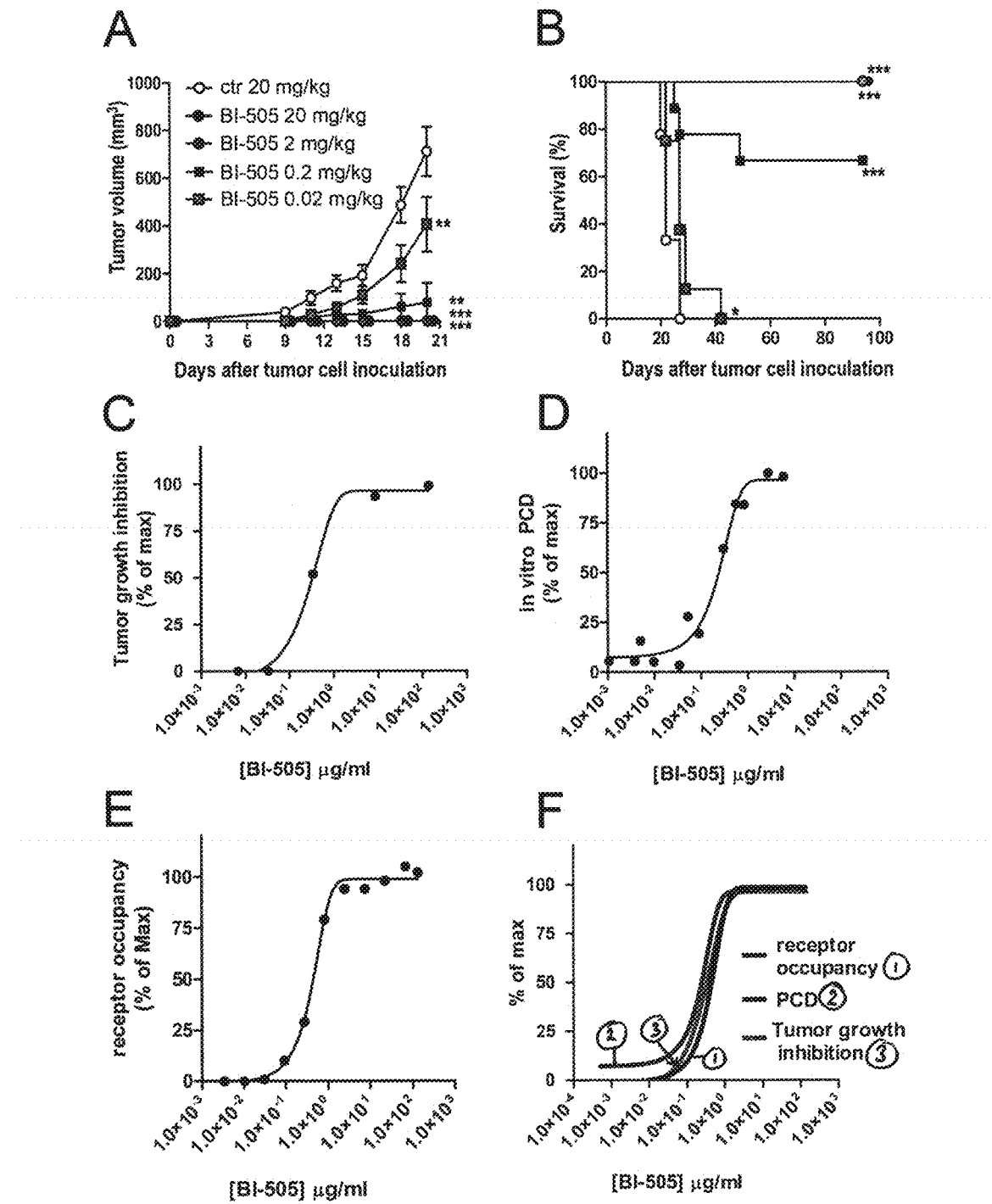

FIG. 13—BI-505 dose-dependent antitumor activity correlates with ICAM-1 receptor occupancy on tumor cell surfaces Mean tumor volumes (FIG. 13A) and mean survival (FIG. 13B) of mice treated with different doses of BI-505 in the ARH-77 tumor model. Error bars show±SD. *p<0.05, p<0.01, and *p<0.001.

BI-505 concentration-dependent in vivo antitumor activity (FIG. 13C), in vitro antitumor (tumor PCD) activity (FIG. 13D), receptor occupancy of tumor cell-expressed ICAM-1 (FIG. 13E).

(FIG. 13F) A combined plot of panels C-E. There were 8-10 animals per treatment group.

Figure 14:
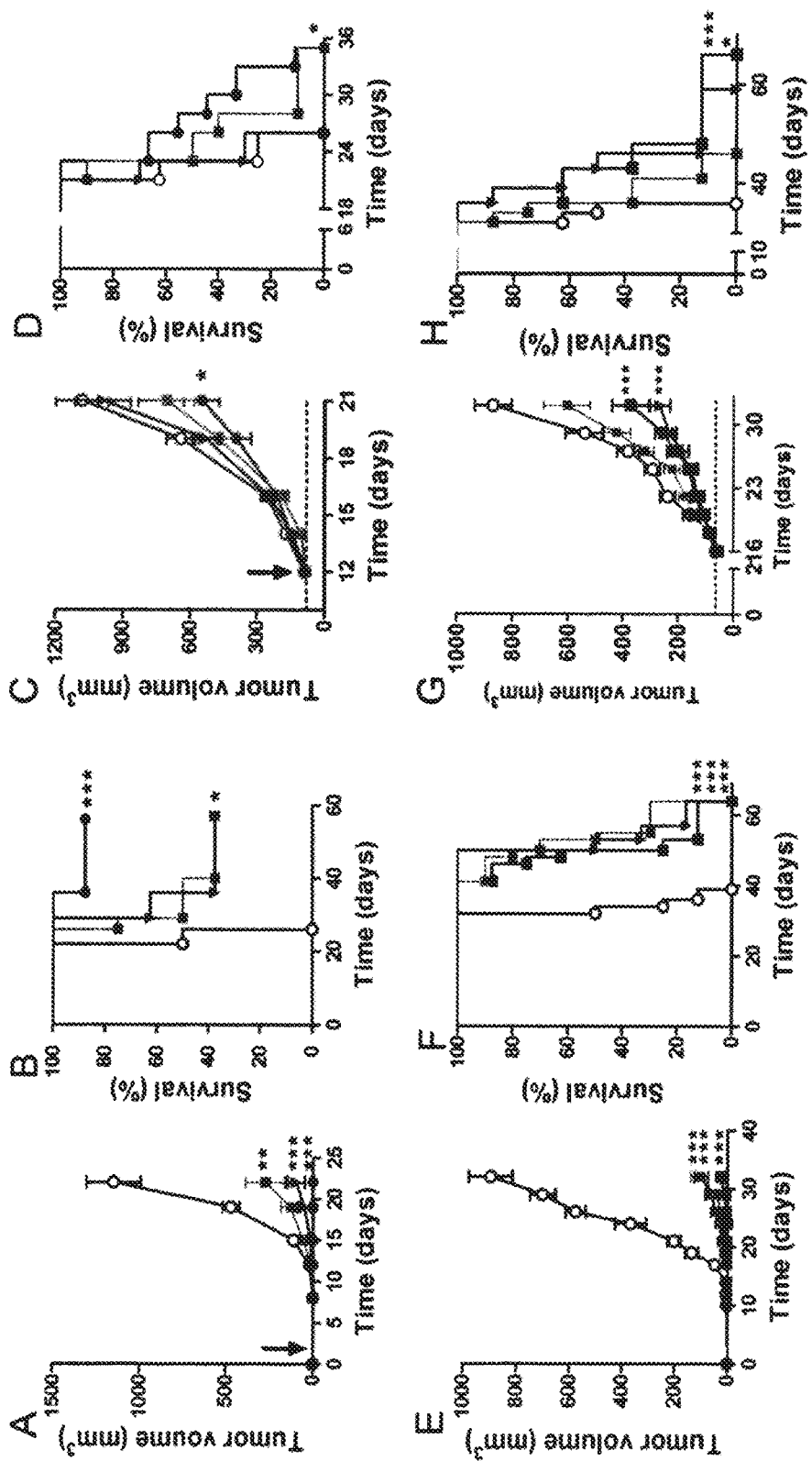

FIG. 14—BI-505 has significant in vivo antitumor activity against CD20-expressing tumors compared with rituximab.

(FIG. 14A-14H) Mean tumor volumes (FIG. 14A, 14C, 14E, 14G) and survival (14B, 14D, 14F, 14H) of CD20-expressing ARH-77. (FIG. 14A-14D) and Daudi (FIG. 14E-14H) cell treated with BI-505 (black circles=20 mg/kg BI-505, black squares=2 mg/kg BI-505, light grey squares=0.2 mg/kg BI-505), rituximab (20 mg/kg, dark triangles) or isotype control (20 mg/kg, open circles) antibodies in prophylactic (FIG. 14A, 14B, 14E, 14F) or established (FIG. 14C, 14D, 14G, 14H) tumor models. There were 8 to 10 animals per treatment/dose group. Tumor cells were injected day 0, and antibody treatment started as indicated in the graphs (black arrow). *p<0.05, p<0.01, and *p<0.001. Error bars show±SD.

(FIG. 14I, 14J) FACS analysis of BI-505 and rituximab epitopes on the surface of ARH-77 (FIG. 14I) and Daudi (FIG. 14J) tumor cells. Antibodies were used at binding saturating concentrations.

See also FIG. 12.

Figure 15:
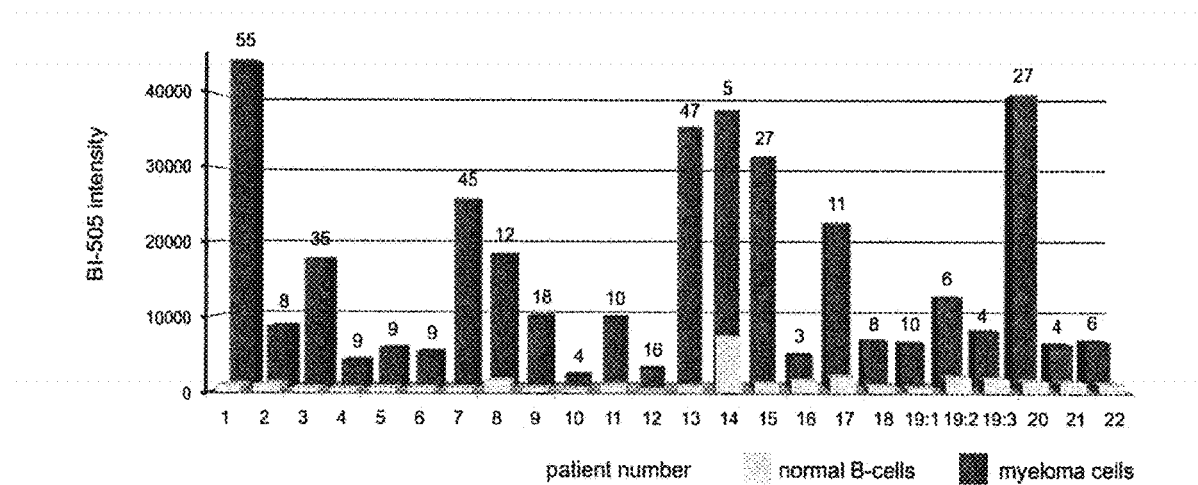

FIG. 15—The BI-505 epitope is highly expressed on the surface of primary multiple MM plasma cells.

FACS analysis of BI-505 epitope expression on the cell surface of patients' MM cells (dark shaded bars) versus normal B cells (light shaded bars). Numbers on top of bars indicate fold increase of the BI-505 epitope on surface of MM cells compared to normal B cells. Patient numbers correspond to those shown in Table 1.

Figure 16:
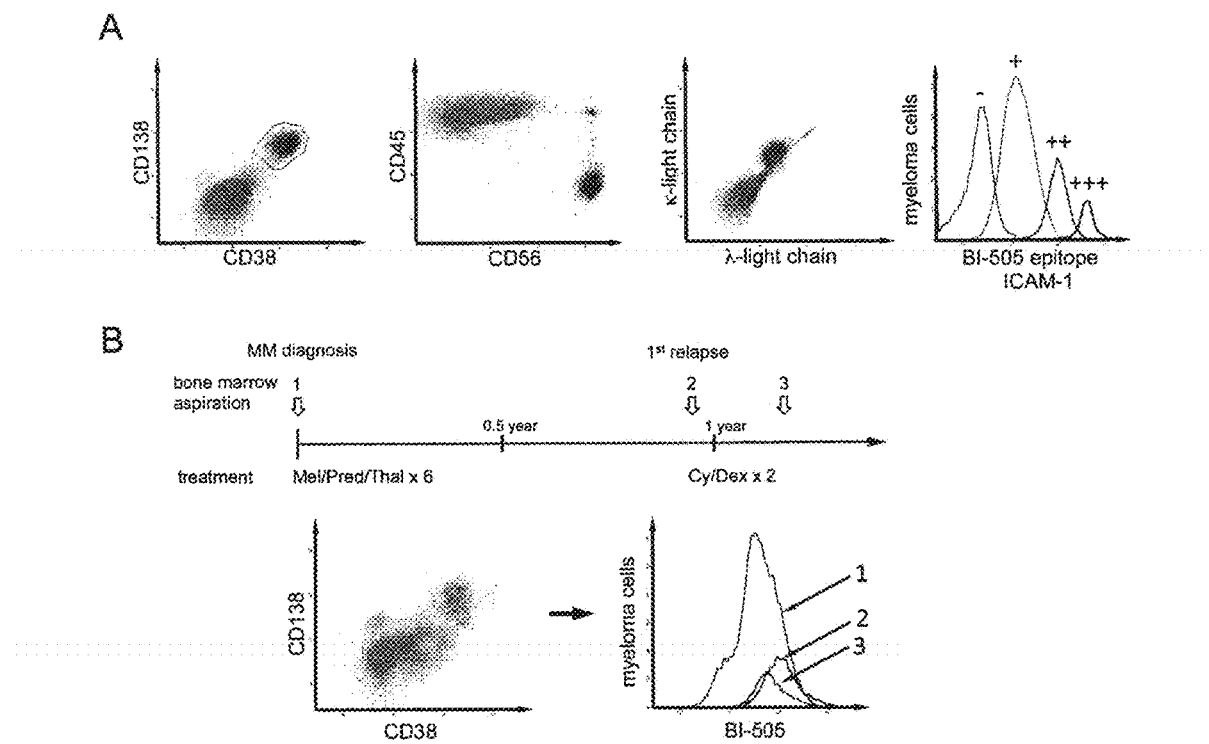

See also FIG. 16.

FIG. 16—FACS analysis of Multiple myeloma cell surface BI-505 epitope expression.

(FIG. 16A) Analysis of myeloma cells in bone marrow from multiple myeloma patients by flow cytometry. Myeloma cells were gated based on expression of CD138, CD38, CD56 and CD45 according to international guidelines (Rawstron et al., 2008). Furthermore, intracellular staining was used to confirm monoclonal expression by K and A staining. B1-505 epitope expression was categorized as shown in the histogram (right position) with (+), (++) and (+++) corresponding to patient number 8, 7 and 10. BI-505 negative cells (−) are B-cells from patient number 8.

(FIG. 16B) BI-505 epitope expression on myeloma cells during disease progression in a patient with multiple myeloma. Bone marrow plasma cells were taken at diagnosis (bone marrow number 1) of a 79 year old man with multiple myeloma. Treatment was initiated with oral melphalan and dexamethasone pulses (six cycles) in combination with continuous thalidomide, resulting in a major response. However, two months after treatment cessation, the patient relapsed (bone marrow number 2). This time the patient received two cycles of cyclophosphamide and dexamethasone pulses followed by a new evaluation of the bone marrow (bone marrow number 3). Mean BI-505 expression in myleoma cells increased two-fold after first relapse (histogram, right).

Figure 17:
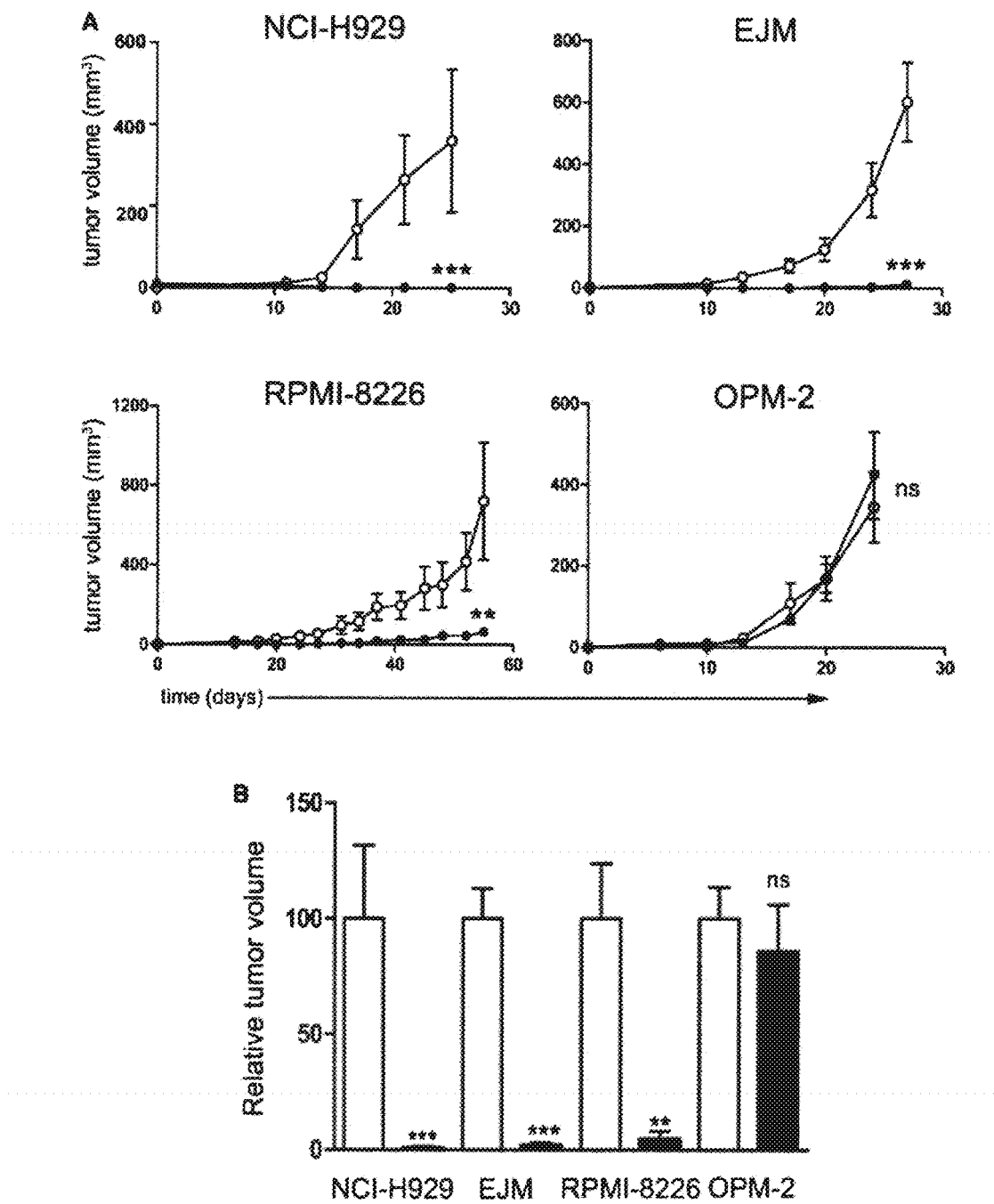

FIG. 17—BI-505 has broad and ICAM-1-dependent anti-MM activity in vivo (FIG. 17A) Tumor volume (mean±SD) of NCI-H929 (ICAM-1$^+$), EJM (ICAM-1$^+$), RPMI-8226 (ICAM-1$^+$), and OPM-2 (ICAM-1$^-$) MM models after treatment with 2 mg/kg BI-505 (filled circles) or control (open circles) antibody.

(FIG. 17B) Relative tumor volumes following treatment with 2 mg/kg BI-505 (filled bars) or control (open bars) antibody in NCI-H929, EJM, RPMI-8226, and OPM-2 MM models. Graph shows tumor volumes (mean±SD) relative to the mean tumor volume of control IgG treated animals. There were 8 animals per treatment group.
$p<0.01$, *$p<0.001$, ns=not statistically different.

Figure 18:
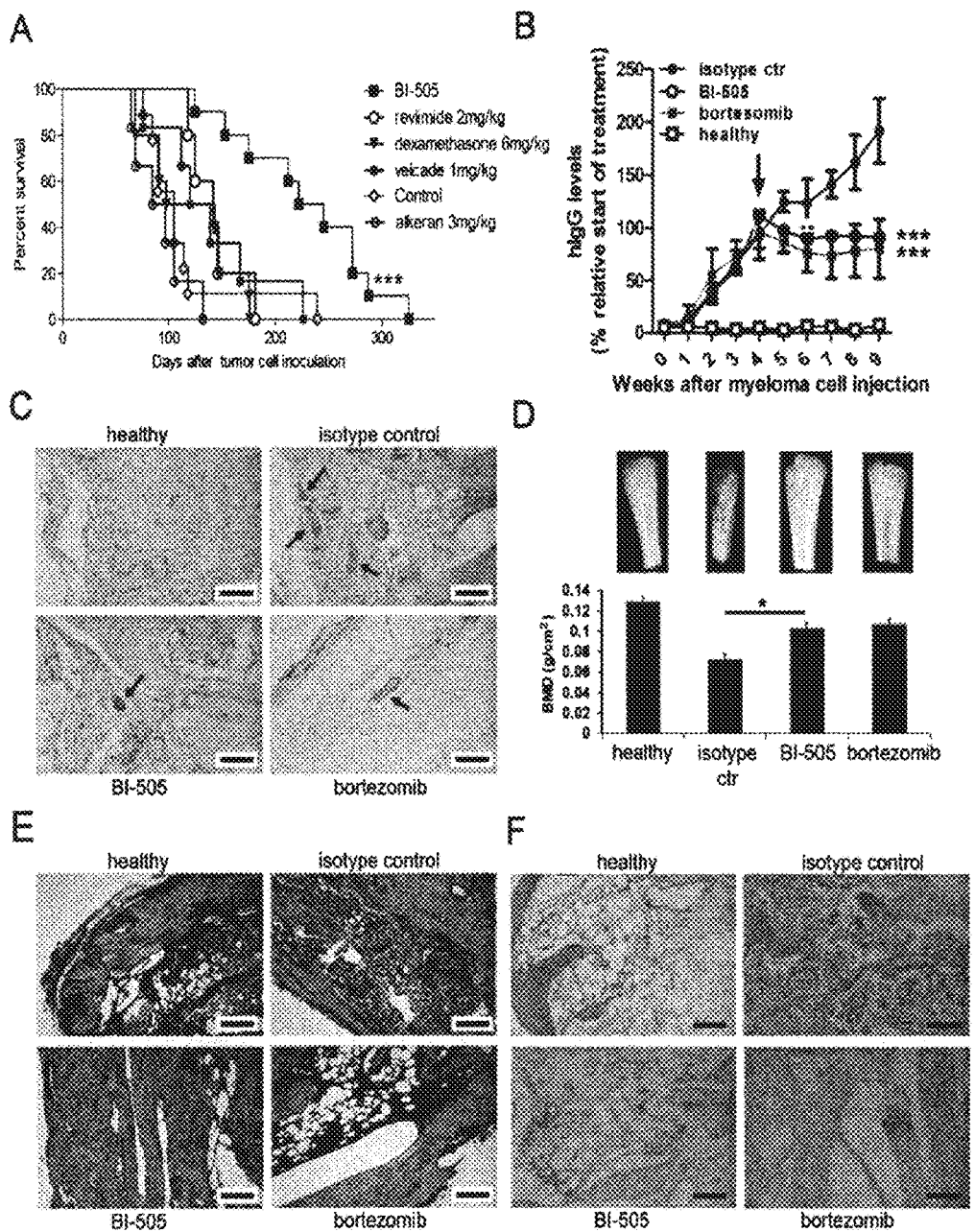

FIG. 18—BI-505 confers enhanced survival compared to currently used treatments in disseminated experimental models of advanced MM (FIG. 18A) Animal survival in advanced disseminated RPMI-8226 myeloma model following treatment with control antibody, lenalidomide, bortezomib, dexamethasone (DXH), melphalan, or BI-505. ***$p<0.001$.

(FIG. 18B) hIgG (mean±SD) in SCID-hu mice after myeloma cell inoculation and drug treatment. Graph shows pooled data from two independent experiments, each with MM cells obtained from two different patient donors (n=4). The percentage of hIgG levels compared to start of treatment (arrow) was monitored. ***$p<0.001$.

(FIG. 18C) Myeloma tumor burden in implanted bones harvested from drug treated mice. Pictures show representative images of tumor burden as assessed by immunohistochemistry following staining for human CD138 expressing cells. Arrows indicate human CD138 positive myeloma cell regions. Scale bar=50 μm.

(FIG. 18D) X-radiographic quantification of bone mineral density. Radiographs of implanted human bones receiving drug or control treatment were harvested from mice at end of experimentation (10 weeks post myeloma cell injection and following 6 weeks of drug treatment). Upper panel shows representative radiographs of bones from healthy mice, control IgG treated mice, BI-505 treated mice, or bortezomib treated mice (left to right). Lower panel shows mean±SD bone mineral density of mice receiving treatment as indicated. * $p<0.05$ (FIGS. 18E & 18F) Representative images of trap staining for detection of osteoclasts (E) or hematoxylin/eosin staining for detection of infiltrated nucleated cells (F) performed on healthy and MM cell-injected bones harvested from SCID-hu mice, treated as indicated, at end of experimentation. Scale bar=100 μm.

Figure 19:
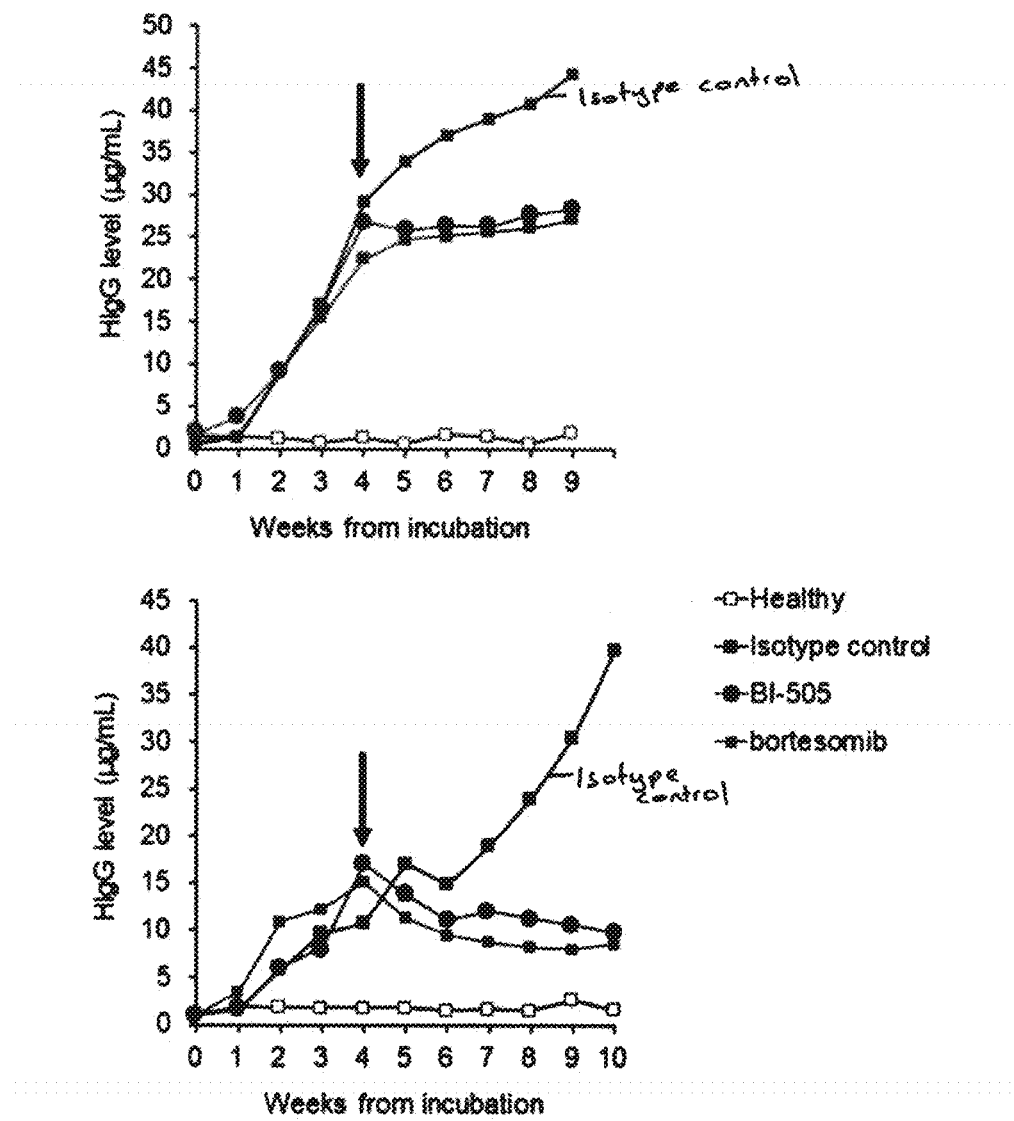

See also FIG. 19.

FIG. 19—hIgG levels in SCID-hu mice treated with ctrl IgG, BI-505 or bortezomib.

Bone marrow cells (>20% plasma cells) from myeloma patients (two patients in experiment 1 [top panel] and two different patients in experiment 2 [lower panel]) were injected into transplanted human fetal bones of SCID-hu mice. Four weeks after myeloma cell inoculation mice were divided into four groups to yield similar mean hIgG levels between groups, each group comprising mice grafted with MM cells from the different patient donors used in the experiment, and twice weekly treatment with 2 mg/kg BI-505, 1 mg/kg bortezomib or 2 mg/kg control human IgG was started (arrow). One group of mice "healthy" did not receive myeloma cells or drug treatment. Graphs show mean hIgG concentrations.

Figure 20:
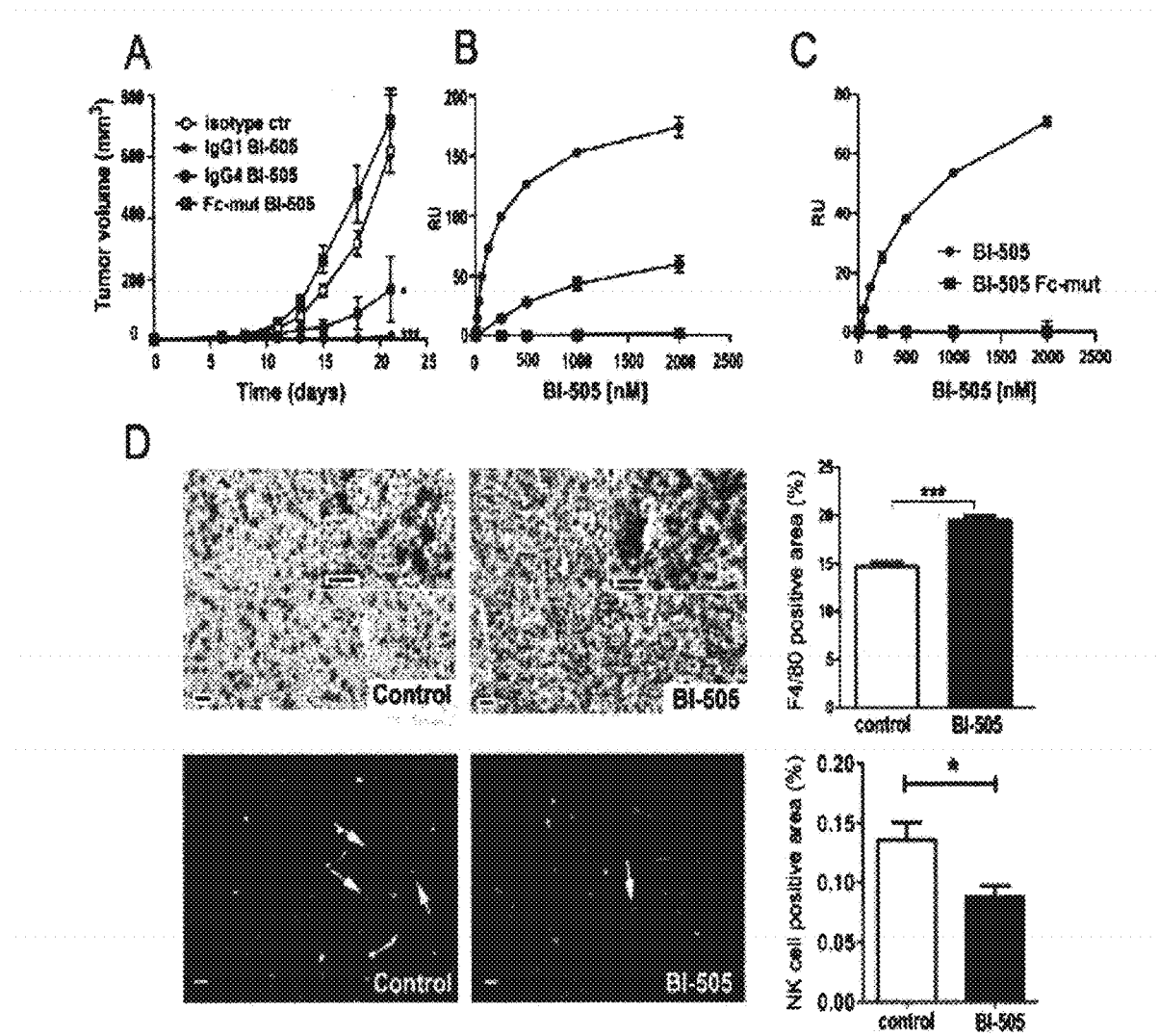

FIG. 20—BI-505 confers Fc-FcγR dependent antitumor activity through macrophages (FIG. 20A) Mean tumor volume of SCID mice bearing established ARH-77 tumors and treated with isotype control antibody or BI-505 IgG$_1$, BI-505 IgG$_4$, or BI-505 IgG$_{1\ N297Q}$ (Fc-variant) antibodies. *$p<0.05$, **$p<0.01$.

(FIG. 20B) BiaCore analysis of BI-505 Fc-variant antibodies binding to mouse FcγRIV.

(FIG. 20C) BiaCore analysis of BI-505 Fc-variant antibodies binding to human FcγRIIIa.

(FIG. 20D) Immunohistochemical quantitation of F4/80$^+$ macrophages (top panel) or NK cells (lower panel) in tumor tissue of animals bearing established ARH-77 tumors treated with control antibody or BI-505. Graphs show mean F4/80$^+$ and NK cell positive tumor areas, respectively. Bar=40 μm. *$p<0.05$, ***$p<0.001$.

(FIG. 20E) Tumor growth in macrophage or NK cell depleted SCID mice bearing established RPMI-8226 myeloma tumors treated with B1-505 or control antibody. ***$p<0.001$.

(FIG. 20F) Animal survival following BI-505 or control antibody treatment in a disseminated NK-cell deficient NOD/Shi-scid/IL-2Rγ$^{-/-}$ mouse model comprising i.v. grafted U266 myeloma cells. ***$p<0.001$.

(FIG. 20G) Tumor growth in BI-505 or control antibody treated NK-cell deficient NOD/Shi-scid/IL-2Rγ$^{-/-}$ mice transplanted with RPMI-8226 myeloma cells. ***$p<0.001$.

(FIG. H) Macrophage ADCP of RPMI-8226 and OPM-2 myeloma cells. n=4, ***$p<0.001$.

(FIG. 20I) Macrophage-mediated ADCP of primary multiple myeloma cells. n=2, ***$p<0.001$.

(FIG. 20J) Macrophage ADCP of ICAM-1$^+$ EJM myeloma cells. n=2, ***$p<0.001$.

There were 8-10 animals per treatment group. Error bars show±SD.

See also FIG. 21, and Table 5.

FIG. 21–BI-505 IgG$_1$, IgG$_4$ and IgG$_{1\ N297Q}$ antibodies have similar affinity for ICAM-1

(FIG. 21A) BI-505 IgG$_1$, IgG$_4$ and IgG$_{1\ N297Q}$ antibodies were analyzed for binding to recombinant ICAM-1 by ELISA.

(FIG. 21B) BI-505 IgG$_1$, IgG$_4$ and IgG$_{1\ N297Q}$ antibodies were analyzed for binding to tumor cell (ARH-77) surface ICAM-1 by flow-cytometry. Error bars show±SD.

(FIG. 21C) BI-505 IgG$_1$, IgG$_4$ and IgG$_{1\ N297Q}$ isotype variants compete for binding to tumor cell surface ICAM-1. The binding of Zenon APC-labeled BI-505 IgG$_1$ to tumor cell surface ICAM-1 was analysed following pre-blocking of cells with a 100-fold molar excess of BI-505 IgG$_1$, IgG$_4$ or IgG$_{1\ N297Q}$ antibodies.

(FIGS. 21D & 21E) Assessment of macrophage and NK-cell depletion in spleen (D) and mean tumor volume (E) from SCID mice bearing established RPMI-8226 tumors treated with clodronate or anti-Asialo GM1, respectively, for three weeks. Graphs show mean±SD.

Figure 22:
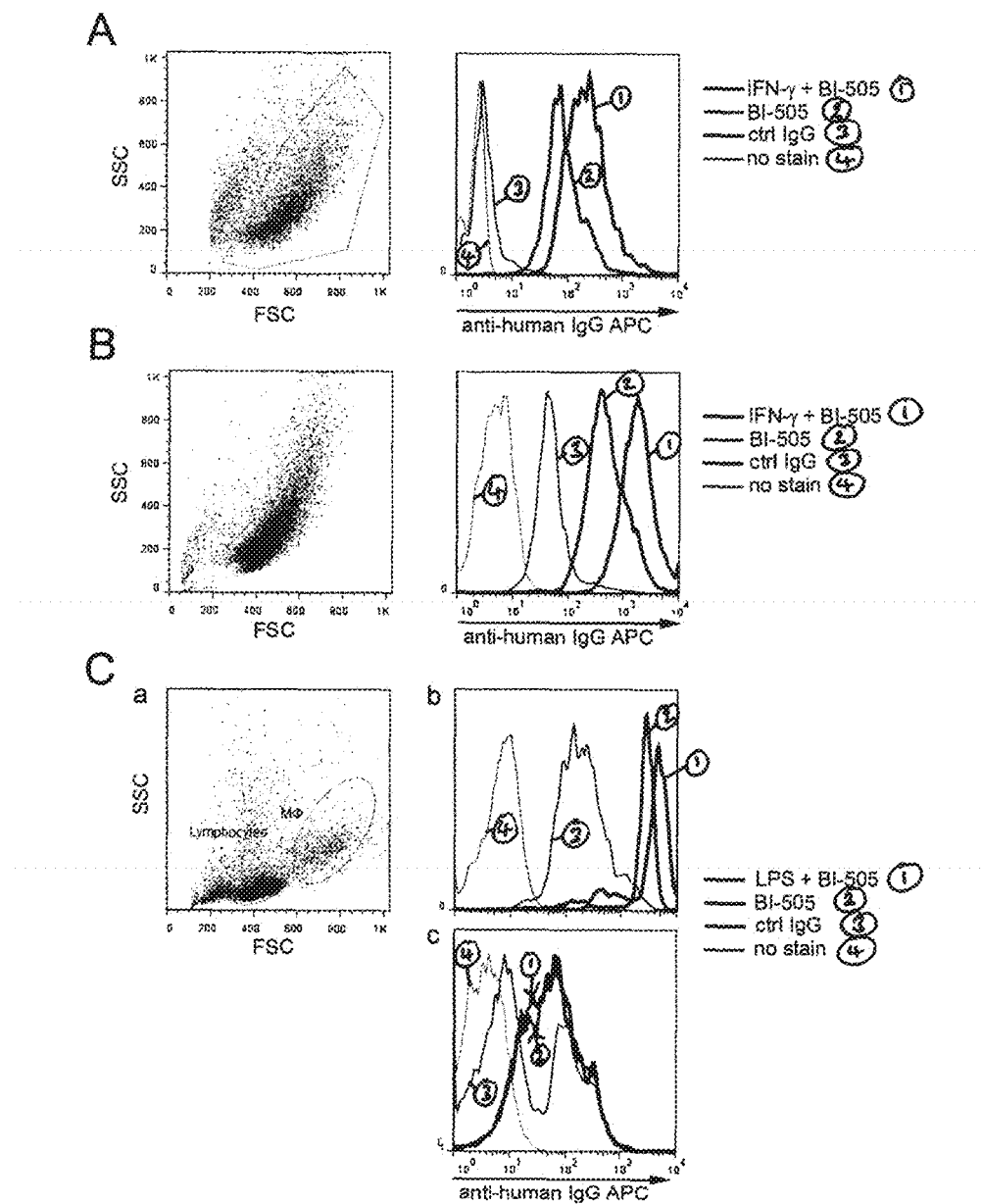

FIG. 22—Endothelial cell and PBMC BI-505 epitope expression.

HUVEC (FIG. 21A) or HMVEC (FIG. 21B) cells stimulated, or not, with IFN-γ for 48 hr were stained with BI-505 or ctrl antibody. (FIG. 21C) PBMCs stimulated, or not, with 10 ng/ml lipopolysaccharide were stained with BI-505 or ctrl antibody. Scattergram shows LPS-stimulated PBMCs (panel a). Histograms show ICAM-1 expression of lymphocytes (panel b) and monocytes (panel c), gated as indicated in (panel a) based on forward scatter and side scatter properties.

Figure 23:
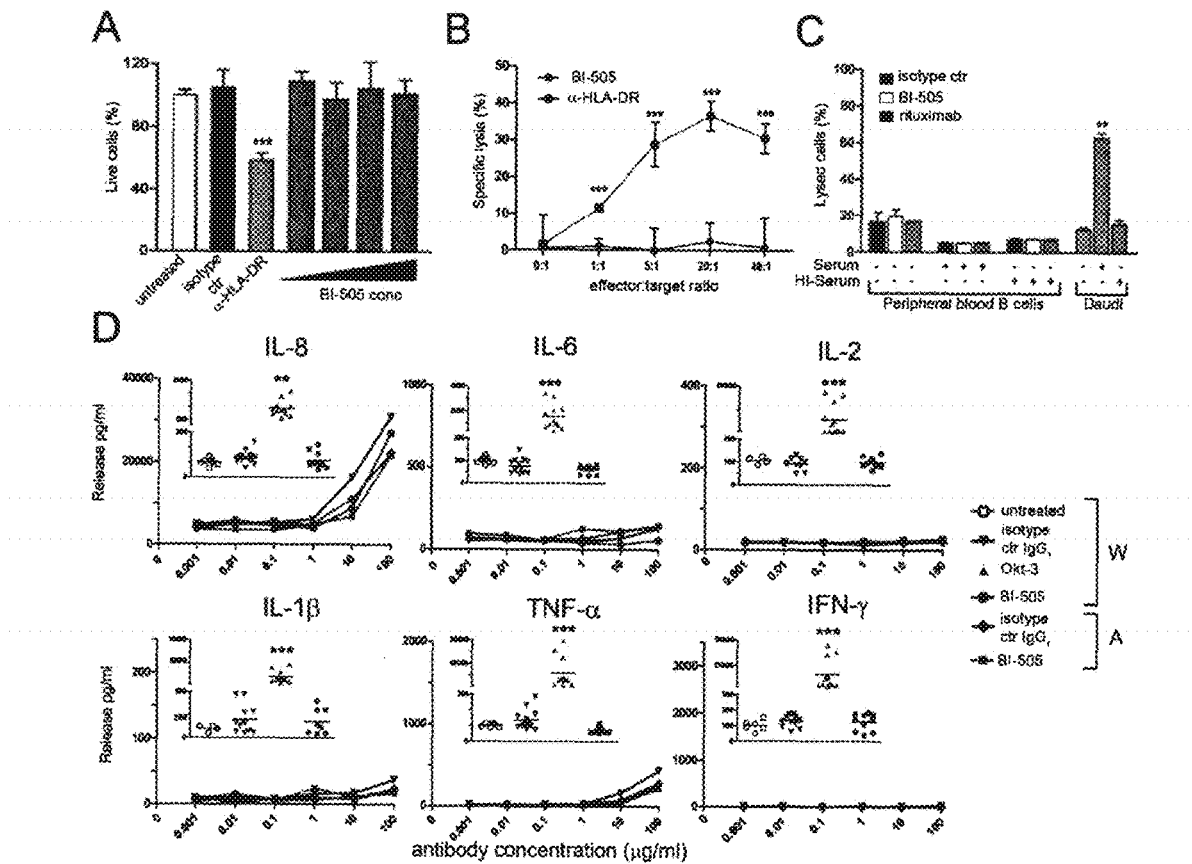

FIG. 23—BI-505 does not induce apoptosis, ADCC, CDC, T-cell proliferation, or cytokine release in resting or stimulated normal cells expressing ICAM-1

(FIG. 23A) Apoptosis in peripheral blood B cells. Graph shows % live (non-apoptotic) B cells following no treatment or treatment with isotype control IgG, anti-HLA-DR (pos ctrl IgG), or BI-505 (0, 1.5, 6, or 24 µg/ml). All values were normalized to untreated cells, where % living cells was set to 100.

(FIG. 23B) ADCC of peripheral blood B cells. Graph shows specific lysis of target peripheral blood B cells following treatment with BI-505 or anti-HLA-DR IgG$_1$ (positive control). All values were normalized to treatment with isotype control IgG, where specific lysis was set to 0%.

(FIG. 23C) CDC of peripheral blood B cells and Daudi Burkitt's lymphoma cells. Cells were incubated with BI-505, rituximab or isotype control IgG and analyzed for CDC.

(FIG. 23D) Antibody-induced PBMC cytokine release. PBMC cytokine release was measured by ELISA of cell culture supernatants for IL-1β, IL-2, IL-6, IL-8, IFN-γ and TNF-α following incubation of cells in plates coated with hyper cross-linked (air-dried "A" or wet coated "W") BI-505, isotype control, or positive control Okt-3 antibody.

(FIG. 23E) Antibody-induced cytokine release in LPS-primed PBMC. PBMC were incubated with titrated LPS and concentrations yielding submaximal cellular release of IL-1β. (100 pg/ml), IL-6 (10 pg/ml), IL-8 (10 pg/ml), and TNF-α (10 pg/ml) were determined (arrows, left panel), and used in subsequent experiments assessing antibody (BI-505 or ctrl IgG) effects on cytokine release from LPS-primed PBMC (right panel). Treatment with 100 ng/ml LPS served as positive control for robust cytokine release.

(FIG. 23F) Antibody induced T-cell proliferation. CFSE-labeled T-cells were incubated with BI-505, isotype control IgG or anti-CD3 (okt-3) IgG hyperimmobilised to cell culture plates by air-drying "A" or wet-coating "W". Cells were cultured for 6 days, and T cell proliferation was monitored by flow-cytometry as decreased CFSE signals.

(FIG. 23G) Antibody-induced endothelial cell apoptosis. HUVEC or HMVEC endothelial cells were incubated with paclitaxel (positive control), BI-505 or isotype control IgG in the presence or absence of cross-linking mAb. Apoptosis was measured by flow-cytometry following staining of cells with Annexin V-AF488.

p<0.01, *p<0.001. Error bars show±SD.

See also FIG. 22 and Table 6.

DETAILED DESCRIPTION OF THE INVENTION

Meanings of Terms Used

The term "antibody molecule" shall be taken to refer to any one of an antibody, an antibody fragment, or antibody derivative. It is intended to embrace wildtype antibodies, synthetic antibodies, recombinant antibodies or antibody hybrids, such as, but not limited to, a single-chain modified antibody molecule produced by phage-display of immunoglobulin light and/or heavy chain variable and/or constant regions, or other immunointeractive molecules capable of binding to an antigen in an immunoassay format that is known to those skilled in the art.

The term "antibody fragment" shall be taken to refer to any one of an antibody, an antibody fragment, or antibody derivative. It is intended to embrace wildtype antibodies (i.e. a molecule comprising four polypeptide chains), synthetic antibodies, recombinant antibodies or antibody hybrids, such as, but not limited to, a single-chain modified antibody molecule produced by phage-display of immunoglobulin light and/or heavy chain variable and/or constant regions, or other immunointeractive molecules capable of binding to an antigen in an immunoassay format that is known to those skilled in the art.

The term "antibody derivative" refers to any modified antibody molecule that is capable of binding to an antigen in an immunoassay format that is known to those skilled in the art, such as a fragment of an antibody (e.g. Fab or Fv fragment), or a modified antibody molecule that is modified by the addition of one or more amino acids or other molecules to facilitate coupling the antibodies to another peptide or polypeptide, to a large carrier protein or to a solid support (e.g. the amino acids tyrosine, lysine, glutamic acid, aspartic acid, cysteine and derivatives thereof, NH$_2$-acetyl groups or COOH-terminal amino groups, amongst others).

The term "ScFv molecule" refers to any molecules wherein the V$_H$ and V$_L$ partner domains are linked via a flexible oligopeptide.

The terms "nucleotide sequence" or "nucleic acid" or "polynucleotide" or "oligonucleotide" are used interchangeably and refer to a heteropolymer of nucleotides or the sequence of these nucleotides. These phrases also refer to DNA or RNA of genomic or synthetic origin which may be single-stranded or double-stranded and may represent the sense or the antisense strand, to peptide nucleic acid (PNA) or to any DNA-like or RNA-like material. In the sequences herein A is adenine, C is cytosine, T is thymine, G is guanine and N is A, C, G or T (U). It is contemplated that where the polynucleotide is RNA, the T (thymine) in the sequences provided herein is substituted with U (uracil). Generally, nucleic acid segments provided by this invention may be assembled from fragments of the genome and short oligonucleotide linkers, or from a series of oligonucleotides, or from individual nucleotides, to provide a synthetic nucleic acid which is capable of being expressed in a recombinant transcriptional unit comprising regulatory elements derived from a microbial or viral operon, or a eukaryotic gene.

The terms "polypeptide" or "peptide" or "amino acid sequence" refer to an oligopeptide, peptide, polypeptide or protein sequence or fragment thereof and to naturally occurring or synthetic molecules. A polypeptide "fragment," "portion," or "segment" is a stretch of amino acid residues of at least about 5 amino acids, preferably at least about 7 amino acids, more preferably at least about 9 amino acids and most preferably at least about 17 or more amino acids. To be active, any polypeptide must have sufficient length to display biological and/or immunological activity.

The terms "purified" or "substantially purified" as used herein denotes that the indicated nucleic acid or polypeptide is present in the substantial absence of other biological macromolecules, e.g., polynucleotides, proteins, and the like. In one embodiment, the polynucleotide or polypeptide is purified such that it constitutes at least 95% by weight, more preferably at least 99% by weight, of the indicated biological macromolecules present (but water, buffers, and other small molecules, especially molecules having a molecular weight of less than 1000 daltons, can be present).

The term "isolated" as used herein refers to a nucleic acid or polypeptide separated from at least one other component (e.g., nucleic acid or polypeptide) present with the nucleic acid or polypeptide in its natural source. In one embodiment, the nucleic acid or polypeptide is found in the presence of (if anything) only a solvent, buffer, ion, or other component normally present in a solution of the same. The terms "isolated" and "purified" do not encompass nucleic acids or polypeptides present in their natural source.

The term "recombinant," when used herein to refer to a polypeptide or protein, means that a polypeptide or protein is derived from recombinant (e.g., microbial, insect, or mammalian) expression systems. "Microbial" refers to recombinant polypeptides or proteins made in bacterial or fungal (e.g., yeast) expression systems. As a product, "recombinant microbial" defines a polypeptide or protein essentially free of native endogenous substances and unaccompanied by associated native glycosylation. Polypeptides or proteins expressed in most bacterial cultures, e.g., *Escherichia coli*, will be free of glycosylation modifications; polypeptides or proteins expressed in yeast will have a glycosylation pattern in general different from those expressed in mammalian cells.

The terms "selective binding" and "binding selectivity" indicates that the variable regions of the antibodies of the invention recognise and bind polypeptides of the invention exclusively (i.e., able to distinguish the polypeptide of the invention from other similar polypeptides despite sequence identity, homology, or similarity found in the family of polypeptides), but may also interact with other proteins (for example, *Staphylococcus aureus* protein A or other antibodies in ELISA techniques) through interactions with sequences outside the variable region of the antibodies, and in particular, in the constant region of the molecule. Screening assays to determine binding selectivity of an antibody of the invention are well known and routinely practiced in the art. For a comprehensive discussion of such assays, see Harlow et al. (Eds), *Antibodies A Laboratory Manual*, Cold Spring Harbor Laboratory, Cold Spring Harbor, N.Y. (1988), Chapter 6. Antibodies that recognise and bind fragments of the polypeptides of the invention are also contemplated, provided that the antibodies are first and foremost selective for, as defined above, full-length polypeptides of the invention. As with antibodies that are selective for full length polypeptides of the invention, antibodies of the invention that recognise fragments are those which can distinguish polypeptides from the same family of polypeptides despite inherent sequence identity, homology, or similarity found in the family of proteins.

The term "binding affinity" includes the meaning of the strength of binding between an antibody molecule and an antigen.

By the term "immune cell" we mean any cell that is involved in a host immune or inflammatory response, including but not limited to B cells and T cells.

By the term "epithelial cell" we mean a cell of the epithelium. Epithelium is a tissue composed of a layer of cells. Epithelium can be found lining internal (e.g. endothelium, which lines the inside of blood vessels) or external (e.g. skin) free surfaces of the body.

The outermost layer of our skin is composed of squamous epithelial cells, as are the mucous membranes lining the inside of mouths and body cavities. Other epithelial cells line the insides of the lungs, the gastrointestinal tract, the reproductive and urinary tracts, and make up the exocrine and endocrine glands. Functions of epithelial cells include secretion, absorption and protection. Epithelial cells sit on a basal lamina.

Preferred Embodiments

Examples embodying certain preferred aspects of the invention are described herein, with reference to the figures and legends thereof (see above).

Example 1—Selection and Screening (Biopanning) for Apoptosis Inducing Antibodies with Specificity for B Lymphoma Associated Cell Surface Receptors Cell Culture The cell lines used in this study were obtained from ATCC (Manassas, Va., USA) or Deutsche Sammlung von Mikroorganismen and Zellkulturen (DSMZ) GmbH (Braunschweig, Germany) and were cultured in RPMI 1640 medium supplemented with 10% FCS, 2 mM L-Glutamine, 10 mM HEPES and 1 mM Na pyruvate (all from Invitrogen, Carlsbad, Calif., USA) unless otherwise stated. The Jurkat T leukaemia cell line (clone E6-1, TIB-152, ATCC), the B lymphoma cell lines DOHH-2 (ACC47, DSMZ), SC-1 (ACC558, DSMZ), WSU-NHL (ACC58, DSMZ), JVM-2 (ACC12, DSMZ), Jeko-1 (ACC553, DSMZ grown in 20% FCS), Rec-1 (ACC 584, DSMZ), SP-53 (Daibata et al., *Cancer* (1989) 64:1248-1253), RL (CRL-2261, ATCC), Granta 519 (DSMZ), NCEB-1 (Saltman et al., *Blood* (1988) 72:2026-2030), BJAB (Menezes et al., *Biomedicine* (1975) 22:276-284), Ramos (CRL-1596, ATCC), Raji (CCL-86, ATCC), Daudi (CCL-213, ATCC), CL-01 (Cerutti et al., *J. Immunol.* (1998) 160:2145-2157), the pre B cell lymphoma KM-3/Reh (CRL-8286, ATCC) and the multiple myeloma MC/CAR (CRL-8083, ATCC, grown in IMDM (Invitrogen) supplemented with 20% FCS) were all free of mycoplasma and cultured in a humidified atmosphere at 37° C., using a 5% $CO_2$ atmosphere. The cells were maintained at $2\times10^5$–$1\times10^6$ cells/ml.

Jurkat Cell Membrane Vesicle Preparation

Jurkat cells were harvested by centrifugation at 300×g for 15 min in 500 ml buckets (Corning Inc. Life Sciences, New York, USA), washed in Dulbecco's PBS (Invitrogen), and resuspended in buffer A (1 mM $NaHCO_3$, 1.5 mM MgAc, pH 7.4). Cell concentration was approximately $5\times10^7$ Jurkat cells/ml ($5\times10^9$ cells in 100 ml Buffer A).

Cell disruption was achieved by hypo-osmotic shock treatment (Buffer A) on ice for 10-30 min and subsequent nitrogen cavitation in a Nitrogen cavitation bomb (Parr Instrument Company, Moline, Ill., USA). Cells were kept at a constant pressure of 40 bar (4,000 kPa) for 15 min at 0° C.

Disrupted cells were collected in a 250 ml Sarstedt tube (Sarstedt AG & Co, Numbrecht, Germany) containing 500 µl 0.5 M EDTA to yield a final EDTA concentration of 2.5 mM. Addition of EDTA prevents aggregation of membrane vesicles. The homogenate (100 ml) was divided between 4×25 ml Beckman thick-walled rotor tubes (Beckman Coulter, Inc., Fullerton, Calif., USA), which were centrifuged for 10 min at 1900×g (4,000 rpm in an Sorvall SS34 rotor) at 4° C. to remove unbroken cells, nuclei, and heavy mitochondria.

The supernatant was collected and pelleted material was resuspended in 25 ml of 1 mM $NaHCO_3$ buffer containing 1 mM EDTA and was re-centrifuged (further recovery of pelleted crude Jurkat membranes). Jurkat membranes were pooled with membranes from the first centrifugation. Supernatants containing crude Jurkat membrane vesicles were ultra centrifuged using a Beckman Type 45Ti rotor at 40,000 rpm (approx. 200,000×g) for 2.5 h at 4° C. Supernatants were poured off and remaining buffer was removed by tipping the tube edge against a tissue (e.g. Kleenex™)

The crude membrane pellet was transferred to a Dounce homogeniser with the aid of a metal bar and was resuspended in 2.5 ml HES buffer (10 mM Hepes, 1 mM EDTA, 0.25 M sucrose, pH 7.4) by several careful strokes in the homogenizer. A membrane suspension concentration equivalent of $2\times10^9$ cells/ml containing 80-100 mg protein was, thus, achieved.

Selection of Phage Abs by Whole Cell/Cell Membrane Vesicle Competition Biopanning Approximately $2\times10^{13}$ phage particles were pre-warmed at 37° C. for 15 min with intermittent mixing, centrifuged for 15 min at 14,000×g to remove precipitates, and the supernatant was transferred to a fresh Eppendorf tube. Non-fat dry milk was added to a final concentration of 2% (w/v). Jurkat membrane vesicle preparations derived from $2\times10^9$ cells (round 1 selection; $2\times10^8$ cells round 2 and 3 selections) were thawed on ice, and were mixed with the blocked phage particles. The mixture was incubated for 15 min on ice.

$5\times10^7$ ($5\times10^6$ $2^{nd}$ and $3^{rd}$ rounds) Ramos cells were harvested by centrifugation at 1,200 rpm for 6 min at 4° C. Supernatant was discarded and Ramos cells were resuspended in the milk-phage-Jurkat membrane vesicle mixture. The suspension was incubated at 10° C. under slow end-over-end rotation for 4 h.

The cell/cell membrane vesicle/phage mixture was transferred to a 15 ml Falcon tube (BD Biosciences, Bedford, Mass., USA), containing 0.5 ml 100% (trypan blue stained) Ficoll-Paque PLUS (Amersham Biosciences, Uppsala, Sweden) at the bottom, and 9.5 ml overlaid 40% (v/v) Ficoll in 2% (w/v) BSA/PBS (Ficoll-pillar). The tube was centrifuged at 1,500 rpm for 10 min at 4° C. The tube was removed from the centrifuge and the tube cap was screwed on and sealed airtight.

The bottom "tip" of the Falcon tube containing 100% Ficoll was chopped off using a cigar-chopper. Thus, very high-density material including membrane vesicle sheets and cell nuclei were eliminated from the tube. The tube cap was then carefully opened disrupting the vacuum inside the tube and allowing liquid to be expelled drop-wise through the opening at the (cut off) tube bottom.

The harvested cell suspension was washed once in PBS to remove excess Ficoll. The pellet was resuspended in 1 ml PBS (not performed following final wash) and the suspension was reloaded on top a fresh Ficoll-pillar and the washing procedure was repeated (twice in rounds 2 and 3).

Phage were eluted from cells by addition of 150 μl of 76 mM citric acid (pH 2.5) in PBS followed by incubation at room temperature for 5 min. The mixture was neutralized by addition of 200 μl of 1 M Tris-HCl, pH 7.4. Supernatants containing eluted phage were saved following pelleting of cells at 300×g for 5 min. Further elution of phage was by resuspension and incubation of the cell pellet in 1 ml trypsin at RT for 10 min.

Following inactivation with 40 μl 1 mg/ml aprotinin, cells were centrifuged and supernatant containing eluted phage was saved. Eluted phage were used to infect *Escherichia coli* HB101F' and the bacteria were plated on TB medium containing appropriate antibiotics and glucose. Bacterial colonies were counted, scraped from the plates, and used as inoculums for the next round of panning.

Conversion to scFv Format, scFv Expression, Purification, and Analysis of Cell Binding The phagemid pool obtained following three rounds of selection was digested with EagI to remove the gene III. The resulting vector was re-ligated. Vectors containing re-ligated uncut gene III fragments were linearized by digestion with EcoRI enzyme. The scFv vector pool thus generated was used to transform *E. coli* TOP10 cells essentially as described earlier (Soderlind et al., *Nat. Biotechnol.*, (2000) 18:852-856).

Bacteria were plated on large 500 cm² agar plates and individual clones were picked, transferred to 96-well plates, and expressed in TB medium by over night culture at 37° C., 220 rpm using an automated system (Hallborn, *Biotechniques*, (2002) Suppl:30-37). Recombinant scFv fragments were produced in TB medium containing appropriate antibiotics.

For primary screening of scFv clone binding to target Ramos cells and Jurkat non-target cells, 5,000 Ramos or Jurkat cells were incubated with either of 960 scFv clones, derived from the $3^{rd}$ round of selection and produced as described above. Cells were incubated with 0.5 μg/ml anti-6×His mAb (R&D Systems, Minneapolis, Minn., USA) and 0.7 μg/ml Cy5-conjugated Goat anti-mouse reagent (Amersham Biosciences). Cell binding was analysed in an 8200 Cellular Detection System Fluorescence Macroconfocal High Throughput Screening (FMAT) instrument (Applied Biosystems, Foster City, Calif., USA).

Following primary screening, seventy two bacterial clones were picked randomly (i.e. irrespective of target cell vs. non-target cell reactivity in the primary screening) for DNA sequencing as described previously (Soderlind et al., *Nat. Biotechnol.* (2000) 18:852-856) (Soderlind et al., 2000). For evaluation of cell surface binding by flow-cytometry, Ramos and Jurkat cells (both added at $2\times10^5$ cells per test) were incubated with individual scFv clones at a concentration of 2-10 μg/ml in PBS (Invitrogen) containing 0.5% w/v BSA (DPBS-B) for 1 h.

Cells were washed by centrifugation at 300×g for 6 min. Cells were then incubated with FITC-conjugated CD19 mAb and PE-conjugated CD3 mAb (BD) enabling subsequent identification of target and non-target cells, respectively. Detection of scFv binding was achieved by incubation with RPE-Cy5-streptavidin (Dako Cytomation, Glostrup, Denmark) following incubation with biotinylated anti-6×His mAb. Cells were incubated with secondary and tertiary reagents for 40 min, and 15 min respectively. All incubations were performed on ice using ice-cold solutions.

Differential Whole Cell/Cell Membrane Vesicle Panning

The present study utilized a novel panning protocol to isolate antibodies that target differentially expressed antigens in their native cell surface configuration. Following three rounds of competition biopanning, using whole Ramos B lymphoma cells and membrane vesicles derived from Jurkat T leukaemia cells, recombinant phage scFv were isolated. These were converted to soluble scFv and expressed in *E. coli* TOP10 cells.

Recombinant scFv were incubated with target (Ramos) or non-target (Jurkat) whole cells and examined for cell binding. The specificity for target cell antigens of the antibody clones was striking, since 482 scFv clones expressed were shown to bind selectively to Ramos target cells at intensities ranging from weak to very strong (FIG. 1A). Only two clones were identified that weakly stained non-target Jurkat cells (FIG. 1A).

We next determined the genotype diversity of isolated phage displayed scFv. Seventy-two scFv clones were randomly picked (i.e. irrespective of binding tropism as determined in the primary screening) for DNA sequencing.

The clones were simultaneously re-expressed and re-evaluated for target cell specificity (Ramos vs. Jurkat) by FMAT technology, as described (FIG. 1B). Seven different antibody genotypes were identified, as determined by their different CDRH3 and CDRL3 sequences (data not shown).

The high specificity of anti-Ramos scFv was confirmed by three colour flow-cytometric analysis, following incubation with equal numbers of Ramos and Jurkat cells and detection of scFv binding by means of anti-tag antibody (FIG. 10).

Target and non-target cells were defined by CD19 and CD3 expression, respectively, using fluorochrome conjugated CD specific monoclonal antibodies. The seven genotypically unique scFv clones showed high and variable binding intensities to target Ramos cells, but no binding to the non-target Jurkat cells, as compared to the negative control scFv.

Apoptosis Assay

Lipopolysaccharide levels of recombinantly produced scFv fragments were reduced using Detoxigel columns according to manufacturer's instructions (Pierce Biotechnology, Rockford, Ill., USA). Remaining endotoxin levels were quantified by the LAL-amebocyte lysate assay (Cambrex Bioscience, Walkersville, Md., USA).

All scFv samples were found to contain less than 0.1 IU/ml of lipopolysaccharide. The chimeric anti-CD20 antibody Mabthera™ (Rituximab) was purchased from Lund University Hospital (Lund, Sweden). $2 \times 10^5$ B lymphoma cells (Raji or Ramos) or Jurkat T cells were incubated with serially diluted and detoxified scFv's in culture medium for 1 h on ice.

Cells were sequentially incubated with secondary anti-6× His mAb (5 μg/ml), and tertiary Goat Fab'2 anti-mouse Fab'2 antibody (Jackson ImmunoResearch Laboratories, Inc., West Grove, Pa., USA). Intermittent washings ensured removal of excess unbound antibody reagent. Cells were incubated at 37° C. in a humidified atmosphere of 5% $CO_2$ for 24 h.

When whole IgGs were used for apoptosis induction, cross-linking reagent was replaced by goat Fab'2 anti-human Fc γ antibody (Jackson ImmunoResearch) with minimal cross-reactivity with non-IgG antibody isotypes (to avoid unspecific cross-linking of endogenous B lymphoma associated surface immunoglobulins) and incubated, as described above, for 6 h.

Apoptotic cells were, unless otherwise stated, detected by combined staining with Annexin V Alexa Fluor 488 (AV) and Propidium Iodide (PI) (both from Molecular Probes, Invitrogen) and subsequent flow-cytometric analysis, Cells were defined as viable (AV−/PI−), early apoptotic (AV+/PI−) or late apoptotic/necrotic (AV+/PI+). AV and PI signals were recorded in the FL1 and FL2 or FL3 channels (as indicated in the text), respectively, using a FACSCalibur instrument (BD Biosciences).

In order to investigate the functionality of the isolated scFv we set up a high throughput apoptosis screening assay, based on sequential incubation and washing of cells with scFv and cross-linking reagent. The dependence on scFv clone and concentration in the apoptosis assay is demonstrated in FIG. 2 A-C, where the apoptotic effect of selected scFv clone B1 is compared to the—effect of scFv clone F1 which shows no induction of apoptosis. Jurkat cells lacking target antigen expression did not die from apoptosis after treatment with any of the examined scFv demonstrating that apoptosis induction depended on binding to target antigen (data not shown).

Using the established scFv-apoptosis assay, we screened clones for apoptosis on Ramos and Raji B lymphoma cells. scFv-induced apoptotic effects were compared to that induced by Rituximab anti-CD20 mAb (FIG. 2D). Three scFv clones—B1, B11 and C11—were identified that induced significant apoptosis on both Ramos and Raji cells (FIGS. 2 D and E). Induction of apoptosis by scFv on Raji cells correlated with binding to these cells (FIG. 2D), since scFv clones that failed to bind Raji cells did not induce apoptosis.

The B1, B11 and C11 clones were transferred to fully human IgG1 antibodies. Both their specificity and functionality remained intact after reformatting, as demonstrated by their strong binding and potent cytotoxicity towards a broad panel of B lymphoma cell lines (Table 1). Notably, apoptosis induction was rapid with maximal percentage of annexin V positive apoptotic cells being reached already after three to six hours in several cell lines (Table 1 and data not shown).

IgG Production and Endotoxin Screening Assays scFv antibody fragments were converted to full-length human IgG1λ, format via cloning into a modified pcDNA3 vector (Norderhaug et al., *J. Immunol. Methods* (1997) 204:77-87), and transiently transfected into HEK293 cells using Lipofectamine 2000 reagent according to manufacturer's instructions (Invitrogen).

Human IgG was purified from spent cultivation medium on a MabSelect protein A column (Amersham Biosciences). The purity of preparations was >98% as determined by SDS-PAGE analysis. Antibody preparations were screened and found to contain<0.1 IU/ml endotoxin at concentrations used in the present study, and as determined by the LAL amoebocyte lysate test (Cambrex Bioscience).

Example 2—Analysis of Antibody Specificity

Antigen Identification

The identity of the targeted antigens was determined by immunoprecipitation of B lymphoma cell lysates. Cells ($50\text{-}600 \times 10^6$ per ml lysis buffer, depending on antibody and cell line) were harvested by centrifugation, washed twice in PBS and incubated for 15 min in Lysis Buffer (25 mM Tris-HCl, pH 7.5, 150 mM NaCl, 5 mM EDTA, and Complete EDTA-free Protease inhibitor cocktail (Roche Diagnostics GmbH, Mannheim, Germany)) containing the detergent Triton X-100 (Sigma-Aldrich, St. Louis, Mo., USA) at 0.5% v/v.

Cellular debris was spun down at 16,000×g for 15 min in a conventional table-top centrifuge and the soluble proteins were pre-cleared with Protein A Sepharose 4 Fast Flow (Amersham Biosciences) (1/10 volume of reaction) for 1 h on rotation. For every sample, 1 ml of pre-cleared cell lysate was immunoprecipitated for 2 h by 20-100 μg of any of the human antibodies. Protein A Sepharose 4 Fast Flow was added again and incubated for 30 min, where after the immuno-complexes were washed extensively in lysis buffer, boiled for 5 min, and finally resuspended in Sample Buffer (1× NuPAGE LDS Sample Buffer, 1× NuPAGE Sample Reducing Agent) and separated in a NuPAGE Novex 4-12% Bis-Tris Gel (all from Invitrogen).

After staining (Simply Blue Safestain, Invitrogen), protein bands of interest were excised from the SDS-PAGE and subjected to tryptic digestion, as described (Edvardsson et al., *Electrophoresis* (1999) 20:935-942).

Briefly, gel plugs were destained and equilibrated by washing three times with 200 μl 50% acetonitril (ACN) under agitation. After drying in a SpeedVac concentrator (Savant, Farmingdale, N.Y., USA) for 15 min, samples were reduced by addition of 25 µl 10 mM DTT/100 mM NH₄HCO₃ and incubated for 56° C. for 1 h and alkylated by addition of 25 µl 55 mM iodoacetamide/100 mM NH₄HCO₃ followed by incubation for 45 min at room temperature.

After two additional 10 min washing steps in 100 mM NH₄HCO₃ followed by one wash in 50% v/v ACN, the gel pieces were dried in a SpeedVac concentrator and re-swelled and digested in 15 µl of 15 ng/µl trypsin (Promega Corporation, Madison, Wis., USA) in 25 mM NH₄HCO₃ at 37° C. over night. Peptides were extracted by addition of 50% v/v ACN/1% v/v TFA and 10 min incubation at RT. 1 µl of the extract was spotted onto MALDI sample plates and allowed to dry. 1 µl matrix solution (5 mg/ml alpha-cyano-4-hydroxy cinnamic acid (CHCA) in 75% v/v ACN/1% v/v TFA) was spotted on top of the peptides.

Peptide masses were determined using an Applied Biosystems 4700 Maldi Workstation. The proteins were identified by peptide mass fingerprint database searching using Mascot search tools (Matrixscience, UK). Antigen specificities of clones B10, C10, and G12 were identified using similar methodology, except scFv's and anti-His coated magnetic microbeads (Miltenyi Biotec GmbH, Bergisch Gladbach, Germany) were used for immunoprecipitations.

Following conversion to the full antibody format B1, B11 and C11 IgG were used to precipitate antigens from Raji and Ramos B lymphoma cells. IgG B1 precipitated two bands of approximately 28 and 34 kDa, respectively (FIG. 3A, lane 1). Gel slices containing these bands were prepared and digested with trypsin and analysed by mass spectrometry identifying HLADR/DP as the target antigen.

The specificity of IgG B1 for HLA-DR/DP was verified both by western blotting and detection of HLA-DR/DP protein, using a commercially available monoclonal antibody, and by blocking of B1 IgG binding following pre-incubation of cells with a commercially available HLA-DR specific monoclonal antibody (FIG. 3B).

The identities of the IgG B11 and C11 defined antigens were established using similar methodology. IgG C11 was found to precipitate a 68 kDa protein band identified as the membrane bound form of the B cell receptor µ chain (FIG. 3A, lane 3). IgG B11 precipitated a 90 kDa protein band that was identified as the intercellular cell adhesion molecule-1 (ICAM-1) (FIG. 3A, lane 2). The specificities of IgG B11 for ICAM-1, and of C11 IgG for IgM, were confirmed by MS-MS analysis, antibody blocking studies (FIG. 3B), and western blot analysis (data not shown) using commercially available antibodies.

Specificities of clones B10, C10, and G12 were determined, using scFv and anti-His coated magnetic microbeads for immunoprecipitation. The three scFv clones precipitated a protein band of 68 kDa, and MS-analysis of trypsin digested gel slices containing these bands revealed their specificity for surface IgM. Presumably, these antibodies recognize the Ramos IgM idiotype, since neither of them cross-react with peripheral blood B lymphocytes or other IgM positive B cell lines.

Example 3—Analysis of Antibody Affinities

In Vitro Iodination of B1 and B11 Immunoglobulins

Iodination of 1 mg/ml of IgG₁ B1 or IgG₁ B11 proteins with [$^{125}$I] NaI was performed in PBS for 10 min using Iodogen pre-coated iodination tubes (Pierce). Free [$^{125}$I] NaI was removed by desalting on PD-10 columns (Amersham Biosciences), yielding specific radioactivities in the range of 1000-1600 cpm per ng protein. [$^{125}$I] IgG₁ B1 and [$^{125}$I] IgG₁ B11 was used for determination of antibody affinities.

Determination of IgG B1 and IgG B11 Affinity Constants

Radioiodinated IgG B1 or IgG B11 was incubated with B lymphoma cells in DPBS-B-hIgG (DPBS-B containing 0.2 mg/ml human IgG) for 2 h on ice with intermittent mixing. Non-specific binding was determined in the presence of 0.2 mg/ml unlabelled IgG B1 or IgG B11 protein, as appropriate. Analysis was performed in triplicates.

Cells were loaded on top 40% v/v Ficoll/DPBS-B cushions in individual tubes and were centrifuged at 400×g for 6 min at 4° C. Samples were frozen at −80° C. Cell pellets and cell supernatants were isolated and analysed separately for $^{125}$I-IgG protein content in a gamma counter, following cutting of the tubes in half.

Antibody affinity constants (Kd values) and epitope numbers per cell were determined from Scatchard plot analysis according to Rosenthal et al. (*Anal. Biochem.* (1967) 20:525-532); Bylund and Yamamura (*Methods in Neurotransmitter Analysed*, New York: Raven Press Ltd., 1990); and Marquardt (*J. Soc. Indust. Appl. Math.* (1963) 11:431-441), as previously described (Brix et al., *J. Clin. Invest.* (1998) 102:283-293).

IgG B1 and IgG B11 binding to HLA-DR and ICAM-1 was characterised by incubating the radio-iodinated proteins with Raji or Ramos cells in the presence or absence of 0.2 mg/ml of the corresponding unlabelled IgG protein at 4° C. The specific binding of [$^{125}$I]IgG to the cell surface was calculated by subtracting non-specific binding (binding in the presence of excess unlabelled IgG) from the total binding.

Saturation of specific IgG B1 binding to Raji cells was reached at ~30 nM IgG B1 (FIG. 5). Rosenthal-Scatchard plot analysis revealed a dissociation constant of ~3 nM with 400,000 functional binding sites per Raji cell, assuming a bivalent epitope-IgG interaction (FIG. 5). Similarly, the dissociation constant of IgG B11 was determined to ~0.2 nM with 47,400 receptors per Ramos cell.

TABLE 1

Fully human B1, B11 and C11 IgG antibodies show dynamic binding patterns and induce apoptosis in various B lymphoma cell lines.

| | | Antibody clone—specificity | | | | | | |
|---|---|---|---|---|---|---|---|---|
| | | B1—HLA DR/DP | | B11—CAM-1 | | C11—IgM | | Rituximab—CD20 |
| Tumor classification | Cell line | MFI[b] | Apoptosis Induction[a] | MFI | Apoptosis Induction | MFI | Apoptosis Induction | MFI | Apoptosis Induction |
| Follicular Lymphoma | DOHH-2 | 140 | − | 100 | − | 90 | − | 480 | ++ |
| | WSU-NHL | 280 | + | 0 | − | 60 | − | 790 | + |
| | SC-1 | 170 | + | 0 | − | 50 | − | 50 | − |
| | RL | 50 | − | 100 | − | 210 | − | 200 | + |
| Mantle cell | Granta 519 | 370 | ++ | 260 | + | 60 | + | 360 | +++ |

TABLE 1-continued

Fully human B1, B11 and C11 IgG antibodies show dynamic binding patterns and induce apoptosis in various B lymphoma cell lines.

| | | Antibody clone—specificity | | | | | | | |
|---|---|---|---|---|---|---|---|---|---|
| | | B1—HLA DR/DP | | B11—CAM-1 | | C11—IgM | | Rituximab—CD20 | |
| Tumor classification | Cell line | MFI[b] | Apoptosis Induction[a] | MFI | Apoptosis Induction | MFI | Apoptosis Induction | MFI | Apoptosis Induction |
| Lymphoma | JVM-2 | 650 | + | 100 | − | 10 | − | 520 | + |
| | Rec-1 | 0 | − | 380 | − | 900 | − | 580 | + |
| | SP-53 | 500 | ++ | 90 | − | 360 | − | 740 | ++ |
| | NCEB-1 | 750 | + | 340 | + | 10 | − | 430 | + |
| | Jeko-1 | 1000 | +++ | 30 | + | 1040 | ++ | 1160 | +++ |
| Burkitt's Lymphoma | Ramos | 125 | + | 100 | ++ | 240 | +++ | 300 | +++ |
| | Raji | 550 | +++ | 420 | + | 20 | + | 400 | + |
| | Daudi | 200 | + | 150 | + | 450 | + | 480 | ++ |
| | BJAB | 530 | + | 310 | + | 510 | + | 530 | ++ |
| | CL-01 | 940 | +++ | 600 | ++ | 60 | + | 970 | ++ |
| pre B cell Leukaemia | Reh/KM-3 | 240 | +++ | 20 | − | 0 | − | 0 | − |
| Multiple Myeloma | MC/CAR | 290 | ++ | 120 | + | 0 | − | 110 | − |

[a]Apoptosis Induction; determined by percentage of viable cells after 6 hour incubation with any of the human antibodies, crosslinked with Goat anti-Human (gamma) Fc specific antibody; −, viability not affected; +, 95-80%; ++, 79-60%; +++, 59-40% viable cells compared to control (human FITC-8 IgG$_1$). The results are based on duplicate samples in three independent experiments.

[b]MFI; Mean Fluorescence Intensity of secondary RPE-conjugated Goat anti-Human IgG antibody. The cell line dependent MFI value of control human FITC-8 IgG antibody was subtracted from the MFI of each human antibody.

Example 4—ICAM-1 is a B Lymphoma Associated Antigen with Apoptosis Inducing Properties Flow-Cytometric Analysis of Igg Binding to Ramos Cells Ramos cells (13×10$^6$) were stained with CD45-PerCp-Cy5.5 mAb by incubation on ice for 45 min, washed in DPBS-B, and kept on ice until mixing with unlabelled purified PBLs.

Buffy coats from two healthy volunteers were obtained from the Lund University Hospital. Buffy coats were diluted 1:2 in PBS and washed by centrifugation at 500×g (1500 rpm Beckman Spinchron centrifuge) for 10 min, complete aspiration of the supernatant and resuspension in DPBS containing 1% heat inactivated FCS (DPBS-HI). Washing was repeated twice. Red blood cells were lysed by incubation with red blood cell lysing solution (BD Biosciences) for 15 min at RT. Cells were washed by centrifugation at 60×g (667 rpm Beckman spinchron centrifuge) for 10 min and the supernatant was carefully aspirated. Cells were counted in a Bürker chamber following staining with trypan blue reagent (Invitrogen) and exclusion of dead cells, washed in DPBS-HI, pelleted, and resuspended in DPBS-B containing 200 µg/ml human purified IgG (blocking of Fc receptors).

For each donor and test condition, approximately 2.5×10$^6$ leukocytes were mixed with 1.6×10$^5$ PerCpCy5.5 pre-labelled Ramos cells. Mouse monoclonal CD3-FITC, CD56-PE, and CD19-PerCpCy5.5 antibodies (BD Biosciences) were added and the mixtures were incubated on ice until addition of labelled human IgG. Labelling of n-CoDeR human IgG antibodies and positive control anti-CD20 mouse-human chimeric antibody Rituximab with AF647 Fab fragments (Molecular Probes, Invitrogen) was performed according to manufacturer's instructions.

Briefly, 4 µg of each of IgG B1, B11, C11, and Rituximab antibodies were incubated with 20 µl of AF647-Fab labelling reagent for 5 min at RT. Following addition of 20 µl human IgG blocking reagent and a further incubation for 5 min, AF647-labeled IgG was three-fold serially diluted in DBPS-B, and diluted IgG proteins were added to the mixed Ramos/PBL cell solutions.

Samples were incubated for 1 h, washed, resuspended in DPBS-B, and analysed for binding to different cell subpopulations by flow-cytometry, following appropriate calibration and compensation of the instrument for four-colour analysis. Ramos cells were identified as the PerCpCy5.5$^{high}$ population distinct from the B lymphocyte PerCpCy5.5$^{low}$ population.

Immunohistochemistry

Cryopreserved lymph node biopsies of patients with Anaplastic Large Cell B lymphoma (one patient), Centroblastic/Centrocytic B non-Hodgkin lymphoma (three patients), and B cell chronic lymphocytic leukaemia (one patient) were obtained from the Department of Pathology at Lund University (Lund, Sweden). Eight-micrometer sections of cryopreserved tissue were fixed in acetone for 10 min at 4° C. Endogenous biotin-binding activity was blocked by sequential treatment with Avidin and Biotin (Avidin/Biotin blocking kit, Invitrogen) for 20 min each.

Tissues were incubated with 5 µg/ml control scFv or B11 scFv for 1 h. Following washing, sections were incubated with biotin-conjugated mouse anti-His mAb (R&D Systems) for 30 min. scFv binding was detected following treatment with ABC Complex/HRP reagent (Dako Cytomation) for 30 min, and subsequent incubation with DAB for 5 min.

Sections were photographed using a Leica DC 300F digital camera mounted on top of a Leica DMR light/fluorescence microscope.

Handling of human tissue followed the recommendation of the local Ethics Committee at Lund University Hospital.

Mitochondrial Membrane Depolarisation Assay

Mitochondrial membrane depolarisation was analysed as previously described (Kim et al., *Mol. Biol. Cell* (2004) 15:420-434). Briefly, antibody-treated cells were mixed with JC-1 reagent (Molecular Probes) at 5 µg/ml and incubated for 30 min at RT. Cells were washed twice in ice-cold PBS and resuspended in 300 µA PBS and analysed on a FACS Aria (BD Biosciences). The green and red fluorescence was collected through 494/518 nm (FL-1) and 595/615 nm (FL-2) bandpass filters, respectively.

ICAM-1 is a glycoprotein of the immunoglobulin superfamily (Marlin et al., *Cell* (1987) 51:813-819) capable of inducing bi-directional signalling (Rothlein et al., *J. Immunol.* (1994) 152:2488-2495; Vyth-Dreese et al., *Blood* (1995) 85:2802-2812). ICAM-1 has not previously been demonstrated to be involved in programmed death in B lymphoma cells.

Therefore, we wanted to confirm that IgG B11 induced cell death was an active process, by means other than cell membrane phosphatidyl serine translocation.

Mitochondrial membrane depolarisation was chosen as a validation of apoptosis, since this is a common feature of caspase dependent and caspase independent apoptosis that may be monitored by cell staining with 5,5',6,6'-tetrachloro-1,1',3,3'-tetraethylbenzimidazolyl-carbocyanine iodide (JC-1 reagent).

In accordance with our Annexin V/propidium iodide assay (FIG. 4A, upper panel), IgG B11 was found to induce mitochondrial membrane depolarisation in CL-01 B lymphoma cells, as determined by flow-cytometric analysis following staining with JC-1 reagent (FIG. 4A, lower panel).

In order to exclude the possibility that ICAM-1 expression was an in vitro artefact, resulting from a general up-regulation during cell culture, we examined the binding of IgG B11 to tissue obtained from five different patients with different B lymphoma tumours.

By immunohistochemistry, IgG B11 showed strong binding to the five lymphoma tissues (FIG. 4B), at intensities comparable to, or slightly lower than, the anti-HLA-DR/DP antibody IgG B1 (Table 2).

We next examined the binding of IgG B11 to B lymphoma versus resting peripheral blood leukocytes. Ramos was chosen as a representative B lymphoma cell line, based on its low-end epitope expression yet significant sensitivity to B11 induced apoptosis. Flow-cytometric analysis, following mixed incubation of pre-labelled Ramos cells with whole blood peripheral blood leukocytes and either of IgG B1, B11 or C11 antibodies, revealed that IgG B11 showed strong binding to Ramos cells.

Even more importantly, B11 demonstrated the greatest differential binding (strongest antigen up-regulation) of the three antibodies to Ramos B lymphoma cells versus normal peripheral blood leukocytes (FIG. 4C. and data not shown). IgG B11 binding peaked already at 0.1 µg/ml and was 3.7-fold up regulated on Ramos versus monocyte cells (MFI 654 versus 176), 8.3-fold up regulated on Ramos versus peripheral blood B lymphocytes (MFI 654 versus 78), and 23-fold up regulated compared to NK cells. Binding to other monitored peripheral blood leukocyte subsets was negative.

TABLE 2

ICAM-1 is strongly expressed in B lymphoma tissue of different origin

| Patient | | Antibody clone - specificity | |
|---|---|---|---|
| ID | Tumour classification | B11-ICAM-1 | B1- HLA-DR/DP |
| A | B-CLL[c] (low malignant non-Hodgkin Lymphoma) | + | ++ |
| B | Anaplastic Large Cell B Cell Lymphoma | ++ | +++ |
| C | Centroblastic-Centrocytic B non-Hodgkin Lymphoma | ++/+++ | ++ |
| D | B-CLL/B-PLL[d] | ++ | +++ |
| E | Centroblastic B non-Hodgkin Lymphoma | ++/+++ | +++ |
| F | Centroblastic-Centrocytic B non-Hodgkin Lymphoma | ++ | +++ |

[c]B-CLL = B- Chronic Lymphocytic Leukemia,
[d]B-PLL = B- Pro Lymphocytic Leukemia.
Increasing numbers of + indicate stronger staining.

Example 5—Antigen Distribution of B1, B11, C11 IgG$_1$ on Tumour Cell Lines of Various Origins, as Determined by Flow Cytometry The antigen distribution of human antibody targeted antigens, mainly for B11, on different carcinoma cell lines was investigated. Cells (MCF-7 and MDA MB 435S breast carcinoma, JAR and JEG-3 chorio-carcinoma, A549 lung carcinoma, TCC-SUP urinary bladder carcinoma, MDA MB 435 melanoma, HPAC, PANC-1 and BxPC-3 pancreatic carcinoma, PC-3 and DU145 prostate carcinoma, LS174 T, CaCo$_2$, and Lovo colorectal carcinoma, and THP-1 monocytic leukaemia cells), were washed in PBS, and resuspended at 4×10$^6$ cells/ml in Complete Medium (200,000 cells/50 µA sample). B1 IgG$_1$, B11 IgG$_1$, C11 IgG$_1$, negative control FITC-8 IgG$_1$, and Rituximab anti-CD20 mAb was 3-10-fold serially diluted (10-0.1 pg/ml) in Complete Medium (50 µl/sample). Cells were incubated with either of the antibodies for 1 hour on ice, washed by resuspension in PBS/BSA 0.5%, centrifuged at 1200 rpm for 5 min, and complete aspiration of the supernatants was undertaken. Cells were incubated with PE-conjugated Goat F(ab')2 anti-Human IgG (Caltag Laboratories, Cat no: H10104), diluted 1/50 in PBS/BSA 0.5%, for 30 min, on ice. Following resuspension of in 300 µl PBS/BSA 0.5%, cells were analysed for IgG binding using a FACScan instrument.

PC-3 prostate carcinoma cells showed strong expression of ICAM-1 as demonstrated by the strong binding of B11 IgG to these cells (FIG. 6). MCF-7 breast carcinoma, HPAC pancreatic carcinoma, and LS174 T colorectal carcinoma cells were also found to express ICAM-1 albeit at lower intensity compared to the prostate cancer cells. In contrast, THP-1 monocytic leukaemia cells did not express ICAM-1. All carcinoma cell lines initially tested were found negative for CD20, HLA-DR/DP, and IgM expression as demonstrated by the lack of binding of Rituximab IgG, B1 IgG, and C11 IgG, respectively. Further studies on additional carcinoma cells lines indicated that all carcinoma cells examined were positive for ICAM-1 expression (Table 3).

TABLE 3

ICAM-1 is strongly expressed in carcinoma cell lines of different origin

| Tumor cell type | Cell line | MFI |
| --- | --- | --- |
| Chorio-carcinoma | JAR | 2000 |
| | JEG-3 | 1600 |
| Prostate carcinoma | DU145 | 2200 |
| | PC-3 | 1500 |
| Pancreatic carcinoma | BxPC-3 | 2000 |
| | PANC-1 | 3800 |
| Colon carcinoma | CaCo2 | 800 |
| | Lovo | 1600 |
| Lung carcinoma | A549 | 800 |
| Urinary bladder carcinoma | TCC-SUP | 3200 |
| Melanoma | MDA MB 435 | 4000 |
| Mammary carcinoma | MDA MB 435S | 800 |

Example 6—B11 IgG$_1$ Apoptosis Induction in Carcinoma Cells

B11 IgG$_1$ was shown in example 5 to bind strongly to carcinoma cells. The present example examined the apoptosis inducing properties of this antibody on carcinoma cells.

Cells were seeded in 6 well plates with Complete Growth Medium three days before the onset of the experiment. Cells were between 50-75% confluent at the time of the experiment. Cells were washed with ice-cold PBS and incubated with serially diluted (20-0.02 µg/ml as indicated in the figures, in 1 ml Complete Growth Medium) B11 IgG$_1$, 20 µg/ml control B1 IgG$_1$, 10 µg/ml negative control IgG$_1$ or 10 µg/ml Trastuzumab IgG$_1$ as indicated at 4° C. for 1-2 hours. Cells were washed with ice-cold PBS and secondary F(ab'2) Goat anti-Human F(ab'2) antibody (diluted in Complete Growth Medium to 10 µg/ml) was added. Cells were incubated at 37° C., in a humidified atmosphere of 5% CO$_2$ for 16-24 hours. Total cells were collected by first isolating the supernatant, followed by PBS wash and trypsination of remaining adherent cells. The enzymatic reaction was terminated by resuspension in PBS containing 10% heat-inactivated fetal calf serum. Cells were washed in ice-cold PBS, subjected to Annexin V/propidium iodide staining, and analysed for viability/apoptosis as described in example 5 above.

The B11 IgG$_1$ was shown to induce apoptosis in the carcinoma cell lines in a specific and titratable manner (FIG. 7). Control IgG B1, which did not bind to PC-3 cells (see example 5), also did not induce apoptosis in PC-3 cells. Negative control IgG$_1$ or Trastuzumab IgG$_1$ were not able to induce apoptosis in DU145 or MDA MB435 cells.

Example 7—Pharmaceutical Formulations and Administration

A further aspect of the invention provides a pharmaceutical formulation comprising a compound according to the first aspect of the invention in admixture with a pharmaceutically or veterinarily acceptable adjuvant, diluent or carrier.

Preferably, the formulation is a unit dosage containing a daily dose or unit, daily sub-dose or an appropriate fraction thereof, of the active ingredient.

The compounds of the invention will normally be administered orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the compounds of the invention can be administered alone but will generally be administered in admixture with a suitable pharmaceutical excipient, diluent or carrier selected with regard to the intended route of administration and standard pharmaceutical practice.

For example, the compounds of the invention can be administered orally, buccally or sublingually in the form of tablets, capsules, ovules, elixirs, solutions or suspensions, which may contain flavouring or colouring agents, for immediate-, delayed- or controlled-release applications. The compounds of the invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The compounds of the invention can also be administered parenterally, for example, intravenously, intra-arterially, intraperitoneally, intrathecally, intraventricularly, intrasternally, intracranially, intra-muscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of the compounds of the invention will usually be from 1 mg/kg to 30 mg/kg. Thus, for example, the tablets or capsules of the compound of the invention may contain a dose of active compound for administration singly or two or more at a time, as appropriate. The physician in any event will determine the actual dosage, which will be most suitable for any individual patient, and it will vary with the age, weight and response of the particular patient. The above dosages are exemplary of the average case. There can, of course, be individual instances where higher or lower dosage ranges are merited and such are within the scope of this invention.

The compounds of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or "puff" delivers an appropriate dose of a compound of the invention for delivery to the patient. It will be appreciated that the overall daily dose with an aerosol will vary from patient to patient, and may be administered in a single dose or, more usually, in divided doses throughout the day.

Alternatively, the compounds of the invention can be administered in the form of a suppository or pessary, or they may be applied topically in the form of a lotion, solution, cream, ointment or dusting powder. The compounds of the invention may also be transdermally administered, for example, by the use of a skin patch. They may also be administered by the ocular route, particularly for treating diseases of the eye.

For ophthalmic use, the compounds of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Formulations suitable for topical administration in the mouth include lozenges comprising the active ingredient in a flavoured basis, usually sucrose and acacia or tragacanth; pastilles comprising the active ingredient in an inert basis such as gelatin and glycerin, or sucrose and acacia; and mouth-washes comprising the active ingredient in a suitable liquid carrier.

Generally, in humans, oral or topical administration of the compounds of the invention is the preferred route, being the most convenient. In circumstances where the recipient suffers from a swallowing disorder or from impairment of drug absorption after oral administration, the drug may be administered parenterally, e.g. sublingually or buccally.

For veterinary use, a compound of the invention is administered as a suitably acceptable formulation in accordance with normal veterinary practice and the veterinary surgeon will determine the dosing regimen and route of administration, which will be most appropriate for a particular animal.

Example 8—the Human ICAM-1 Antibody (B11, Also Referred to Herein as BI-505) has Significant Antitumor-Activity Against B Cell Cancer Xenografts Multiple antibodies inducing programmed cell death (PCD) in B cell lymphomas were isolated, targeting different tumor cell-associated surface receptors, by means of a sequential process involving differential biopanning and high-throughput PCD screening of antibodies from the n-CoDeR® human antibody library (FIG. 12A-C). The high specificity for ICAM-1 of BI-505 (also referred to herein as B11) is shown in FIG. 12C. BI-505 dose-dependently induced PCD in ICAM-1-expressing Ramos, Raji and Daudi lymphoma cells (Fransson et al., 2006 and FIG. 13D).

In order to further investigate the therapeutic potential of PCD-inducing ICAM-1 antibodies, BI-505 was screened for in vivo antitumor activity in tumor models comprising SCID mice transplanted with the lymphoblastic cell lines ARH-77 or Daudi. Both cell lines express the CD20 antigen, making it possible to compare antitumor efficacy and potency of antibodies identified here with those of the clinically validated CD20-specific monoclonal antibody rituximab.

Subcutaneous injection of ARH-77 cells resulted in rapid establishment and growth in SCID mice, with tumors being readily palpable between 12 and 14 days. Twice-weekly injections of 20 mg/kg of BI-505 commencing 1 day after tumor cell inoculation prevented tumor growth in 9 out of 10 injected mice (FIG. 14A). Rituximab conferred significant antitumor activity at the same dose, but was less efficacious than BI-505 (FIG. 14A). Furthermore, BI-505 administered at 100 times lower dose (0.2 mg/kg) was equally efficacious compared to 20 mg/kg rituximab in conferring survival (FIG. 14B). The high efficacy and potency of BI-505 was confirmed in mice carrying ARH-77 tumors established for 12 days before start of antibody treatment (FIG. 14C-D). In this model, rituximab failed to reduce tumor growth or promote animal survival ($p>0.05$), while BI-505 both significantly reduced tumor growth (FIG. 14C, $p<0.05$) and prolonged animal survival (FIG. 14D, $p<0.05$). Thus, in this aggressive model of CD20-positive B cell malignancy, BI-505 was more efficacious and more potent in conferring antitumor activity and survival than rituximab.

BI-505's antitumor activity was also tested against Daudi B cell lymphoma xenografts. Again, BI-505 significantly prevented tumor growth (FIGS. 14E and G, $p<0.001$) and prolonged survival (FIGS. 14F and H, $p<0.001$) of tumor-bearing mice when administered one day following tumor cell injection (FIG. 14E-F) or when established tumors were treated (FIG. 14G-H), this time with equal efficacy compared to rituximab (FIGS. 14E-H). The overall stronger antitumor activity of BI-505 compared with rituximab was not caused by a higher number of tumor cell epitopes for BI-505 than for rituximab. In contrast, flow-cytometric analysis revealed that both ARH-77 (FIG. 14I) and Daudi (FIG. 14J) cells expressed significantly fewer BI-505 epitopes than rituximab epitopes, and immunohistochemical analysis of tumor tissue harvested from mice treated with BI-505, rituximab or isotype control antibodies showed that tumors expressed both rituximab and BI-505 epitopes at the completion of experimentation (FIG. 12D).

To establish the potency of B1-505 in vivo and the lowest dose achieving maximal antitumor activity, a dose-titration experiment was performed using the SCID/ARH-77 model system. BI-505 showed dose-dependent antitumor activity, which followed a sigmoidal curve, peaking at the 2 mg/kg dose and remaining near maximal at a dose of 0.2 mg/kg (FIGS. 13A and B). Antibody concentrations in mouse sera were determined by ELISA, and were plotted as a function of maximal in vivo antitumor activity (FIG. 13C). The relationship between BI-505 concentration-dependent in vivo antitumor activity, in vitro antitumor (PCD) activity (FIG. 13D) and in vitro receptor occupancy (FIG. 13E) was then examined by overlaying generated curves in a single graph (FIG. 13F). BI-505 concentration dependent receptor occupancy correlated nearly perfectly with BI-505 in vitro and in vivo antitumor activity (FIG. 13F). This result is consistent with ICAM-1-dependent direct cell cytotoxicity underlying BI-505's antitumor activity.

This concludes that BI-505 confers potent and direct anti-tumor activity against different types of B cell cancer.

Example 9—ICAM-1 and the BI-505 Epitope are Strongly Expressed in Multiple Myeloma It was next evaluated the expression of the BI-505 epitope on bone marrow cells in patients with MM and related diseases (plasmacytoma, plasma cell leukemia, and light chain amyloidosis) by flow cytometry (FIG. 15 and Table 4). Myeloma cells were identified using fluorescent antibodies against surface antigens CD38, CD138, CD45 and CD56 (FIG. 16A) according to European Myeloma Network guidelines on multiparametric flow cytometry in MM (Rawstron et al., 2008) and confirming monoclonal MM cells with intracellular staining of λ and κ light chains. All MM patients expressed the BI-505 epitope on most (97±4%, mean±SD, patient n=22) myeloma cells (FIG. 15 and Table 4). The BI-505 epitope was generally very highly expressed on these cells, with median expression level 10 times higher than on normal B cells from the same patients. Similar results were obtained with a commercially available anti-ICAM-1 antibody (data not shown). Furthermore, the BI-505 epitope was highly expressed on myeloma cells in a patient in relapse who had received several different lines of therapy (FIG. 16B). Thus, ICAM-1 and the BI-505 epitope are strongly expressed on the surface of MM plasma cells.

TABLE 4

Expression of the BI-505 epitope in a cohort of 29 patients with plasma cell disorders.

| | | | | | Patient characteristics | | | | | | |
|---|---|---|---|---|---|---|---|---|---|---|---|
| Patient number[a] | Age (year) | Sex[b] | Ig[c] | M comp (g/L) | Skel. Dest[d] (n) | MM cells[e] (%) | ISS[f] | T[g] (n) | Diagnosis[h] | BI-505 expression Intensity[i] | epitope Positive cells (%) |
| 1 | 38 | M | IgG | 10 | 0 | 14 | I | 0 | MM | +++ | 98 |
| 2 | 46 | M | IgG | 38 | 0 | 34 | II | 0 | MM | +++ | 97 |
| 3 | 53 | F | IgG | 14 | >10 | 6 | I | 0 | MM | +++/++ | 100 |
| 4 | 54 | M | — | — | 3 | 22 | III | 2 | nsMM | +++ | 100 |
| 5 | 59 | M | IgG | 32 | >10 | 29 | I | 0 | MM | ++ | 100 |
| 6 | 60 | F | IgG | 4 | 3 | 2 | II | 1 | MM | +++ | 98 |
| 7 | 60 | F | IgA | 26 | 1 | 10 | I | 0 | MM | +++ | 98 |
| 8 | 61 | M | IgG | 28 | 0 | 23 | II | 0 | MM | +++ | 100 |
| 9 | 62 | M | IgG | 69 | >10 | 30 | II | 0 | MM | ++ | 100 |
| 10 | 62 | F | IgG | 70 | >10 | 80 | III | 1 | MM | + | 95 |
| 11 | 68 | M | IgA | 36 | >10 | 60 | I | 0 | MM | +++ | 100 |
| 12 | 69 | M | — | — | 3 | 50 | I | 1 | nsMM | +++/+ | 95 |
| 13 | 71 | M | IgG | 26 | 0 | 30 | I | 0 | MM | +++ | 100 |
| 14 | 72 | M | IgG | 13 | 0 | 29 | I | 0 | MM | +++ | 100 |
| 15 | 74 | M | IgG | 20 | 0 | 23 | I | 0 | MM | +++ | 100 |
| 16 | 75 | M | IgA | 40 | 0 | 78 | II | 0 | MM | ++ | 88 |
| 17 | 77 | M | IgG | 45 | 0 | 34 | II | 0 | MM | +++ | 100 |
| 18 | 79 | F | IgG | 23 | 0 | 16 | I | 0 | MM | +++ | 100 |
| 19:1 | 79 | M | IgG | 24 | 7 | 50 | III | 0 | MM | +++ | 93 |
| 19:2 | 79 | M | IgG | 3 | n/a | n/a | — | 1 | MM | +++ | 95 |
| 19:3 | 80 | M | IgG | 3 | n/a | 16 | — | 2 | MM | +++ | 91 |
| 20 | 82 | M | IgA | 29 | 0 | 44 | III | 0 | MM | +++ | 100 |
| 21 | 83 | F | IgG | 39 | 0 | 89 | III | 0 | MM | +++ | 93 |
| 22 | 84 | M | IgA | 17 | 0 | 38 | III | 0 | MM | +++ | 86 |
| 23 | 61 | M | IgA | 7 | 2 | 24 | — | 0 | AL | ++ | 97 |
| 24 | 64 | F | — | — | n/a | 6 | — | 0 | AL | +++ | 100 |
| 25 | 72 | F | — | — | 0 | 1 | — | 0 | LCDD/MM | +++ | 98 |
| 26 | 61 | F | IgA | 42 | n/a | 80 | — | 4 | PCL | +++ | 76 |
| 27 | 75 | M | IgG | 18 | >10 | 8 | — | 4 | PCL | + | 77 |

TABLE 4-continued

Expression of the BI-505 epitope in a cohort of 29 patients with plasma cell disorders.

| Patient number[a] | Age (year) | Sex[b] | Ig[c] | M comp (g/L) | Skel. Dest[d] (n) | MM cells[e] (%) | ISS[f] | T[g] (n) | Diagnosis[h] | BI-505 expression Intensity[i] | epitope Positive cells (%) |
|---|---|---|---|---|---|---|---|---|---|---|---|
| 28 | 52 | M | IgG | 1 | 1 | 5 | — | 1 | PC | +++ | 93 |
| 29 | 60 | F | IgG | 4 | 1 | 2 | — | 1 | PC | +++ | 100 |

[a]Corresponds to number found in FIG. 3.
[b]M (male); F (female).
[c]Immunoglobulin class of M-component.
[d]Number of skeletal destructions.
[e]Multiple myeloma cells counted as % of all nucleated cells in bone marrow smears.
[f]International Staging System of MM.
[g]Number of different MM treatment regimens before BI-505 analysis.
[h]MM (multiple myeloma); nsMM (non-secretory multiple myeloma); AL (amyloid light chain amyloidosis); LCDD (light chain deposit disease); PCL (plasma cell leukemia); PC (plasmacytoma).
[i]Measured by FACS on MM cells. Two patients (no 3 and 12) had two MM cell populations with differential BI-505 expression.

Example 10—BI-505 has Broad Anti-Myeloma Activity In Vivo

Since high expression of the BI-505 epitope in human MM was found, BI-505 was screened for in vivo anti-myeloma activity using SCID/xenograft models comprising four well-characterized MM cell-lines. These cell lines express the myeloma markers CD38 and CD138 but do not express CD20. Twice weekly dosing with 2 mg/kg of BI-505 starting one day after tumor cell injection reduced myeloma tumor growth in mice xenografted with ICAM-1-expressing cell lines EJM, RPMI-8226, and NCI-H929 by 98%, 96%, and 99%, respectively (FIGS. 17A and B). In contrast, BI-505 did not affect tumor growth in mice xenografted with the ICAM-1-negative cell line OPM-2 (FIGS. 17A and 4B). Taken together, these studies indicated that BI-505 had highly efficacious, broad, and ICAM-1-dependent in vivo anti-myeloma activity.

Example 11—BI-505 has Potent Anti-Myeloma Activity in Clinically Relevant Models of Advanced Myeloma To assess the therapeutic potential of BI-505 for treatment of MM, the anti-myeloma effects of BI-505 were compared to current gold-standard treatment in disseminated experimental models of MM sharing characteristics with human disease. These models resemble the manifestation and progression of human MM disease in many respects, including tumor dissemination and establishment in bone marrow, and the appearance of osteolytic bone-lesions and hypercalcemia (Mitsiades et al., 2003; Yaccoby et al., 1998). Firstly, the anti-myeloma activity of BI-505 was compared with currently used treatments in an advanced disseminated MM model comprising RPMI-8226 myeloma cells. In this model, therapeutic treatment with 2 mg/kg BI-505 was started five days after intravenous grafting of MM cells to allow for homing and establishment of MM cells in bone marrow. BI-505 significantly enhanced survival and delayed disease onset compared to treatment with the comparator drugs bortezomib, lenalidomide, melphalan or dexamethasone (FIG. 18A), all approved and currently used for MM therapy. Importantly, FIG. 18A shows the effect of the comparator drugs used at maximally efficacious, and clinically relevant, doses. Higher doses of some of the comparator drugs were shown to be toxic, but not more efficacious, to animals (data not shown).

Primary human MM cells depend on interactions with bone marrow stromal cells to proliferate and survive. The SCID-hu mouse harbors a human microenvironment where primary patient MM cells proliferate and induce pathology similar to human clinical MM (Yaccoby et al., 1998). MM cell derived human IgG titers were detected (>10 µg/ml) in the serum of SCID-hu mice four weeks after implantation of human MM cells to transplanted human bones, at which time treatment with antibodies (2 mg/kg) or bortezomib (1 mg/kg) began. Human IgG titers increased steadily in control treated SCID-hu mice over the course of experimentation to reach maximal concentrations of 40±5 µg/ml just before sacrifice (FIG. 18B and FIG. 19). In contrast, therapeutic treatment with BI-505 or bortezomib halted or reduced serum human IgG levels to below pre-treatment levels ($hIgG_{BI-505}$=91±22%) demonstrating a significant anti-MM effect. Two independent experiments were performed with similar results (FIG. 18B and FIG. 19), each with MM cells from two different patient donors (n=4). Immunohistochemical staining for human CD138 expressing cells in harvested human bone implants indicated that BI-505 anti-myeloma effects correlated with decreased tumor burden (FIG. 18C). BI-505 anti-myeloma effects correlated with protection against MM-induced bone pathology as demonstrated by decreased bone remodeling with decreased loss of bone mineral density (FIG. 18D). Staining of a limited number of bone sections indicated reduced numbers of bone osteoclasts (FIG. 18E) and total infiltrated nucleated cells (FIG. 18F) in BI-505 or bortezomib treated mice compared to control-treated mice.

Thus, in two clinically relevant experimental models BI-505 anti-MM activity was equal to or greater than currently available drugs.

Example 12—BI-505 Confers Fc-FcγR Dependent Antitumor Activity Through Macrophages Previous studies have demonstrated PCD-inducing properties of BI-505 in a wide range of tumor B cell lines (Fransson et al., 2006). BI-505 PCD was enhanced by antibody cross-linking in vitro, indicating that in vivo antitumor activity might be enhanced by cross-linking provided by FcγR-expressing cells (Wilson et al., 2011). Given the critical importance of FcγR-mediated antitumor mechanisms for the clinical and in vivo therapeutic activity of clinically validated cancer mAbs (Clynes et al., 2000; Musolino et al., 2008; Weng and Levy, 2003), the contribution of antibody Fc: host FcγR-dependent mechanisms for BI-505's therapeutic activity was addressed. To this end BI-505 variants with abolished (IgG$_{1\ N297Q}$, "Fc-mut"), or reduced (BI-505-IgG$_4$) FcγR-binding compared to wildtype BI-505 IgG$_1$ were engineered, and their respective in vivo therapeutic activities investigated. The Fc-switch variants retained affinities for ICAM-1 as evidenced by near identical EC$_{50}$ values for binding to recombinant or cell-surface-expressed ICAM-1 (FIG. 21A-C). The in vivo antitumor activity of BI-505 Fc-variants (FIG. 20A) correlated perfectly with binding to mouse FcγRIV (FIG. 20B)—the structural and functional homologue of human FcγRIIIa and a principal murine FcγR conferring antibody mediated cell cytotoxicity in vivo (Nimmerjahn et al., 2005)—increasing in the order of IgG$_{1\ N297Q}$<IgG$_4$<IgG$_1$. Importantly, mice treated with IgG$_1$, IgG$_4$, and IgG$_{1\ N297Q}$ variant antibodies of BI-505 had similar serum antibody titers at the end of experimentation, indicating that the different antibody variants had similar in vivo half-lives and demonstrating that differential antitumor activity did not result from differential pharmacokinetics (Table 5). These findings demonstrated that BI-505 in vivo antitumor activity was Fc: FcγR-dependent.

TABLE 5 related to FIG. 20. In vivo serum concentrations (μg/mL) of IgG$_1$, IgG$_4$ and IgG$_{1\ N297Q}$ variants of BI-505

| Dose (mg/kg) | IgG$_1$ | IgG$_4$ | IgG$_{1\ N297Q}$ |
|---|---|---|---|
| 2 | 20 ± 2.9 | 13 ± 3.1 | 9.6 ± 3 |
| 0.2 | 1.2 ± 0.4 | ND | ND |
| 0.02 | 0.06 ± 0.02 | ND | ND |

ND = not determined

Fc-FcγR-interactions, in addition to enhancing antibody induced negative signalling and tumor PCD (Wilson et al., 2011), may involve both innate and adaptive arms of cellular immunity (Alduaij and Illidge, 2011; Park et al., 2010). Different approaches to assess the role of NK cells and macrophages were used—two principal cell types capable of conferring FcγR dependent antitumor effects—for BI-505 therapeutic activity; Firstly, the relative abundance of these cell types in tumor tissue harvested from BI-505 or control antibody treated mice were examined. By immunohistochemistry, it was found that macrophages (F4/80$^+$ cells) constituted the vast majority of FcγR expressing cells in BI-505-treated tumors (FIG. 20D). In contrast, very few intratumoral NK cells could be detected (CD49b$^+$ CD31$^-$ cells). Furthermore, and interestingly, treatment with BI-505 significantly increased tumor macrophage infiltration, but—conversely—decreased tumor NK cell content (FIG. 20D). Together, these data suggested that macrophages, but not NK cells, were principal FcγR-expressing cells conferring BI-505 antitumor activity in vivo. To verify this macrophages or NK cells were depleted, using clodronate liposomes and anti-asialo antibodies respectively, from SCID mice bearing established RPMI-8226 myeloma tumors and examined the effect on BI-505 anti-myeloma activity. A period of three weeks of macrophage and NK cell depletion was chosen as read out since this was the longest time-period where neither treatment affected animal well-being. Cell depletion did not per se impact tumor growth over this period of time (FIG. 21D-E). FIG. 20E clearly demonstrates that macrophage depletion completely abolished BI-505 in vivo antitumor activity. Tumors of macrophage depleted BI-505 treated mice had doubled in size compared with tumors from animals receiving BI-505 treatment alone (V$_{BI-505}$=95±39 mm$^3$, V$_{BI-505+clodro}$=189±94 mm$^3$, p<0.001), but were similarly sized compared to tumors from control antibody treated mice (V$_{ctrl\ IgG}$=198±90 mm$^3$, p>0.05). NK cell depletion, in contrast, had little or no effect on BI-505 antitumor activity. Tumor volumes of NK cell depleted BI-505 treated mice were not significantly different from mice treated with BI-505 only (V$_{BI-505}$=95±39 mm$^3$, V$_{BI-505+asialo}$=130±53 mm$^3$, p>0.05), but significantly smaller compared to control antibody treated animals (p<0.01, FIG. 20E). BI-505 also had significant antitumor activity in two different aggressively growing NK cell deficient MM mouse models comprising RPMI-8226 or U266 cells grafted to NOD/Shi-scid/IL-2Rγ$^{-/-}$ mice (FIGS. 20E-G). Taken together, the data identify macrophages, but not NK cells, as critical effector cells conferring BI-505 FcγR-dependent in vivo antitumor activity.

Next investigated was BI-505's ability to mediate Fc:FcγR-dependent macrophage phagocytosis (ADCP; Antibody-dependent cell phagocytosis) of human MM cells in vitro. As expected, BI-505 IgG$_1$ bound to human FcγR (FIG. 20C) and conferred ADCP of both RPMI-8226 and primary patient's MM cells (FIG. 20 H-I) in the presence of human macrophages. In contrast, FcγR-binding deficient BI-505 IgG1$_{N297Q}$ did not bind to human FcγR (FIG. 20C) and did not confer ADCP of targeted MM cells (FIG. 20 H-J). Similarly, pre-incubation with recombinant soluble Fc gamma receptor diminished BI-505 IgG$_1$-mediated ADCP (FIG. 20J). Analogous to the in vivo setting, therefore, BI-505-mediated ADCP in vitro was Fc: Fc gamma receptor dependent.

Also examined was the ability of BI-505 to mediate ADCC against human target tumor cells in the presence of human effector NK cells. BI-505 conferred cytotoxicity in an Fc-dependent manner, although ADCC activity by effector NK cells was less pronounced compared with macrophage mediated ADCP (data not shown).

Besides Fc:FcγR-dependent antitumor mechanisms, cancer mAb Fc-dependent antitumor activity may result from activation of the complement cascade by complement-dependent cytotoxicity (CDC). We therefore examined the ability of BI-505 to induce CDC in a panel of ICAM-1-expressing tumor cell lines. However, BI-505 did not induce CDC in any of the tumor cell lines monitored (data not shown). In contrast, treatment with the positive control rituximab effectively induced CDC, as has previously been reported (Cragg and Glennie, 2004; Cragg et al., 2003; Manches et al., 2003).

In summary, the data provides strong evidence for Fc:FcγR-dependent anti-tumor mechanisms e.g. macrophage mediated ADCP and FcγR cross-linking induced antibody tumor PCD underlying BI-505's therapeutic activity.

Example 13—Safety Profile of the BI-505 Antibody

In addition to exerting significant antitumor activity, a therapeutic cancer antibody must be safe and tolerable for patients. Toxicology studies in relevant animal species may provide important information on drug safety. BI-505 does not, however, cross-react with ICAM-1 from animals that are commonly used for toxicological evaluation (data not shown). The non-clinical safety assessment therefore focused on evaluating its effects on viability and function of human normal (untransformed) cells expressing ICAM-1.

Based on BI-505's documented ability to confer Fc:FcγR-dependent antitumor activity in malignant B cells, and a proposed general negative role for complement activation with regard to antibody tolerability (Lim et al.; van der Kolk et al., 2001), direct cytotoxic effects (PCD, ADCC, and CDC) of BI-505 in ICAM-1-expressing human peripheral blood B cells and endothelial cells were examined. Whereas peripheral blood B cells and naïve B cells show low endogenous expression of the BI-505 epitope (Fransson et al., 2006), human umbilical vascular endothelial cells (HUVECs) and human microvascular endothelial cells (HMVECs) cells showed significant ICAM-1 expression, which was further upregulated in response to IFN-γ stimulation as determined by flow-cytometric analyses (FIG. 22). However, BI-505 did not induce cell death in any of the resting or activated normal ICAM-1-expressing cell types that were examined, irrespective of whether antibody was cross-linked or not to mimic Fc:FcγR-cross linking in vivo (FIGS. 23A-C and 23G). In contrast, treatment of endothelial cells with paclitaxel and treatment of B cells with positive control anti-HLA-DR or anti-CD20 antibody induced significant PCD (FIGS. 23A and 23G).

Cytokine release and T cell proliferation are thought to be common causes of mild and severe adverse reactions to antibody therapy. In order to further investigate any undesirable effects of BI-505 on ICAM-1 expressing immune cells, we therefore assessed putative effects of BI-505 on peripheral blood mononuclear cell (PBMC) cytokine release and T cell proliferation. In order to maximize the chances of identifying any PBMC-agonistic properties of BI-505, we used two different antibody-coating protocols in which the antibody was hyper-cross-linked as previously described (Stebbings et al., 2007). BI-505 immobilized by either protocol induced PCD in Daudi lymphoma cells, demonstrating that biological activity was retained following immobilization (data not shown). BI-505 did not, however, induce PBMC cytokine release and did not induce T cell proliferation by either immobilization protocol, or when added in solution in the presence or absence of cross-linking reagent (FIG. 23D-F).

In contrast and as expected, incubation of PBMCs with an immobilized positive control anti-CD3 antibody resulted in significant release of IL-1β, IL-2, IL-6, IL-8, TNF-α and IFN-γ (FIG. 23D). Analogous experiments demonstrated that BI-505 added in solution did not induce or enhance cytokine release from resting or lipopolysaccharide prestimulated PBMCs and did not induce T cell proliferation (FIGS. 23E and F).

Taken together therefore, no evidence was found for undesirable activation or cytotoxicity of BI-505 against ICAM-1 expressing immune cells. Together with limited safety studies in rat, rabbit and monkey, demonstrating no compound-related off-target toxicity (data not shown), and indicating a long half-life typical of that for a human IgG (i.e. 12-13 days in rat [Table 6], corresponding to 2-3 weeks in man), these observations indicated a therapeutically relevant safety profile and pharmacokinetics of BI-505.

Table 6 shows BI-505 pharmacokinetics following a single IV injection of 0.5 mg/kg, 2.5 mg/kg, and 10 mg/kg of BI-505. $AUC_{0-tlast}$=area under the serum concentration-time curve from time zero to last quantifiable concentration; $AUC_{0-\infty}$=area under the serum concentration-time curve from time zero to infinity; $C_{max}$=maximum observed serum concentration; $t_{max}$=time of maximum observed serum concentration; $t_{1/2}$=apparent terminal elimination half-life; CL=total serum clearance; $V_{ss}$=apparent volume of distribution at steady-state; $V_z$=apparent volume of distribution during the terminal elimination phase. There were six animals per sex and treatment group.

Example 14—Summary of Finding from Examples

The inventors show the successful application of a function-first approach to therapeutic antibody discovery, resulting in the isolation of a human ICAM-1 antibody based on its (I) specificity for a surface receptor upregulated on tumor B cells, (II) significant tumor programmed cell death inducing properties and (III) significant in vivo anti-tumor activity against human B cell tumors. Thus, this functional screening methodology was successfully applied both to identify a function (induction of PCD in tumor cells) of a well-characterized receptor (ICAM-1) and a human antibody against the same target with significant therapeutic potential.

The function-first approach to antibody discovery offers several advantages over and differs in several respects from conventional approaches in which antibodies are identified based on specificity for a predefined target structure. By combining powerful differential biopanning of a naïve human antibody library with high-throughput tumor cell death screening, this discovery platform enables the simultaneous generation of multiple high-affinity antibodies with therapeutic potential and specificity for different tumor cell-associated receptors. The value of screening for functionality across different specificities has been indicated by previous studies, which collectively demonstrate that antibodies against different tumor-associated cell surface receptors can have significant antitumor activity against the same cancer cell type (for a review see (Cheson and Leonard, 2008)). Thus, in a highly diversified antibody source such as n-CoDeR®, the most therapeutically efficacious, potent, and best-tolerated antibodies with respect to a given type of cancer could be specific for one of several receptors, and identifying the optimal antibodies requires functional screening of antibodies targeting all such receptors.

The predictive value of tumor PCD as an indicator of an antibody's therapeutic potential was demonstrated by the enhanced in vivo antitumor activity of BI-505 (as well as of several other antibodies isolated through this approach; unpublished data) against CD20-expressing tumors, compared to rituximab. Cragg and Glennie (Cragg and Glennie, 2004) further indicate the importance of using a function-

TABLE 6 related to FIG. 23. BI-505 pharmacokinetics in the rat

| Dose (mg/kg) | Gender | $t_{max}$ (hr) | $C_{max}$ (µg/mL) | $AUC_{0-tlast}$ (µg·hr/mL) | $AUC_{0-\infty}$ (µg·h/mL) | $t_{1/2}$ (hr) | CL (mL/min/kg) | $V_z$ (L/kg) |
|---|---|---|---|---|---|---|---|---|
| 0.5 | Males | 0.250 | 14.3 | 1460 | 2030 | 283 | 0.00410 | 0.101 |
|  | Females | 0.250 | 14.5 | 1420 | 2020 | 281 | 0.00412 | 0.100 |
| 2.5 | Males | 1.00 | 54.6 | 6810 | 10100 | 309 | 0.00414 | 0.111 |
|  | Females | 0.250 | 65.2 | 5970 | 8440 | 284 | 0.00494 | 0.122 |
| 10 | Males | 0.500 | 281 | 29300 | 43100 | 314 | 0.00386 | 0.105 |
|  | Females | 0.500 | 279 | 25800 | 36200 | 294 | 0.00461 | 0.117 | first approach and of screening for tumor PCD; Different antibodies, which bound with similar affinity to CD20 and had identical Fc regions, differed greatly in their therapeutic efficacy in vivo and, intriguingly, conferred antitumor activity by different mechanisms of action. Superior therapeutic activity correlated positively with tumor PCD and inversely with complement-dependent tumor cell cytotoxicity (Beers et al., 2008; Cragg and Glennie, 2004). These and other observations highlight the importance of the function-first approach to identify antibodies with therapeutic activity (Beck et al.; Gan et al., 2009; Ivanov et al., 2009). The use of cancer cells, which express targeted antigens in their true cell surface configuration, will increase the likelihood of identifying antibodies with specificity for functional and disease-associated receptor epitopes compared to conventional techniques using recombinant antigen or transfected cells in the panning process. Finally, it is generally thought that therapeutic targets are limited and that most might already be identified. From this perspective, it is noteworthy that this technology can reveal functions of previously well-characterized receptors, indicating their suitability as targets in previously unrecognized indications and expand the "therapeutic target space". Thus, while the well-characterized role of ICAM-1 in inflammation has provided the rationale for anti-ICAM-1 targeted intervention of acute and chronic inflammatory disorders (Kavanaugh et al., 1997; Mileski et al., 2003; Schneider et al., 1998), the inventor's findings identify ICAM-1 as a promising target in multiple MM, and oncology in a broader sense. Taken together, this function-first approach provides a unique, effective, and complementary strategy to generation of anti-tumor antibodies such as BI-505.

Several observations suggest that ICAM-1 may be a suitable target for cancer, particularly MM, immunotherapy. Strong expression of ICAM-1 is associated with advanced disease, poor survival, and resistance to chemotherapy (Sampaio et al., 2009; Schmidmaier et al., 2006; Zheng et al., 2012), which is the current inevitable end-stage of MM (Kyle and Rajkumar, 2004). Consistent with these observations, we demonstrate that a majority of MM cells express high levels of the epitope targeted by BI-505. High and homogenous expression on the tumor cell surface, and upregulated expression in conjunction with disease progression and the development of resistance to chemotherapy, are hallmarks of targets suitable for therapy with antibodies that confer direct tumor cell cytotoxicity. The antitumor activity of BI-505 correlated with antibody binding to tumor cell-expressed ICAM-1 and was shown to be Fc:FcγR-dependent. Accumulating evidence suggest that interactions between an antibody's constant domain (Fc) and a host's Fc gamma receptors (FcγR) are instrumental in the therapeutic efficacy of rituximab and other approved anti-cancer antibodies (Bibeau et al., 2009; Lejeune et al., 2008; Musolino et al., 2008; Weng and Levy, 2003; Zhang et al., 2007) via mechanisms that may involve both innate and adaptive immunity (Alduaij and Illidge, 2011; Park et al., 2010), as well as enhanced tumor PCD following FcγR-dependent cross-linking of tumor bound mAb (Wilson et al., 2011).

Consequently, while there is currently no antibody available to treat MM, non-clinical and clinical studies on antibodies approved for treatment of different types of cancer suggest that those—like BI-505—that are capable of triggering MM cell death via Fc:FcγR-dependent immunity hold particular promise of improving MM survival.

The inventors have shown herein that macrophages are principal effector cells conferring BI-505 FcγR-dependent antitumor activity. Macrophages are abundantly present in MM bone marrow and accumulating data point to a detrimental role for macrophages and ICAM-1 in MM development of drug resistance (Zheng et al., 2009; Zheng et al., 2012). BI-505 harnessing of tumor-associated macrophages to confer antitumor activity thus is an attractive mechanism of combating cancer such as MM.

In addition to exerting significant antitumor activity, a therapeutic cancer antibody must be safe and tolerable for patients. Previous studies by independent investigators demonstrated that treatment with (a murine) anti-ICAM-1 antibody was well tolerated by different patient groups (Kavanaugh et al., 1997; Mileski et al., 2003; Schneider et al., 1998). Herein presented data on BI-505 is consistent with this notion. Owing to its fully human nature, and as indicated from the inventor's animal studies, BI-505 should have low immunogenicity.

Collectively, these results demonstrate proof-of-principle for the function-first approach in the search for efficient antitumor antibodies, and provide a rationale for further pre-clinical and clinical evaluation of BI-505 in the treatment of MM. An open label multicenter phase I dose-escalation study with BI-505 in relapsed/refractory MM patients, approved by the Swedish Medical Product Agency and in accordance with the United States Food and Drug Administration's (FDA) guidance, is ongoing (NCT01025206, http://clinicaltrials.gov/).

Example 15—Experimental Procedures for Examples 8-12

Cell Culture and In Vitro Assays

ARH-77, RPMI-8226, and Daudi cell lines were obtained from the American Type Culture Collection (ATCC, Sweden). NCI-H929, EJM, and OPM-2 cell lines were obtained from the Deutsche Sammlung von Mikroorganismen and Zellkulturen (DSMZ, Germany). HUVEC and HMVEC cells were obtained from Cascade Biologics (Portland, Oreg., USA). All cells were maintained in culture media as recommended by the supplier and maintained at 37° C. in a 5% $CO_2$, 95% humidity incubator. Cell PCD, ADCC, CDC, cytokine release and T cell proliferation assays were performed as described elsewhere (Fransson et al., 2006) and Supplemental Information).

Patient Cell Studies

Plasma cell surface expression of ICAM-1 and the BI-505 epitope was analyzed by FACS. Bone marrow aspirates were obtained from 29 patients diagnosed with MM or related diseases at the Department of Hematology, Skånes University Hospital, Lund. All human samples were collected using protocols approved by the Ethics Committee of Skåne University Hospital, and informed consent was obtained from all patients.

Animal Studies

All studies were conducted in accordance with guidelines of the Lund University Hospital, Sweden or University of Utah, Salt Lake City, USA following approval from the local ethical committee for animal care and use. BI-505 efficacy and potency was examined in subcutaneous and disseminated, prophylactic and therapeutic, experimental MM models comprising myeloma cell lines RPMI-8226, U266, EJM and OPM-2. The in vivo efficacy of BI-505 was compared to clinically approved drugs dexamethasone, melphalan, bortezomib and revlimid used at clinically relevant doses in therapeutic disseminated models comprising RPMI-8226 or primary patient myeloma cells, the latter following injection of patient cells in implanted of human fetal bone in SCID mice. For subcutaneous grafting, $1\text{-}5\times10^6$ tumor cells (RPMI-8226, NCI-H929, EJM, OPM-2, ARH-77, or Daudi) were subcutaneously injected at a volume of 100 μl into the left flank of anesthetized mice as described in the Supplemental Information. For established xenograft studies, when tumors reached an average size of 80-120 mm$^3$, animals were sorted to give nearly identical group mean tumor sizes, and were treated with isotype control antibody (20 mg/kg/inj), rituximab (20 mg/kg/inj), or BI-505 antibody (0.02 to 20 mg/kg/inj, as indicated in the text) intra-peritoneally (i.p.) twice weekly until study termination. For disseminated experimental models of MM, RPMI-8226 (10×10$^7$ tumor cells) were injected intravenously (i.v.) into the caudal vein of anesthetized mice after whole-body irradiation (1.8 Gy, $^{60}$Co, INRA, Bretennieres). Treatment with saline, isotype control IgG, bortezomib, lenalidomide, dexamethasone, or BI-505 started on day 5 (RPMI-8226). Treatment with melphalan started on day 10. BI-505 or isotype IgG mAb was administered i.v. at 2 mg/kg/inj twice weekly for 8 weeks; bortezomib at 1 mg/kg/inj once weekly for 8 weeks; lenalidomide orally at 2 mg/kg/inj for 2 cycles consisting of 5 days of treatment and 2 days of wash out; melphalan i.v. at 3 mg/kg/inj once weekly for 8 weeks; and dexamethasone at 6 mg/kg/inj three times weekly for 2 weeks. In vivo mechanistic studies assessing the role of Fc-FcγR interactions utilised wild-type and engineered FcγR-binding deficient (N297Q) IgG1 variants of BI-505. The role of macrophages and NK cells for BI-505 in vivo antitumor activity was assessed using anti-asialo antibody treatment, clodronate liposome treatment or NK-cell deficient mice. For a detailed description of in vivo studies see Supplemental Information.

In Vitro Functional Studies

Peripheral blood derived monocytes, NK cells, B cells and T cells were purified from buffy coats from healthy donors obtained from the local blood central at Lund University Hospital and Halmstad Hospital. Briefly, PBMCs were first extracted using Ficoll-Paque PLUS (GE Healthcare Life Sciences), followed by isolation of monocytes with CD14 MicroBeads and MACS separation (Miltenyi Biotec). Monocyte-derived macrophages were generated by 6-14 days culture in the presence of 25 ng/mL of recombinant human M-CSF (R&D Systems). For multiple myeloma cells, freshly isolated bone marrow samples were donated by patients at Lund University Hospital and subsequently processed with Ficoll-Paque PLUS. Negative isolation of malignant plasma cells was performed using Plasma Cell Isolation Kit II (Miltenyi Biotec).

ADCP

Cultured macrophages were detached and plated in flat 96-well plates at 50 000 cells/well and placed in 37° C. CFSE-stained target cells were incubated with antibodies for up to 1 hr on ice. After washing, the different cell solutions were added to the culture plates containing macrophages at a ratio of 5:1 (Target cells:Macrophages). Thereafter, the culture plates were incubated at 37° C. for 1-2 hr (primary patient MM cells) or 16 hr (RPMI-8226 cells). The percentage of macrophages that had phagocytosed tumor cells (CFSE$^+$, CD206$^+$) per total analyzed macrophages was determined following gating and acquisition of 5000 CD206$^+$ cells/sample.

ADCC

NK cells were isolated from purified PBMCs using positive or negative NK cell-isolation kits (Miltenyi Biotec). Target cells were harvested and incubated in medium with or without the respective antibodies (2 μg/mL) for 60 min on ice before. NK cells were washed, diluted in ADCC medium and dispensed together with the respective antibody-coated target cells at varying effector/target cell ratios. All experiments were performed in triplicate. After incubation, TO-PRO-3 dye and counting beads (Invitrogen) were added and cells were analyzed for membrane permeabilization using flow cytometry.

CDC

Target cells were harvested as described above (under ADCC heading) and incubated with antibodies at 5 μg/mL for 60 min on ice and then washed. Human serum, normal or heat-inactivated (Sigma, Sweden), was added to tubes and the samples were incubated for 2 hr at 37° C. After completion of incubation, ToPo-Pro-3 (Invitrogen) was added at a final concentration of 0.3 μM and cells were analyzed for membrane permeabilization using flow cytometry.

Detailed experimental procedures including protocols for assessment of apoptosis in normal ICAM-1 expressing endothelial cell, T cell proliferation, PBMC cytokine release and receptor occupancy studies are described in the following Supplemental Experimental Procedures section:

Supplemental Experimental Procedures

Reagents, Cells, and Animals

Several batches of IgG$_1$ BI-505 were either stably expressed from CHO cells or produced transiently in HEK293 cells. IgG$_4$ and IgG$_{1\ N297Q}$ variants of BI-505 and the control antibodies IgG$_1$CT17 and IgG$_1$FITC-8GA were transiently expressed in HEK293 cells. The endotoxin levels of the antibodies, determined by the *limulus amebocyte lysate* (LAL) test, were found to be <0.1 IU/mL. The antibodies used for flow-cytometric analyses were purchased from BD (Sweden). Rituximab (Roche), bortezomib (Janssen-Cilag), lenalidomide (Celgene), melphalan (GlaxoSmithKline), and dexamethasone (Mylan) were purchased from local pharmacies (Lund, Sweden or Dijon, France). ARH-77, RPMI-8226, and Daudi cell lines were obtained from the American Type Culture Collection (ATCC, Sweden). NCI-H929, EJM, and OPM-2 cell lines were obtained from the Deutsche Sammlung von Mikroorganismen and Zellkulturen (DSMZ, Germany). All cells were maintained in culture media as recommended by the supplier. Logarithmic growth of cells was ensured before harvesting of cells for xenografting. Female SCID mice on C.B-17 background were obtained from Taconic, Denmark, and were used in the studies at age 7-8 weeks. All animal studies were conducted in accordance with guidelines of the Lund University Hospital, Sweden or University of Utah, Salt Lake City, USA following approval from the local ethical committee for animal care and use.

Isolation of Tumor PCD-Inducing Antibodies Specific for Tumor B Cell-Associated Receptors Antibodies specific for tumor B cell-associated receptors were isolated by subjecting the in vitro CDR shuffled human antibody library n-CoDeR® to differential biopanning of tumor B cells versus T cells, as previously described (Fransson et al., 2006). Briefly, 2×10$^{13}$ n-CoDeR® phage-abs were incubated for 4 hr at 4° C. with Ramos B lymphoma cells and excess plasma membrane vesicles derived from Jurkat T cells. Phage-abs binding to tumor B cells (differentially expressed surface receptors) were separated from membrane vesicles (and antibodies bound to these targeting commonly expressed tumor B:T cell surface receptors) and from unbound phage-abs by loading of the mixture on top of a Ficoll density cushion and pelleting of tumor B cells by centrifugation at 400 g for 10 min. The tumor B cell-bound phage-abs were eluted following resuspension and incubation in 76 mM citric acid buffer (pH 2.5) for 5 min. Following conversion of phage-abs to scFv format, individual antibody clones were expressed and purified from *E.*

*coli* supernatants and screened for binding to tumor B cells (Ramos) or T cells in an FMAT instrument (Applied Biosystems, Foster City, Calif.). Individual antibody clones were evaluated and compared with the anti-CD20 mAb rituximab for tumor PCD-inducing efficacy and potency in CD20-expressing tumor B cell lines (Ramos and Raji) using a high-throughput annexin V/propidium iodide-based flow-cytometry assay, as previously described (Fransson et al., 2006).

Mouse Xenograft Studies

Subcutaneous Grafting

Mice were anaesthetized with a mixture of sevofluran and oxygen prior to myeloma cell inoculation and $1\text{-}10 \times 10^6$ myeloma cells were then subcutaneously injected in a volume of 100 μl into the left flank. Treatment with antibodies by intraperitoneal injection started either 1 day after cell inoculation (prophylactic model) or when tumors reached approximately 100 mm³ (established model). Antibodies were administered in 200 μL of PBS. Treatment with PBS only or isotype IgG were used as controls. Macrophages or NK-cells were depleted by i.p. administration of 0.1 ml clodronate liposomes (Clophosome-A, FormuMax, Scientific Inc. Palo Alto, USA) or 20 μl anti-asialo GM1 pCI Ab (CL8955, Cedarlane Laboratories Limited, Canada) respectively, starting one day prior to antibody treatment, followed by administration twice weekly for a total of three weeks, PBS was used as control. Macrophage and NK cell depletion was assessed upon termination of tumor bearing mice exposed to effector cell depleting agents (see above), spleens were removed and splenocytes isolated by mincing through a cell strainer (70 μm nylon mesh, BD Falcon 352350), erythrocytes were removed by lysis according to manufacturer (BD Pharm Lyse 555899, BD Biosciences). Splenocytes were analysed by flow cytometry using antibodies directed against F4/80 (PE anti-mouse F4/80, clone BM8, BioLegend) and CD11b-APC (APC anti-mouse CD11b, clone M1/70, BD Pharmingen) to detect macrophages (F4/$80^{hi}$ CD11b$^{lo/int}$), and CD49b (PE anti-mouse CD49b, clone DX5, BD Pharmingen) and CD45 (FITC anti-mouse CD45, clone 30-F11, BD Pharmingen) for NK-cells (CD49b$^{hi}$ CD45$^{hi}$), in combination with respective isotype control (PE rat IgG$_2$, (for F4/80); APC IgG$_{2b}$ (for CD11b); PE rat IgM (for CD49b), FITC rat IgG$_{2b}$ (for CD45). 50 000 cells were collected on a FACSCalibur (BD Biosciences).

Tumor size was measured using a digital calliper and tumor volumes were calculated according to the formula width²×length×0.52, as previously described (Cao et al., 1999). Animals were killed by cervical dislocation when tumor cross-sectional radii reached the ethical limit of 1.5 cm or when general health status was significantly affected. Surviving mice were killed after a maximum of 5 months. Blood samples collected from the vena cava were centrifuged at 2500 g for 15 min to obtain serum and the samples were stored at −20° C. Tumors were removed for immunohistochemistry, snap frozen, and kept at −85° C. Cryosections were cut 8 μm thick. Immunohistochemistry was performed with rabbit anti-ICAM-1 (Atlas Antibodies, Stockholm, Sweden) and rabbit anti-human CD20 (Acris Antibodies, Herford, Germany) using a TSA kit (Perkin Elmer, Waltham).

Statistical analyses of tumor growth inhibition relative to control antibody treatment were carried out using Kruskal-Wallis nonparametric ANOVA with Dunn's multiple comparisons test or Mann-Whitney non-parametric analysis, as indicated in the figure legends. Statistical analyses of antibody-mediated mouse survival were carried out using the log-rank test and Graphpad Prism software. *p<0.05, p<0.01, *p<0.001.

Disseminated Models of Multiple Myeloma

The advanced disseminated models of multiple myeloma were performed at Oncodesign, Dijon, France. Briefly, $10 \times 10^6$ RPMI-8226 tumor cells were injected intravenously (i.v.) into the caudal vein of female SCID mice (D0). Tumor cell injections were performed 24-48 hr after whole-body irradiation of mice (1.8 Gy, $^{60}$Co, INRA, Bretennieres). The treatment was started at D5 (RPMI-8226 model), except melphalan, which was administrated at D10. BI-505 or control mAb was administered i.v. at 2 mg/kg twice weekly for 8 weeks; bortezomib at 1 mg/kg/inj i.v. once weekly for 8 weeks; lenalidomide orally at 2 mg/kg/inj for 2 cycles consisting of 5 days of treatment and 2 days of wash out; melphalan i.v. at 3 mg/kg/inj once weekly for 8 weeks; and dexamethasone at 6 mg/kg/inj i.v. thrice weekly for 2 weeks.

Disseminated NK-Cell Deficient RPMI-8226 and U266 Models

Six-eight weeks-old female NOD/Shi-scid IL-2Rγ$^{−/−}$ mice were obtained from Taconic, Denmark. Five million ($5 \times 10^6$) RPMI-8226 or U266 tumor cells in 200 μL of RPMI 1640 were intravenously injected into the caudal vein (day 0). The tumor cell injection was performed 2 hr after whole body irradiation of mice (1.5 Gy, Cesium 137, IBL 637). At day 4, mice were randomized into 6 groups and treatment was initiated according to the schedule below. Animals were sacrificed when they displayed hind limb paralysis or >15% loss in body weight (relative weight at day 0).

SCID-hu Mouse Model of Multiple Myeloma

Human fetal femurs and tibias, obtained at 17 to 22 gestational weeks, were cut into fragments and implanted subcutaneously in SCID mice (SCID-hu) at age 6 to 8 weeks. Each animal was implanted with one bone fragment. Four weeks after bone implantation, 2 to $14 \times 10^6$ bone marrow cells from each patient (two patients per experiment for a total of four patients in two independent experiments, n=4), containing>20% plasma cells were injected directly into the human bone of 6 to 8 SCID-hu mice in a final volume of 30 to 40 μl of phosphate-buffered saline (PBS). One group of mice was implanted with bone only and served as "healthy" bone control. Mouse sera were serially monitored for human immunoglobulin (hIg) and the isotype levels were used as an indicator of myeloma cell growth by elisa. When hIg level reached 10 μg/mL or higher in 2 consecutive measurements after 4 weeks of injection of the tumor cells, the mice were divided into four groups to yield similar mean hIgG levels between groups, each group comprising mice grafted with MM cells from the different patient donors used in each experiment. The four treatment groups were: healthy control group (no myeloma cells injected and no drug treatment), isotype control group (myeloma cells injected and treated with isotype control IgG, 2 mg/kg, i.p., twice weekly), BI505 group (myeloma cells injected and treated with BI505, 2 mg/kg, i.p., twice weekly) and bortezomib group (myeloma cells injected and treated with 1 mg/kg, i.p., twice weekly). In some graphs hIgG levels were normalized to pretreatment (4 weeks) levels and the percent increase or decrease in hIgG levels as a function of treatment and time was analyzed. Normalized data from animals receiving the same treatment (control IgG, BI-505 or bortezomib) but grafted with MM cells from each of the four different patient donors in the two experiments were pooled and statistical difference was assessed by grouped 2-way ANOVA test and Bonferroni's posttest using GraphPad Prism 5 software. Patient myeloma cells were taken after informed consent and with the approval of the local ethics committee. For x-radiography evaluation and quantification of bone mineral density (BMD) mice in the four groups were sacrificed and the implanted human bones were taken out and fixed in 10% formalin solution. Radiographs were taken with an AXR Minishot-100 beryllium source instrument (Associated X-Ray Imaging Corp., Haverhill, Mass., USA) and 100 s exposure at 30 kV. Statistical significance was assessed by unpaired t test using GraphPadInstat 3 software. Implanted human bones from 4 groups were fixed in 10% phosphate-buffered formalin for 24 hr, decalcified with 14% (wt/vol) EDTA (ethylenediaminetetraacetic acid, pH 7.0) for 1-2 weeks, and embedded in paraffin for sectioning for TRAP staining. TRAP staining was performed on healthy and MM-cell injected bones harvested from SCID-hu mice treated as described above. The purple-red-stained cells indicate osteoclasts.

Receptor Occupancy Studies and the Relationship Between Receptor Occupancy and In Vitro and In Vivo Anti-Tumor Activity Mice were anaesthetized with a mixture of isofluran or sevofluran and oxygen prior to myeloma cell inoculation and $1\text{-}2\times10^6$ ARH-77 cells were then subcutaneously injected in a volume of 100 µl into the left flank. Mice received twice-weekly i.p. injections with BI-505 at 20, 2, 0.2, 0.02, or 0.002 mg/kg starting one day after tumor cell inoculation. Treatment with PBS or isotype control was used as control. There were eight to ten mice per dosage/treatment group. Tumor volumes were measured with a digital calliper and were calculated according to formula: $width^2 \times length \times 0.52$ as previously reported (Cao et al., 1999). Sera were prepared from blood samples collected from the vena saphena from 3 animals in each group at different time-points during the course of in vivo experimentation. Briefly, ELISA plates were coated over night with human ICAM-1 protein. The following day, plates were incubated with the serum samples. Biotinylated goat-anti-BI-505 was used for detection of BI-505 in the serum samples. Sera were analysed by ELISA to determine BI-505 trough levels. Trough BI-505 serum concentrations were then plotted as a function of dose and were fitted using five parameter log-log curve and XLfit software (IDBS, Guildford, United Kingdom).

BI-505 receptor occupancy was studied following FACS analyses of tumor cells incubated with increasing concentrations of BI-505 in vitro. Briefly, following pre-blocking of tumor cell FcγR with 1 mg/ml human IgG on ice for 15 min, tumor cells were incubated with 10-fold serially diluted (10 µg/ml to 0.00001 µg/ml) AF647-BI505 and surface bound BI-505 was recorded as the mean fluorescence intensities (MFI) picked up in the FL4 channel of a FACSCalibur instrument. The experiment was repeated three times and mean MFI values were calculated and plotted as a function of antibody concentration. A binding saturation curve was generated by plotting mean MFI values as a function of BI-505 concentration. The curve was fitted using a five-parameter log-log curve and XLfit software. BI-505 concentration dependent PCD was calculated by plotting the percentage of maximal tumor PCD in vitro as a function of BI-505 concentration in a manner analogous to that described for BI-505 receptor occupancy. Briefly, tumor cells were cultured with increasing concentrations of BI-505 in the presence of hyper-cross-linking antibody reagent for 24 hr, and PCD was monitored after combined staining with Annexin V/AF488 and propidium iodide using flow cytometry. Cells received treatment in triplicate and the experiment was repeated three to five times. Mean percentage of maximal PCD was then plotted as a function of BI-505 concentration and was fitted using a five parameter log-log curve and XLfit software. In vitro PCD and in vivo anti-tumor activity were plotted as a function of receptor occupancy using curve fitting equations and data generated and described above.

Analysis of Multiple Myeloma Patients' Plasma Cell Surface ICAM-1 Expression

Bone marrow aspirates from 29 patients diagnosed with MM or related diseases (plasmocytoma, plasma cell leukemia, or amyloid light chain amyloidosis) at the Department of Hematology, Skånes University Hospital, Lund were analyzed by flow cytometry using 4 cocktails of antibodies, each suitable for recognizing plasma cells (Figure S3) after informed consent and with the approval of the local ethical committee. Clinical data were obtained from patients' charts.

BI-505 Isotype Variant Binding to FcγRs

His-tagged human FcγRIIIa and mouse FcγRIV were transiently expressed in HEK293E cells, purified using Ni-NTA chromatography, and characterized by SDS-PAGE and/or Biacore. Surface plasmon resonance (SPR) measurements were performed using a Biacore 3000 instrument. Goat F(ab)'2 α-human-F(ab)'2 fragments (Jackson Laboratories) were immobilized with a CM-5 chip using a standard amine coupling protocol. BI-505 ($IgG_1$) and $IgG_4$ or $IgG_{1\ N297Q}$ variants of BI-505 were diluted to 15 and 60 µg/mL respectively and added to the surface at 10 µL/min for 3 min. His-tagged human FcγRIIIa or mouse FcγRIV was pre-incubated with an α-HIS antibody (R&D Systems) at a 2:1 molar ratio before addition to the chip surface, 30 µL/min, for 1 min. After each cycle the surface was regenerated twice with glycine buffer pH 1.7.

ADCP

Buffy coats from healthy human donors were ordered through the local blood central at Lund University Hospital and Halmstad Hospital. Peripheral blood mononuclear cells (PBMCs) were first extracted using Ficoll-Paque PLUS (GE Healthcare Life Sciences), followed by isolation of monocytes with CD14 MicroBeads and MACS separation (Miltenyi Biotec). The monocytes were cultured in RPMI 1640 medium with 10% heat-inactivated FBS (Invitrogen) and 25 ng/mL of recombinant human M-CSF (R&D Systems) for 6-14 days, causing differentiation into macrophages. Medium with M-CSF was changed every 2-3 days upon initiation of cultures.

RPMI-8226 cells (ATCC) were continuously cultured in RPMI 1640 medium supplemented with 10 mM HEPES, 1 mM sodium pyruvate and 10% FBS. For multiple myeloma cells, freshly isolated bone marrow samples were donated by patients at Lund University Hospital and subsequently processed with Ficoll-Paque PLUS. Negative isolation of malignant plasma cells was then performed using the Plasma Cell Isolation Kit II according to the manufacturer's instructions (Miltenyi Biotec).

At least 4 h before co-culture with target cells the cultured macrophages were detached with Accutase (Sigma Aldrich), before plated in flat 96-well plates at 50 000 cells/well and placed in 37° C. Target cells were counted and stained with 5 µM CFSE (Molecular Probes) at 37° C., before incubation with $IgG_1$ antibodies (BI-505, BI-505$_{N297Q}$, anti-FITC negative control and Rituximab, respectively) for up to 1 hr on ice. After washing, the different cell solutions were added to the culture plates containing macrophages at a ratio of 5:1 (Target cells:Macrophages). Thereafter, the culture plates were incubated at 37° C. for 1-2 hr (primary patient MM cells) or 16 hr (RPMI-8226 cells). Next, samples were stained with APC-conjugated anti-CD206 antibody (BD Biosciences), before harvested by scraping the culture plate wells. The resulting cell solutions were then analyzed by flow cytometry, where CD206+ macrophages were gated and acquired at 5000 cells/sample. A cut-off level identifying CFSE+, CD206+ double positive (phagocytic) macrophages was set for each experimental sample series. This level differed between the individual assays since the magnitude of basic (unstimulated) phagocytosis varied (different donors and time-points) among the experiments.

ADCC

Buffy coats from human donors (ordered through Blodcentralen, Lund) were used to isolate peripheral blood mononuclear cells (PBMCs), and subsequently natural killer (NK) cells. Briefly, peripheral blood components were separated using Ficoll-Paque PLUS (Amersham Biosciences, Sweden) in Leucosep tubes (Greiner Bio-One). The PBMC fraction was removed and thoroughly washed in ice-cold D-PBS (Invitrogen) before magnetic labelling and separation of the NK cell population using positive or negative NK cell-isolation kits and MACS LS columns (Miltenyi Biotec). The purity of the obtained NK cell fractions was >75% as determined by flow cytometry after staining with $\alpha$-CD56 antibodies (BD Biosciences). Target cells were harvested and then incubated in medium with or without the respective antibodies (2 µg/mL) for 60 min on ice. B and T cells were isolated from PBMC fractions with magnetic labelling and separation of the B or T cell population using positive cell isolation kits and MACS LS columns (Miltenyi Biotec, Germany). Cells were then washed and resuspended in cold medium before dispension into FACS tubes. The isolated NK cells were subsequently diluted in ADCC medium and dispensed together with the respective antibody-coated target cells at varying effector/target cell ratios (40:1, 20:1, 5:1, and 1:1). All experiments were performed in triplicate. After incubation, TO-PRO-3 dye and counting beads (Invitrogen) were added and cells were analyzed for membrane permeabilization using flow cytometry.

CDC

Target cells were harvested as described above (under ADCC heading) and incubated with antibodies at 5 µg/mL for 60 min on ice and then washed. Human serum, normal or heat-inactivated (Sigma, Sweden), was added to tubes and the samples were incubated for 2 hr at 37° C. After completion of incubation, ToPo-Pro-3 (Invitrogen) was added at a final concentration of 0.3 µM and cells were analyzed for membrane permeabilization using flow cytometry.

HUVEC and HMVEC Cell Culture and Monitoring of Apoptosis Assay

HUVEC (Cascade Biologics, pool of donors) and HMVEC (Cascade Biologics) were plated in 6-well plates (80 000-120 000 cells/well) in the presence or absence of 200 U/mL IFN$\gamma$, in order to induce ICAM-1 expression. Media was changed the day before apoptosis-induction experiments were performed and titrated concentrations of BI-505, enlimomab or isotype control antibody were added to the cells, in the presence or absence of cross-linking Fab (ab')$_2$ (same as the B-cell protocol). Cells were then cultured for more than 16 hr at 37° C. in a humidified atmosphere of 5% $CO_2$. The cells were harvested and stained for necrotic cells with the nuclei stain SYTOX red, and for apoptotic cells using Annexin V-488. Necrotic cells were identified by increased fluorescence in the FL-4 channel and apoptotic cells by increased signal in the FL-1 channel on a flow cytometer (FACSCalibur, BD Bioscience).

T Cell Proliferation

T cells used in the proliferation assay were stained with CFSE (carboxyfluorescein diacetate, succinimidyl ester; Invitrogen). The CFSE-labeled cells were seeded at a density of 150,000 cells/well in wet and air-dried antibody-coated plates. The cells were cultured for 6 days with one renewal of medium after 3 days. AccuCheck Count Beads (Invitrogen) were used to ensure accurate quantification of cell proliferation in the flow cytometry. Cells received treatments in triplicate. Figures show pooled data using cells from four different donors (n=4).

Measurement of Cytokine Release

For cell culture cytokine quantifications, cells were seeded in 96-well cell culture wet and air-dried coated plates at a density of $1 \times 10^6$ cells/mL and cultured with antibodies for 24 hr. At the end of cell culture, supernatants were removed from individual wells and were aliquoted in duplicate microtiter plates and stored at −80° C. for subsequent cytokine analysis. Cytokine release from PBMC was quantified from cell culture supernatants using a commercially available ELISA kit (Human ProInflammatory 9-plex, Meso Scale Discovery, Md., USA) according to the manufacturer's instructions. Cells received treatment in triplicate. Figures show pooled data from four different donors (n=4).

In experiments assessing anti-ICAM-1 effects on pre-activated PBMC, cells were pre-incubated with LPS at concentrations that induced sub maximal pro-inflammatory cytokine release. Based on obtained results PBMC were then stimulated with two different concentrations of LPS, 10 and 100 µg/mL, which induced sub maximal cytokine release for the different monitored cytokines. Cells were incubated in a humidified atmosphere of 5% $CO_2$ at 37° C. with LPS for 6 hr before addition of antibody. The cells were incubated for a further 16 hr before supernatants were harvested as previously described. Cells received treatment in triplicate. Figures show pooled data from four different donors (n=4).

BI-505 Cross-Reactivity to ICAM-1 of Animal Species Commonly Used for Toxicological Studies The cross reactivity of BI-505 to mouse, rat, rabbit, and cynomolgus monkey ICAM-1 was investigated using several methods (i.e. immunohistochemistry, flow cytometry, and enzyme-linked immunosorbent assay [ELISA]) and sources of target protein (tissue, ICAM-1 transfected cells, endogenous ICAM-1 expressing cells, and recombinant ICAM-1 protein). Polyclonal anti-mouse ICAM-1, anti-rat ICAM-1, anti-rabbit ICAM-1, and anti-cynomolgus ICAM-1 antibodies were used as positive controls in experiments. Isotype control human IgG$_1$ was used as negative control for BI-505 and species matched polyclonal IgG lacking specificity for ICAM-1 served as negative controls for ICAM-1 specific polyclonal antibodies.

Single Dose Study in the Rat

Rats (n=6 per sex and treatment, for a total of 36 rats) were given 0.5, 2.5 or 10 mg/kg BI-505 as a single i.v. treatment. Blood was drawn from the caudal vein of rats at the following time-points: pre-dose, 15 min, 30 min, 1 hr, 2 hr, 8 hr, 24 hr, 2 days, 3 days, 5 days, 8 days, 2 weeks and 3 weeks. BI-505 serum concentrations were determined by ELISA from 15-18 samples per time-point, collected from alternating animals. Pharmacokinetics was calculated from the individual animal serum concentration-time data of BI-505 using non-compartmental analyses.

Animals were observed for adverse reactions post-dosing on Day 1 upon return to the home cage and at 0.5, 1, 2 and 4 hr post dose, and detailed physical examinations were performed weekly for the full duration of the study (6 weeks). Body weight and food intake was recorded once weekly. Blood samples for anti-BI-505 antibodies were withdrawn on day 22 and at the end of the observation period (no anti-BI-505 antibodies were detected).

REFERENCES

Aalinkeel, R., Nair, M. P. N., Sufrin, G., Mahajan, S. D., Chadha, K. C., Chawda, R. P., and Schwartz, S. A. (2004), "Gene Expression of Angiogenic Factors Correlates with Metastatic Potential of Prostate Cancer Cells," *Cancer Res.*, 64:5311-5321.

Alduaij, W., and Illidge, T. M. (2011), "The future of anti-CD20 monoclonal antibodies: are we making progress?" *Blood* 117:2993-3001.

Beck, A., Wurch, T., Bailly, C., and Corvaia, N. (2010) "Strategies and challenges for the next generation of therapeutic antibodies," *Nat. Rev. Immunol.*, 10:345-352.

Beers, S. A., Chan, C. H., James, S., French, R. R., Attfield, K. E., Brennan, C. M., Ahuja, A., Shlomchik, M. J., Cragg, M. S., and Glennie, M. J. (2008), "Type II (tositumomab) anti-CD20 monoclonal antibody out performs type I (rituximab-like) reagents in B-cell depletion regardless of complement activation," *Blood* 112:4170-4177.

Bibeau, F., Lopez-Crapez, E., Di Fiore, F., Thezenas, S., Ychou, M., Blanchard, F., Lamy, A., Penault-Llorca, F., Frebourg, T., Michel, P., et al. (2009), "Impact of Fc{gamma}RIIa-Fc{gamma}RIIIa polymorphisms and KRAS mutations on the clinical outcome of patients with metastatic colorectal cancer treated with cetuximab plus irinotecan," *J. Clin. Oncol.*, 27:1122-1129.

Cao, R., Wu, H. L., Veitonmaki, N., Linden, P., Farnebo, J., Shi, G. Y., and Cao, Y. (1999), "Suppression of angiogenesis and tumor growth by the inhibitor K1-5 generated by plasmin-mediated proteolysis," *Proc. Natl. Acad. Sci. USA*, 96:5728-5733.

Cheson, B. D., and Leonard, J. P. (2008), "Monoclonal antibody therapy for B-cell non-Hodgkin's lymphoma," *N. Engl. J. Med.*, 359:613-626.

Clynes, R. A., Towers, T. L., Presta, L. G., and Ravetch, J. V. (2000), "Inhibitory Fc receptors modulate in vivo cytoxicity against tumor targets," *Nat. Med.*, 6:443-446.

Cragg, M. S., and Glennie, M. J. (2004), "Antibody specificity controls in vivo effector mechanisms of anti-CD20 reagents," *Blood*, 103:2738-2743.

Cragg, M. S., Morgan, S. M., Chan, H. T., Morgan, B. P., Filatov, A. V., Johnson, P. W., French, R. R., and Glennie, M. J. (2003), "Complement-mediated lysis by anti-CD20 mAb correlates with segregation into lipid rafts," *Blood*, 101:1045-1052.

Fransson, J., Tornberg, U. C., Borrebaeck, C. A., Carlsson, R., and Frendeus, B. (2006), "Rapid induction of apoptosis in B-cell lymphoma by functionally isolated human antibodies," *Int. J. Cancer*, 119:349-358.

Gan, H. K., Lappas, M., Cao, D. X., Cvrljevdic, A., Scott, A. M., and Johns, T. G. (2009) "Targeting a unique EGFR epitope with monoclonal antibody 806 activates NF-kappaB and initiates tumour vascular normalization," *J. Cell Mol. Med.*, 13, 3993-4001.

Hideshima, T., Mitsiades, C., Tonon, G., Richardson, P. G., and Anderson, K. C. (2007) "Understanding multiple myeloma pathogenesis in the bone marrow to identify new therapeutic targets," *Nat. Rev. Cancer*, 7:585-598.

Huang, Y. W., Richardson, J. A., and Vitetta, E. S. (1995), "Anti-CD54 (ICAM-1) has antitumor activity in SCID mice with human myeloma cells," *Cancer Res.*, 55:610-616.

Ivanov, A., Beers, S. A., Walshe, C. A., Honeychurch, J., Alduaij, W., Cox, K. L., Potter, K. N., Murray, S., Chan, C. H., Klymenko, T., et al. (2009), "Monoclonal antibodies directed to CD20 and HLA-DR can elicit homotypic adhesion followed by lysosome-mediated cell death in human lymphoma and leukemia cells," *J. Clin. Invest.*, 119:2143-2159.

Johnson, J. P., Stade, B. G., Hupke, U., Holzmann, B., and Riethmuller, G. (1988), "The melanoma progression-associated antigen P3.58 is identical to the intercellular adhesion molecule, ICAM-1," *Immunobiology*, 178:275-284.

Kapoor, P., Greipp, P. T., Morice, W. G., Rajkumar, S. V., Witzig, T. E., and Greipp, P. R. (2008), "Anti-CD20 monoclonal antibody therapy in multiple myeloma," *Br. J. Haematol.*, 141:135-148.

Kavanaugh, A. F., Schulze-Koops, H., Davis, L. S., and Lipsky, P. E. (1997), "Repeat treatment of rheumatoid arthritis patients with a murine anti-intercellular adhesion molecule 1 monoclonal antibody," *Arthritis Rheum.*, 40:849-853.

Kyle, R. A., and Rajkumar, S. V. (2004), "Multiple myeloma," *N. Engl. J. Med.*, 351:1860-1873.

Lejeune, J., Thibault, G., Ternant, D., Cartron, G., Watier, H., and Ohresser, M. (2008), "Evidence for linkage disequilibrium between Fcgamma RIIIa-V158F and Fcgamma RIIa-H131R polymorphisms in white patients, and for an Fcgamma RIIIa-restricted influence on the response to therapeutic antibodies," *J. Clin. Oncol.*, 26:5489-5491; author reply 5491-5482.

Lim, S. H., Beers, S. A., French, R. R., Johnson, P. W., Glennie, M. J., and Cragg, M. S. (2010), "Anti-CD20 monoclonal antibodies: historical and future perspectives," *Haematologica*, 95:135-143.

Manches, O., Lui, G., Chaperot, L., Gressin, R., Molens, J. P., Jacob, M. C., Sotto, J. J., Leroux, D., Bensa, J. C., and Plumas, J. (2003), "In vitro mechanisms of action of rituximab on primary non-Hodgkin lymphomas," *Blood*, 101:949-954.

Mileski, W. J., Burkhart, D., Hunt, J. L., Kagan, R. J., Saffle, J. R., Herndon, D. N., Heimbach, D. M., Luterman, A., Yurt, R. W., Goodwin, C. W., and Hansborough, J. (2003), "Clinical effects of inhibiting leukocyte adhesion with monoclonal antibody to intercellular adhesion molecule-1 (enlimomab) in the treatment of partial-thickness burn injury," *J. Trauma*, 54:950-958.

Mitsiades, C. S., Mitsiades, N. S., Bronson, R. T., Chauhan, D., Munshi, N., Treon, S. P., Maxwell, C. A., Pilarski, L., Hideshima, T., Hoffman, R. M., and Anderson, K. C. (2003), "Fluorescence imaging of multiple myeloma cells in a clinically relevant SCID/NOD in vivo model: biologic and clinical implications," *Cancer Res.*, 63:6689-6696.

Musolino, A., Naldi, N., Bortesi, B., Pezzuolo, D., Capelletti, M., Missale, G., Laccabue, D., Zerbini, A., Camisa, R., Bisagni, G., et al. (2008), "Immunoglobulin G fragment C receptor polymorphisms and clinical efficacy of trastuzumab-based therapy in patients with HER-2/neu-positive metastatic breast cancer," *J. Clin. Oncol.*, 26:1789-1796.

Nimmerjahn, F., Bruhns, P., Horiuchi, K., and Ravetch, J. V. (2005), "FcgammaRIV: a novel FcR with distinct IgG subclass specificity," *Immunity*, 23:41-51.

Park, S., Jiang, Z., Mortenson, E. D., Deng, L., Radkevich-Brown, O., Yang, X., Sattar, H., Wang, Y., Brown, N. K., Greene, M., et al. (2010), "The therapeutic effect of anti-HER2/neu antibody depends on both innate and adaptive immunity," *Cancer Cell*, 18:160-170.

Rawstron, A. C., Orfao, A., Beksac, M., Bezdickova, L., Brooimans, R. A., Bumbea, H., Dalva, K., Fuhler, G., Gratama, J., Hose, D., et al. (2008), "Report of the European Myeloma Network on multiparametric flow cytometry in multiple myeloma and related disorders," *Haematologica* 93:431-438.

Richardson, P. G., Lonial, S., Jakubowiak, A. J., Harousseau, J. L., and Anderson, K. C. (2011), "Monoclonal antibodies in the treatment of multiple myeloma," *Br. J. Haematol.* 2011 Jul. 21. doi: 10.1111/j.1365-2141.2011.08790.x. [Epub ahead of print].

Sampaio, M. S., Vettore, A. L., Yamamoto, M., Chauffulle Mde, L., Zago, M. A., and Colleoni, G. W. (2009) "Expression of eight genes of nuclear factor-kappa B pathway in multiple myeloma using bone marrow aspirates obtained at diagnosis," *Histol. Histopathol.*, 24:991-997.

Schmidmaier, R., Baumann, P., Simsek, M., Dayyani, F., Emmerich, B., and Meinhardt, G. (2004), "The HMG-CoA reductase inhibitor simvastatin overcomes cell adhesion-mediated drug resistance in multiple myeloma by geranylgeranylation of Rho protein and activation of Rho kinase," *Blood*, 104:1825-1832.

Schmidmaier, R., Morsdorf, K., Baumann, P., Emmerich, B., and Meinhardt, G. (2006), "Evidence for cell adhesion-mediated drug resistance of multiple myeloma cells in vivo," *Int. J. Biol. Markers*, 21: 218-222.

Schneider, D., Berrouschot, J., Brandt, T., Hacke, W., Ferbert, A., Norris, S. H., Polmar, S. H., and Schafer, E. (1998), "Safety, pharmacokinetics and biological activity of enlimomab (anti-ICAM-1 antibody): an open-label, dose escalation study in patients hospitalized for acute stroke," *Eur. Neurol.*, 40, 78-83.

Smith, M. R. (2003), "Rituximab (monoclonal anti-CD20 antibody): mechanisms of action and resistance," *Oncogene*, 22:7359-7368.

Soderlind, E., Strandberg, L., Jirholt, P., Kobayashi, N., Alexeiva, V., Aberg, A. M., Nilsson, A., Jansson, B., Ohlin, M., Wingren, C., et al. (2000), "Recombining germline-derived CDR sequences for creating diverse single-framework antibody libraries," *Nat. Biotechnol.*, 18:852-856.

Stebbings, R., Findlay, L., Edwards, C., Eastwood, D., Bird, C., North, D., Mistry, Y., Dilger, P., Liefooghe, E., Cludts, I., et al. (2007), "'Cytokine storm' in the phase I trial of monoclonal antibody TGN1412: better understanding the causes to improve preclinical testing of immunotherapeutics," *J. Immunol.*, 179:3325-3331.

van der Kolk, L. E., Grillo-Lopez, A. J., Baars, J. W., Hack, C. E., and van Oers, M. H. (2001), "Complement activation plays a key role in the side-effects of rituximab treatment," *Br. J. Haematol.*, 115:807-811.

Weiner, L. M., Surana, R., and Wang, S. (2010), "Monoclonal antibodies: versatile platforms for cancer immunotherapy," *Nat. Rev. Immunol.*, 10:317-327.

Weng, W. K., and Levy, R. (2003), "Two immunoglobulin G fragment C receptor polymorphisms independently predict response to rituximab in patients with follicular lymphoma," *J. Clin. Oncol.*, 21:3940-3947.

Wilson, N. S., Yang, B., Yang, A., Loeser, S., Marsters, S., Lawrence, D., Li, Y., Pitti, R., Totpal, K., Yee, S., et al. (2011), "An Fcgamma receptor-dependent mechanism drives antibody-mediated target-receptor signaling in cancer cells," *Cancer Cell*, 19:101-113.

Yaccoby, S., Barlogie, B., and Epstein, J. (1998), "Primary myeloma cells growing in SCID-hu mice: a model for studying the biology and treatment of myeloma and its manifestations," *Blood* 92:2908-2913.

Zhang, W., Gordon, M., Schultheis, A. M., Yang, D. Y., Nagashima, F., Azuma, M., Chang, H. M., Borucka, E., Lurje, G., Sherrod, A. E., et al. (2007), "FCGR2A and FCGR3A polymorphisms associated with clinical outcome of epidermal growth factor receptor expressing metastatic colorectal cancer patients treated with single-agent cetuximab," *J. Clin. Oncol.*, 25:3712-3718.

Zheng, Y., Cai, Z., Wang, S., Zhang, X., Qian, J., Hong, S., Li, H., Wang, M., Yang, J., and Yi, Q. (2009), "Macrophages are an abundant component of myeloma microenvironment and protect myeloma cells from chemotherapy drug-induced apoptosis," *Blood*, 114:3625-3628.

Zheng, Y., Yang, J., Qian, J., Qiu, P., Hanabuchi, S., Lu, Y., Wang, Z., Liu, Z., Li, H., He, J., et al. (2013), "PSGL-1/selectin and ICAM-1/CD18 interactions are involved in macrophage-induced drug resistance in myeloma," *Leukemia*, 27(3):702-710.

Embodiments of the invention will now be described in the following numbered paragraphs:

1. A method of inducing apoptosis in a target cell comprising the steps:
   a. providing one or more target cells displaying the cell surface antigen, ICAM-1;
   b. providing one or more binding molecules which selectively binds to cell surface ICAM-1 and, on binding ICAM-1, induces apoptosis of the target cell;
   c. exposing the target cells of (a) to the binding molecules of (b) to induce apoptosis in the target cells.

2. A method as provided in paragraph 1 wherein the binding molecules are antibody molecules.

3. A method of inducing apoptosis in a target cell comprising the steps:
   a. providing one or more target cells displaying the cell surface antigen, HLA-DR/DP and/or surface IgM;
   b. providing one or more antibody molecules which selectively binds to cell surface HLA-DR/DP and/or surface IgM and, on binding HLA-DR/DP and/or surface IgM, inducing apoptosis of the target cell;
   c. exposing the target cells of (a) to the antibody molecules of (b) to induce apoptosis in the target cells.

4. A binding molecule for use in the method of paragraphs 1 or 2 which selectively binds to cell surface ICAM-1 and, on binding ICAM-1, induces apoptosis of the target cell.

5. An antibody molecule for use in the method of paragraph 3 which selectively binds to a cell surface antigen of a target cell and, on binding the cell surface antigen, induces apoptosis of the target cell and wherein the cell surface antigen is HLA-DR/DP and/or surface IgM.

6. A binding molecule as described in paragraph 4 wherein the binding molecule is an antibody molecule.

7. A binding molecule as described in either paragraph 4 or 6 wherein the cell surface antigen is ICAM-1.

8. An antibody molecule as described in paragraph 5 wherein the cell surface antigen is HLA-DR/DP.

9. An antibody molecule as described in paragraph 5 wherein the cell surface antigen is surface IgM.

10. A binding molecule or antibody molecule as described in any one of paragraphs 4 to 9 wherein the target cell is an immune cell or an epithelial cell.

11. A binding molecule or antibody molecule as described in paragraph 10 wherein the immune cell is a B lymphocyte.

12. A binding molecule or antibody molecule as described in any one of paragraphs 4 to 11 wherein the target cell is associated with a disease.

13. A binding molecule or antibody molecule as described in paragraph 12 wherein the disease is selected from the group consisting of: cancer; autoimmune diseases including but not restricted to rheumatoid arthritis and SLE, acute and chronic inflammatory disorders, sepsis and infectious disease including but not restricted to HIV.

14. A binding molecule or antibody molecule as described in paragraph 13 wherein the disease is a cancer selected from lymphoma (leukaemia, myeloma), gastric cancer, breast cancer, liver cancer, lung cancer, melanoma, bladder cancer, choroid cancer, pancreatic cancer, colon cancer and prostate cancer.

15. The binding molecule or antibody molecule as described in any one of paragraphs 6 to 14 wherein the antibody molecule is an IgG.

16. The binding molecule or antibody molecule as described in paragraph 15 wherein the single chain antibody is selected from the group of an IgG1, IgG2, IgG3 or IgG4.

17. The binding molecule or antibody molecule as described in any one of paragraphs 6 to 16 wherein the antibody molecule is human or humanised.

18. A binding molecule or antibody molecule as described in any one of paragraphs 6 to 17 wherein the antibody has variable regions having the sequences of any one of FIGS. 9 to 11 or functionally equivalent homologues thereof.

19. A binding molecule or antibody molecule as described in paragraph 18 wherein the antibody has variable regions having the sequences of FIG. 9 or functionally equivalent homologues thereof.

20. A binding molecule or antibody molecule as described in paragraph 18 wherein the antibody has variable regions having the sequences of FIG. 10 or functionally equivalent homologues thereof.

21. A binding molecule or antibody molecule as described in paragraph 18 wherein the antibody has variable regions having the sequences of FIG. 11 or functionally equivalent homologues thereof.

22. A nucleic acid having a nucleotide sequence encoding an antibody molecule as described in any one of paragraphs 4 to 21.

23. A nucleic acid as described in paragraph 22 having the nucleotide sequence of any one of FIGS. 9 to 11.

24. Use of the binding molecule or antibody molecule as defined in any one of paragraphs 4 to 21 in the diagnosis and/or treatment and/or prevention of a disease, the diagnosis and/or treatment and/or prevention requiring the destruction of a target cell.

25. Use of the binding molecule or antibody molecule as defined in any one of paragraphs 4 to 21 in the manufacture of a medicament for the treatment and/or prevention of a disease the diagnosis and/or treatment and/or prevention requiring the destruction of a target cell.

26. The use according to either of paragraphs 24 or 25 wherein the disease to be treated is selected from the group consisting of: cancer; autoimmune diseases including but not restricted to rheumatoid arthritis and SLE, acute and chronic inflammatory disorders, sepsis and infectious disease including but not restricted to HIV.

27. The use according to paragraph 26 wherein the disease to be treated is cancer selected from lymphoma (leukaemia, myeloma), gastric cancer, breast cancer, liver cancer, lung cancer, melanoma, bladder cancer, choroid cancer, pancreatic cancer, colon cancer and prostate cancer.

28. The use according to any one of paragraphs 24 to 27 wherein the binding molecule or antibody molecule is as defined in either paragraph 8 or 19 and the disease to be treated is as defined in either of paragraphs 24 or 25.

29. The use according to any one of paragraphs 24 to 27 wherein the binding molecule or antibody molecule is as defined in either paragraph 7 or 20 and the disease to be treated is a lymphoma as defined in paragraph 27.

30. The use according to any one of paragraphs 24 to 27 wherein the binding molecule or antibody molecule is as defined in either paragraph 9 or 21 and the disease to be treated is a lymphoma as defined in paragraph 27.

31. A pharmaceutical composition comprising the binding molecule or antibody molecule as defined in any one of paragraphs 4 to 21 and a pharmaceutically-acceptable carrier, excipient or diluent.

32. An in vitro method of inducing apoptosis in a target cell comprising the steps of:
   a. providing one or more target cells;
   b. providing one or more binding molecules or antibody molecules as defined in any one of paragraphs 4 to 21
   c. exposing the target cells of (a) to the binding molecules or antibody molecules of (b) so as to induce apoptosis in the target cells.

33. An in vitro method as described in paragraph 32 wherein the target cells provided in step (a) are immune cells or epithelial cells.

34. An in vitro method as described in paragraph 33 wherein the immune cells are B-lymphocytes.

35. An in vitro method as described in any one of paragraphs 32 to 34 wherein the target cells are associated with a disease.

36. An in vitro method as described in paragraph 35 wherein the disease is selected from the group consisting of: cancer; autoimmune diseases including but not restricted to rheumatoid arthritis and SLE, acute and chronic inflammatory disorders, sepsis and infectious disease including but not restricted to HIV.

37. An in vitro method as described in paragraph 36 wherein the disease is a cancer selected from lymphoma (leukaemia, myeloma), gastric cancer, breast cancer, liver cancer, lung cancer, melanoma, bladder cancer, choroid cancer, pancreatic cancer, colon cancer and prostate cancer.

38. An in vivo method of inducing apoptosis in a target cell comprising the steps of:
   a. providing one or more target cells;
   b. providing one or more binding molecules or antibody molecules as defined in any of paragraphs 4 to 21
   c. exposing the target cells of (a) to the binding molecules or antibody molecules of (b) so as to induce apoptosis in the target cells.

39. An in vivo method as described in paragraph 38 wherein the target cells provided in step (a) are immune cells or epithelial cells.

40. An in vivo method as described in paragraph 39 wherein the immune cells are B-lymphocytes.

41. An in vivo method as described in any one of paragraphs 38 to 40 wherein the target cells are associated with a disease.

42. An in vivo method as described in paragraph 41 wherein the disease is selected from the group consisting of: cancer; autoimmune diseases including but not restricted to rheumatoid arthritis and SLE, acute and chronic inflammatory disorders, sepsis and infectious disease including but not restricted to HIV.

43. An in vivo method as described in paragraph 42 wherein the disease is a cancer selected from lymphoma (leukaemia, myeloma), gastric cancer, breast cancer, liver cancer, lung cancer, melanoma, bladder cancer, choroid cancer, pancreatic cancer, colon cancer and prostate cancer.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the following claims.

The invention claimed is:

1. An antibody which selectively binds to cell surface ICAM-1 and, on binding ICAM-1, induces Fc-FcγR-dependent cell death of a target cell in vivo, wherein the antibody comprises variable regions having the sequences of SEQ ID NOs: 6 and 8.

2. The antibody of claim 1 wherein the Fc-FcγR-dependent cell death is mediated by macrophages.

3. The antibody of claim 1, wherein the cell death is independent of apoptosis.

4. The antibody of claim 1, wherein the binding molecule additionally induces apoptosis of the target cell.

5. The antibody of claim 1, wherein the target cell is an immune cell or an epithelial cell.

6. The antibody of claim 5 wherein the immune cell is a B lymphocyte.

7. The antibody of claim 1, wherein the target cell is associated with a disease.

8. The antibody of claim 7 wherein the disease is selected from the group consisting of: cancer; autoimmune diseases; rheumatoid arthritis; SLE, acute and chronic inflammatory disorders, sepsis; infectious disease; and HIV.

9. The antibody of claim 8 wherein the disease is a cancer selected from the group consisting of: lymphoma, leukaemia, myeloma, gastric cancer, breast cancer, liver cancer, lung cancer, melanoma, bladder cancer, choroid cancer, pancreatic cancer, colon cancer and prostate cancer.

10. The antibody of claim 1, wherein the antibody is an IgG.

11. The antibody of claim 10 wherein the antibody is a single chain antibody of an antibody selected from the group consisting of: $IgG_1$, $IgG_2$, $IgG_3$ or $IgG_4$.

12. The antibody of claim 1, wherein the antibody is human or humanized.

13. A pharmaceutical composition comprising the antibody of claim 1, and a pharmaceutically acceptable carrier, excipient or diluent.

14. An in vivo method of inducing Fc-FcγR-dependent cell death in a target cell, the method comprising:
 a. providing one or more target cells displaying cell surface antigen ICAM-1;
 b. providing one or more antibodies which selectively binds to cell surface antigen ICAM-1, and, on binding ICAM-1, induces Fc-FcγR-dependent cell death of the target cell;
 c. exposing the target cells to the antibodies to induce Fc-FcγR-dependent cell death of the target cells,
 wherein the antibodies comprise variable regions having the sequences of SEQ ID NOs: 6 and 8.

15. A method of diagnosing, or treating an ICAM-1-associated disease in a subject in need thereof, the method comprising administering to the subject an antibody which selectively binds to cell surface antigen ICAM-1, and, on binding ICAM-1, induces Fc-FcγR-dependent cell death of a target cell, wherein the method requires the destruction of the target cell, and wherein the antibody comprises variable regions having the sequences of SEQ ID NOs: 6 and 8.

* * * * *

```
                        SEQUENCE LISTING

<160> NUMBER OF SEQ ID NOS: 12

<210> SEQ ID NO 1
<211> LENGTH: 351
<212> TYPE: DNA
<213> ORGANISM: Homo sapiens

<400> SEQUENCE: 1
gaggtgcagc tgttggagtc tgggggaggc ttggtacagc ctggggggtc cctgagactc      60
tcctgtgcag cctctggatt cacctttagc agctatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcaaatga acagcctgag agccgaggac actgccgtgt attactgtgc gagagatggg     300
ctactacccc ttgactactg gggccagggt acactggtca ccgtgagctc a              351

<210> SEQ ID NO 2
<211> LENGTH: 117
<212> TYPE: PRT
<213> ORGANISM: Homo sapiens

<400> SEQUENCE: 2

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Leu Leu Pro Leu Asp Tyr Trp Gly Gln Gly Thr Leu
            100                 105                 110

Val Thr Val Ser Ser
        115

<210> SEQ ID NO 3
<211> LENGTH: 336
<212> TYPE: DNA
<213> ORGANISM: Homo sapiens

<400> SEQUENCE: 3
cagtctgtgc tgactcagcc accctcagcg tctgggaccc ccgggcagag ggtcaccatc      60
tcttgttctg gaggcagctc caacatcgga gggaatgctg taaattggta tcagcagctc     120
ccaggaacgg ccccccaaact cctcatctat gaaaataata agcgaccctc aggggtccct     180
gaccgattct ctggctccaa gtctggcacc tcagcctccc tggccatcag tgggctccgg     240
tccgaggatg aggctgatta ttactgcagc tcatatgcgg tcagcaacaa tttcgaggtg     300
ctattcggcg gaggaaccaa gctgacggtc ctaggt                               336
```

-continued

```
<210> SEQ ID NO 4
<211> LENGTH: 112
<212> TYPE: PRT
<213> ORGANISM: Homo sapiens

<400> SEQUENCE: 4
```

Gln Ser Val Leu Thr Gln Pro Pro Ser Ala Ser Gly Thr Pro Gly Gln
 1               5                  10                  15

Arg Val Thr Ile Ser Cys Ser Gly Ser Ser Asn Ile Gly Gly Asn
            20                  25                  30

Ala Val Asn Trp Tyr Gln Gln Leu Pro Gly Thr Ala Pro Lys Leu Leu
        35                  40                  45

Ile Tyr Glu Asn Asn Lys Arg Pro Ser Gly Val Pro Asp Arg Phe Ser
 50                  55                  60

Gly Ser Lys Ser Gly Thr Ser Ala Ser Leu Ala Ile Ser Gly Leu Arg
 65                  70                  75                  80

Ser Glu Asp Glu Ala Asp Tyr Tyr Cys Ser Ser Tyr Ala Val Ser Asn
                85                  90                  95

Asn Phe Glu Val Leu Phe Gly Gly Thr Lys Leu Thr Val Leu Gly
            100                 105                 110

```
<210> SEQ ID NO 5
<211> LENGTH: 351
<212> TYPE: DNA
<213> ORGANISM: Homo sapiens

<400> SEQUENCE: 5
```
gaggtgcagc tgttggagtc tgggggaggc ttggtacagc ctggggggtc cctgagactc    60
tcctgtgcag cctctggatt caccttcagt aacgcctgga tgagctgggt ccgccaggct   120
ccagggaagg ggctggagtg gtggcattt atatggtatg atggaagtaa taaatactat   180
gcagactccg tgaagggccg attcaccatc tccagagaca attccaagaa cacgctgtat   240
ctgcaaatga acagcctgag agccgaggac actgccgtgt attactgtgc gagatacagt   300
ggctggtact ttgactactg gggccaaggt acactggtca ccgtgagctc a            351

```
<210> SEQ ID NO 6
<211> LENGTH: 117
<212> TYPE: PRT
<213> ORGANISM: Homo sapiens

<400> SEQUENCE: 6
```

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Ala Phe Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Tyr Ser Gly Trp Tyr Phe Asp Tyr Trp Gly Gln Gly Thr Leu
            100                 105                 110

Val Thr Val Ser Ser
            115

<210> SEQ ID NO 7
<211> LENGTH: 336
<212> TYPE: DNA
<213> ORGANISM: Homo sapiens

<400> SEQUENCE: 7

```
cagtctgtgc tgactcagcc accctcagcg tctgggaccc ccgggcagag ggtcaccatc    60
tcctgcactg ggagcagctc caacatcggg gcaggttatg atgtacactg gtatcagcag   120
ctcccaggaa cggcccccaa actcctcatc tatgataaca acaatcggcc ctcaggggtc   180
cctgaccgat tctctggctc caagtctggc acctcagcct ccctggccat cagtgggctc   240
cggtccgagg atgaggctga ttattactgc agtcctatg acagcagcct cagtgcttgg    300
ctgttcggcg aggaaccaa gctgacggtc ctaggt                               336
```

<210> SEQ ID NO 8
<211> LENGTH: 112
<212> TYPE: PRT
<213> ORGANISM: Homo sapiens

<400> SEQUENCE: 8

```
Gln Ser Val Leu Thr Gln Pro Pro Ser Ala Ser Gly Thr Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Tyr Asp Asn Asn Asn Arg Pro Ser Gly Val Pro Asp Arg Phe
    50                  55                  60

Ser Gly Ser Lys Ser Gly Thr Ser Ala Ser Leu Ala Ile Ser Gly Leu
65                  70                  75                  80

Arg Ser Glu Asp Glu Ala Asp Tyr Tyr Cys Gln Ser Tyr Asp Ser Ser
                85                  90                  95

Leu Ser Ala Trp Leu Phe Gly Gly Gly Thr Lys Leu Thr Val Leu Gly
            100                 105                 110
```

<210> SEQ ID NO 9
<211> LENGTH: 360
<212> TYPE: DNA
<213> ORGANISM: Homo sapiens

<400> SEQUENCE: 9

```
gaggtgcagc tgttggagtc tgggggaggc ttggtacagc ctggggggtc cctgagactc    60
tcctgtgcag cctctggatt caccttcggc agttatgaaa tgaactgggt ccgccaggct   120
ccagggaagg ggctggagtg gtctcagtt atttatagcg gtggtagcac atactacgca   180
gactccgtgg aaggccgatt caccatctcc agagacaatt ccaagaacac gctgtatctg   240
caaatgaaca gcctgagagc cgaggacact gccgtgtatt actgtgcgag agatacaaac   300
ccgtactact actacggtat ggacgtctgg ggccaaggta cactggtcac cgtgagctca   360
```

<210> SEQ ID NO 10
<211> LENGTH: 120
<212> TYPE: PRT
<213> ORGANISM: Homo sapiens

<400> SEQUENCE: 10

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Ser Tyr
            20                  25                  30

Glu Met Asn Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Glu
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asp Thr Asn Pro Tyr Tyr Tyr Tyr Gly Met Asp Val Trp Gly Gln
            100                 105                 110

Gly Thr Leu Val Thr Val Ser Ser
        115                 120
```

<210> SEQ ID NO 11
<211> LENGTH: 333
<212> TYPE: DNA
<213> ORGANISM: Homo sapiens

<400> SEQUENCE: 11

```
cagtctgtgc tgactcagcc accctcagcg tctgggaccc ccgggcagag ggtcaccatc    60
tcctgttctg gaagcagctc aacatcgga aataatgctg taaactggta tcagcagctc   120
ccaggaacgg cccccaaact cctcatctat aggaataatc agcggccctc aggggtccct   180
gaccgattct ctggctccaa gtctggcacc tcagcctccc tggccatcag tgggctccgg   240
tccgaggatg aggctgatta ttactgccag tcctatgaca gcagcctgaa tggtcaagta   300
ttcggcggag gaaccaagct gacagtccta ggt                                333
```

<210> SEQ ID NO 12
<211> LENGTH: 111
<212> TYPE: PRT
<213> ORGANISM: Homo sapiens

<400> SEQUENCE: 12

```
Gln Ser Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Asn Asn
            20                  25                  30

Ala Val Asn Trp Tyr Gln Gln Leu Pro Gly Thr Ala Pro Lys Leu Leu
        35                  40                  45

Ile Tyr Arg Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Gln Ser Tyr Asp Ser Ser Leu
                85                  90                  95

Asn Gly Gln Val Phe Gly Gly Gly Thr Lys Leu Thr Val Leu Gly
            100                 105                 110
```